United States Patent
Wang et al.

(10) Patent No.: US 11,020,077 B2
(45) Date of Patent: Jun. 1, 2021

(54) SIMULTANEOUS CT-MRI IMAGE RECONSTRUCTION

(71) Applicant: RENSSELAER POLYTECHNIC INSTITUTE, Troy, NY (US)

(72) Inventors: Ge Wang, Loudonville, NY (US); Yan Xi, Troy, NY (US); Wenxiang Cong, Albany, NY (US); Jun Zhao, Shanghai (CN)

(73) Assignee: Rensselaer Polytechnic Institute, Troy, NY (US)

( * ) Notice: Subject to any disclaimer, the term of this patent is extended or adjusted under 35 U.S.C. 154(b) by 387 days.

(21) Appl. No.: 15/759,326

(22) PCT Filed: Sep. 14, 2016

(86) PCT No.: PCT/US2016/051755
§ 371 (c)(1),
(2) Date: Mar. 12, 2018

(87) PCT Pub. No.: WO2017/048856
PCT Pub. Date: Mar. 23, 2017

(65) Prior Publication Data
US 2018/0249979 A1     Sep. 6, 2018

Related U.S. Application Data

(60) Provisional application No. 62/218,239, filed on Sep. 14, 2015.

(51) Int. Cl.
*A61B 5/055* (2006.01)
*A61B 6/00* (2006.01)
(Continued)

(52) U.S. Cl.
CPC .......... *A61B 6/5247* (2013.01); *A61B 5/0035* (2013.01); *A61B 5/055* (2013.01);
(Continued)

(58) Field of Classification Search
CPC ..... A61B 6/5247; A61B 6/5205; A61B 6/032; A61B 6/035; A61B 6/4417; A61B 5/0035;
(Continued)

(56) References Cited

U.S. PATENT DOCUMENTS

2011/0116724 A1  5/2011  Bilgin
2012/0098538 A1  4/2012  Shen
(Continued)

FOREIGN PATENT DOCUMENTS

WO     2015081079     6/2015

OTHER PUBLICATIONS

Yan Xi et al., "United Iterative Reconstruction for Spectral Computed Tomography", IEEE Transactions on Medical Imaging, vol. 34, No. 3, Jul. 16, 2014 (Year: 2014).*
(Continued)

*Primary Examiner* — Amelie R Davis
*Assistant Examiner* — Adil Partap S Virk
(74) *Attorney, Agent, or Firm* — Murtha Cullina LLP; Anthony P. Gangemi

(57) ABSTRACT

Novel and advantageous systems and method for obtaining and/or reconstructing simultaneous computed tomography (CT)-magnetic resonance imaging (MRI) images are provided. Structural coupling (SC) and compressive sensing (CS) techniques can be combined to unify and improve CT and MRI reconstruction. A bidirectional image estimation method can be used to connect images from different modalities, with CT and MRI data serving as prior knowledge to each other to produce better CT and MRI image quality than would be realized with individual reconstruction.

51 Claims, 33 Drawing Sheets

(51) Int. Cl.
  *A61B 5/00* (2006.01)
  *A61B 6/03* (2006.01)
  *G01R 33/3815* (2006.01)
  *G01R 33/48* (2006.01)
  *G01R 33/56* (2006.01)
  *G06T 11/00* (2006.01)
(52) U.S. Cl.
  CPC .............. *A61B 6/032* (2013.01); *A61B 6/035* (2013.01); *A61B 6/4417* (2013.01); *A61B 6/5205* (2013.01); *G01R 33/3815* (2013.01); *G01R 33/4812* (2013.01); *G01R 33/5608* (2013.01); *G06T 11/006* (2013.01); *G06T 2211/424* (2013.01)
(58) Field of Classification Search
  CPC . A61B 5/055; A61B 6/5229; G06T 2211/424; G06T 11/006; G01R 33/3815; G01R 33/4812; G01R 33/5608; G01R 33/4808
  See application file for complete search history.

(56) References Cited

U.S. PATENT DOCUMENTS

| | | | |
|---|---|---|---|
| 2014/0212013 A1* | 7/2014 | Han | G06T 11/008 382/131 |
| 2015/0092907 A1 | 4/2015 | Dong | |
| 2015/0230766 A1* | 8/2015 | Wang | A61B 6/037 600/411 |

OTHER PUBLICATIONS

Jelena Lazovic et al. "Hexagonal Zero Mode TEM Coil: A Single Channel Coil Design for Imaging Multiple Small Animals", Magnetic Resonance in Medicine, 2005 (Year: 2005).*
Written Opinion of the International Search Authority from International Application No. PCT/US2016/051755, dated Dec. 27, 2016.

* cited by examiner

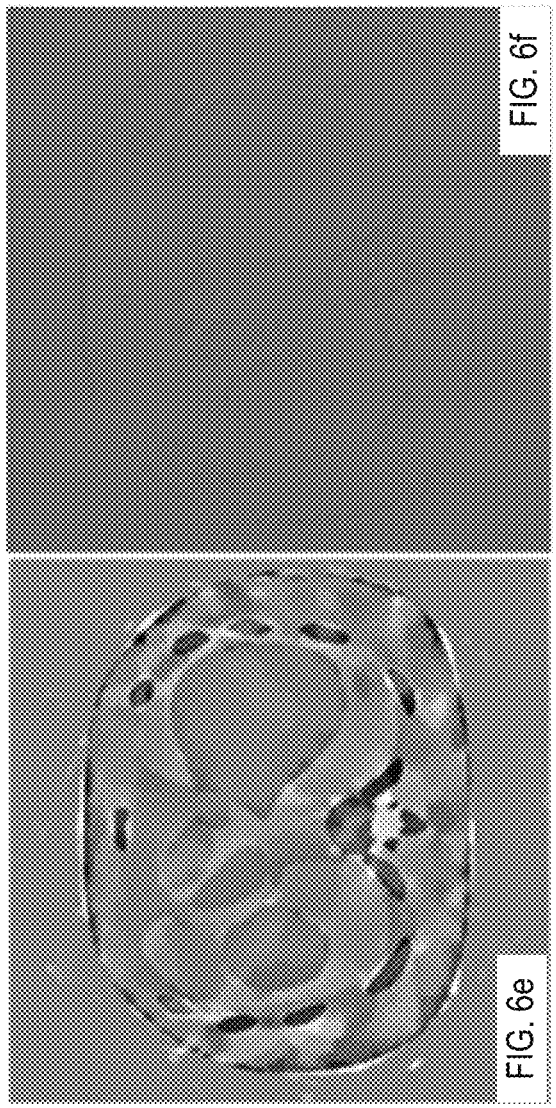
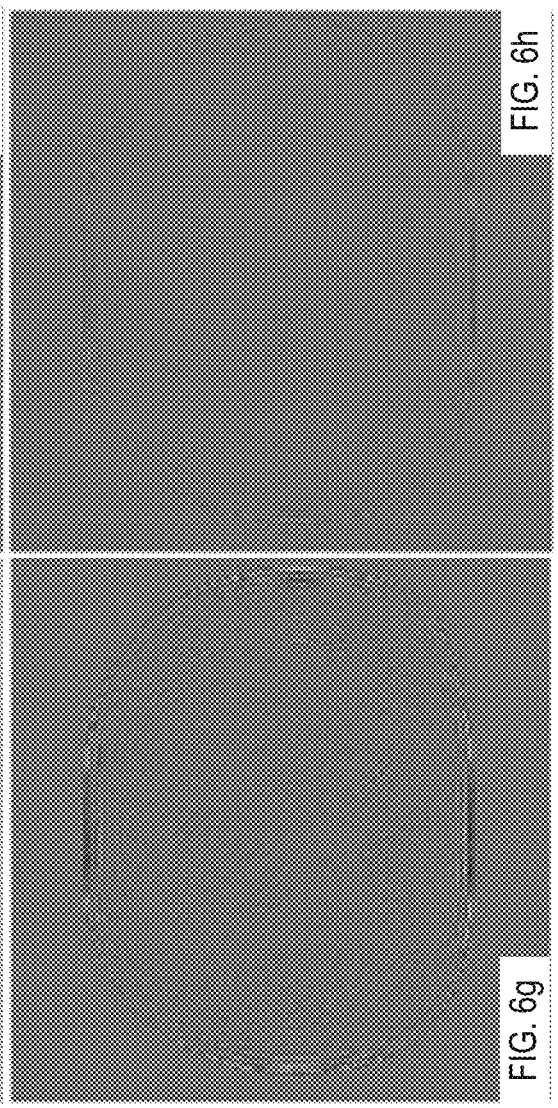

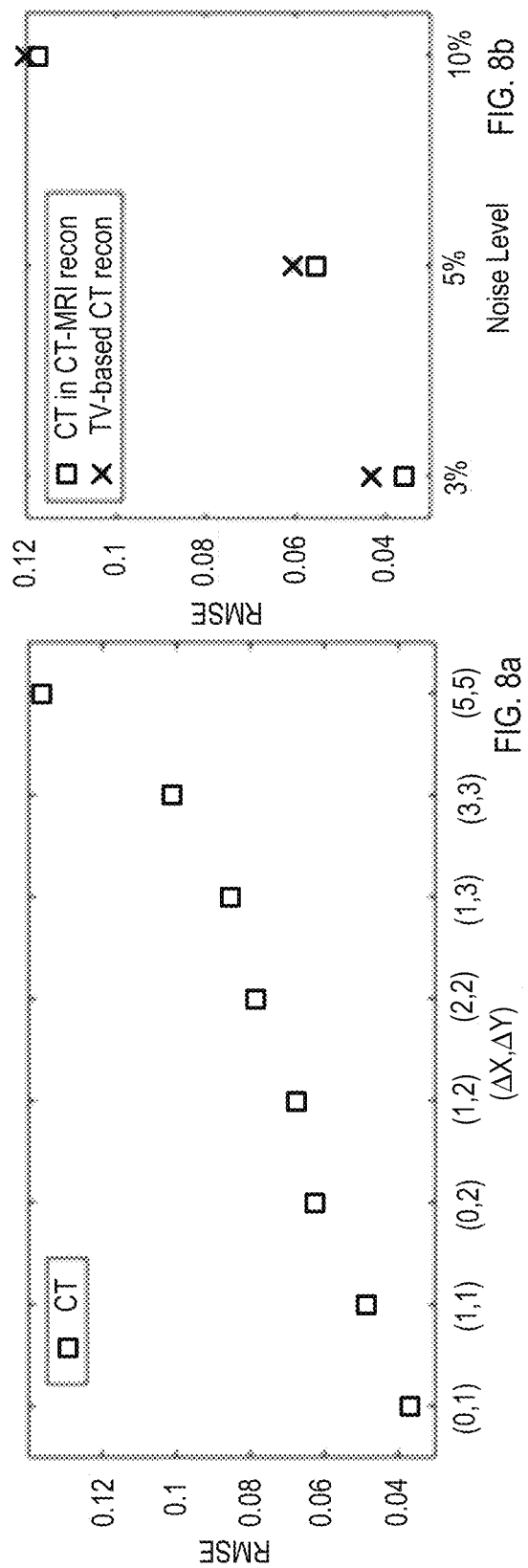
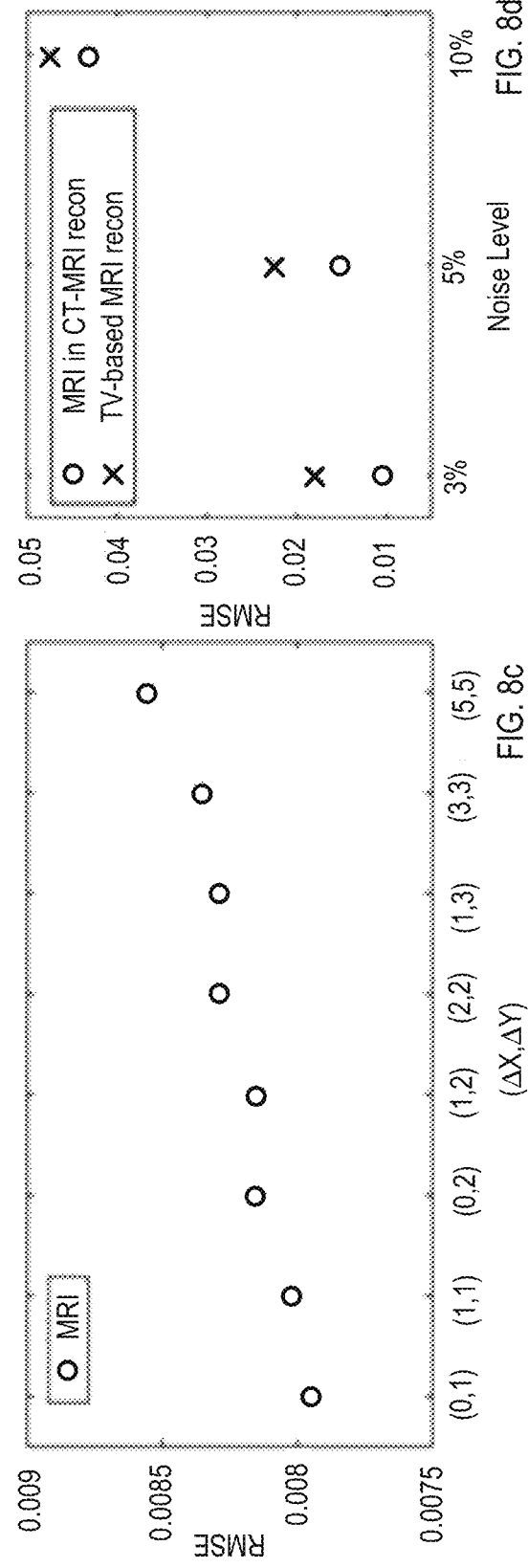

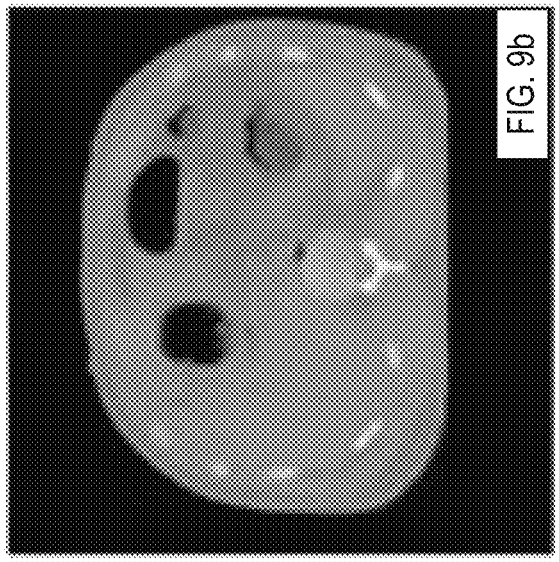
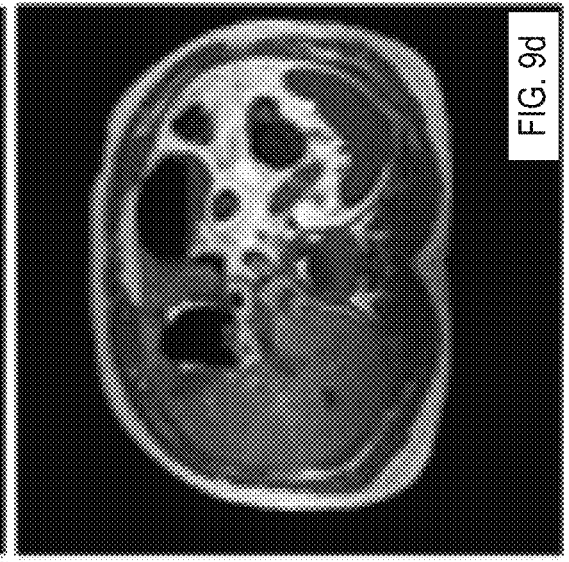
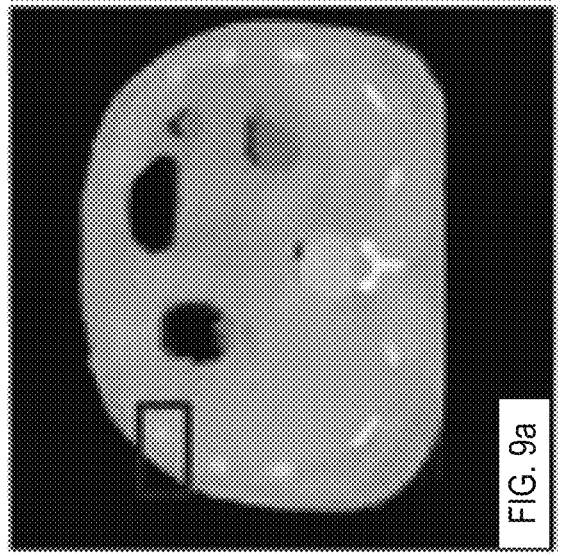
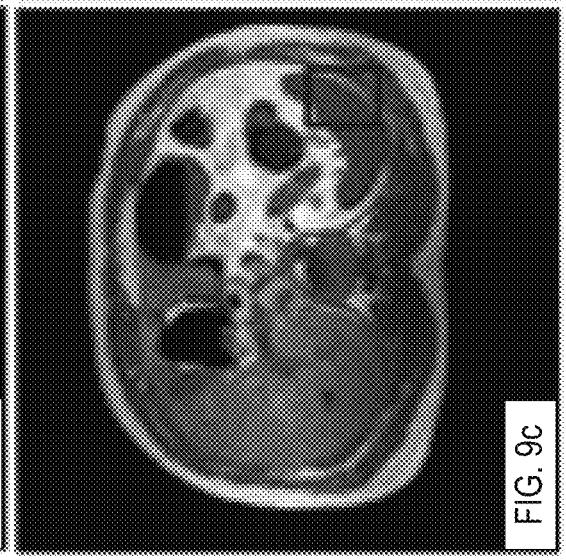
FIG. 9b
FIG. 9d
FIG. 9a
FIG. 9c

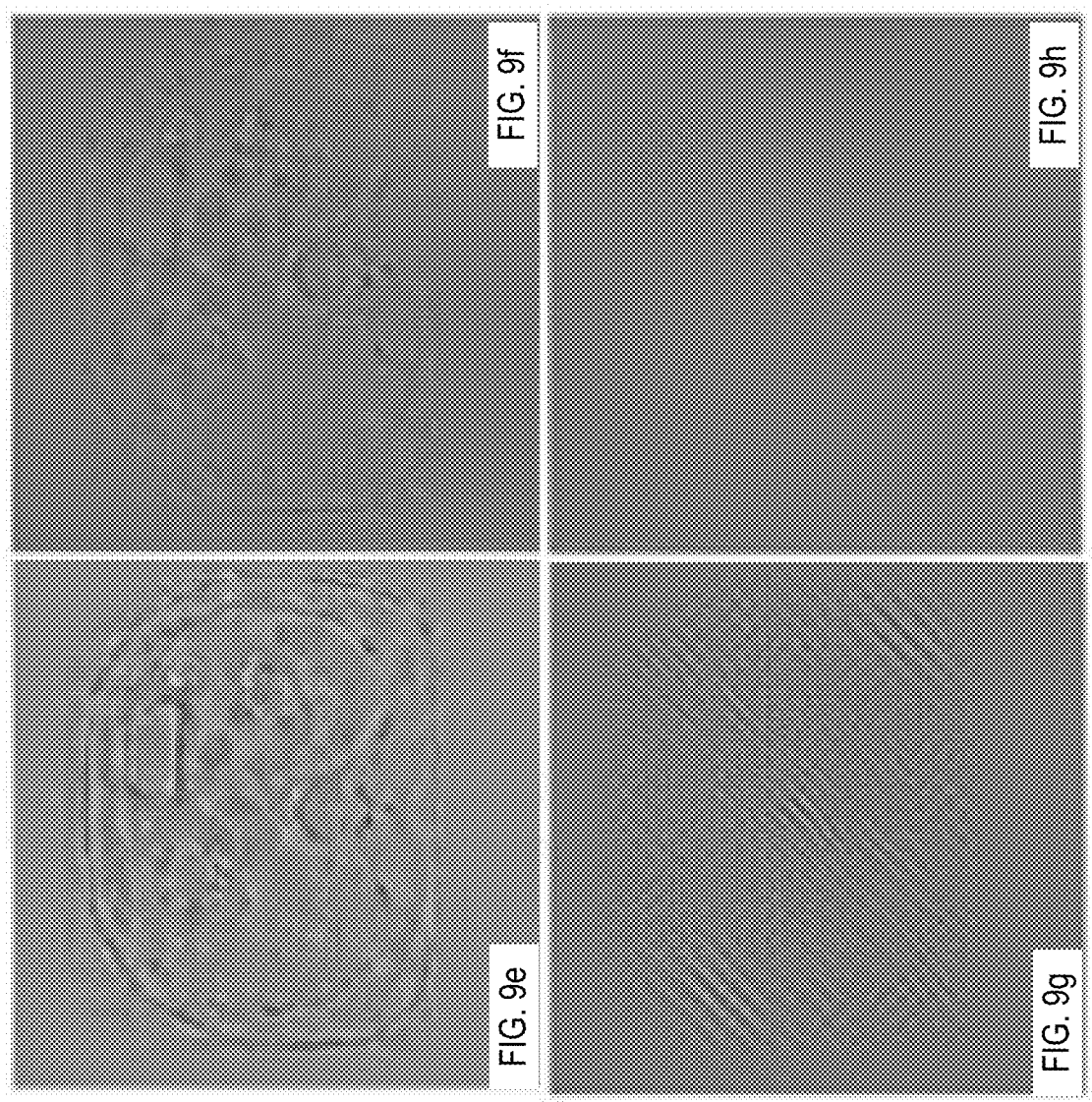

CT

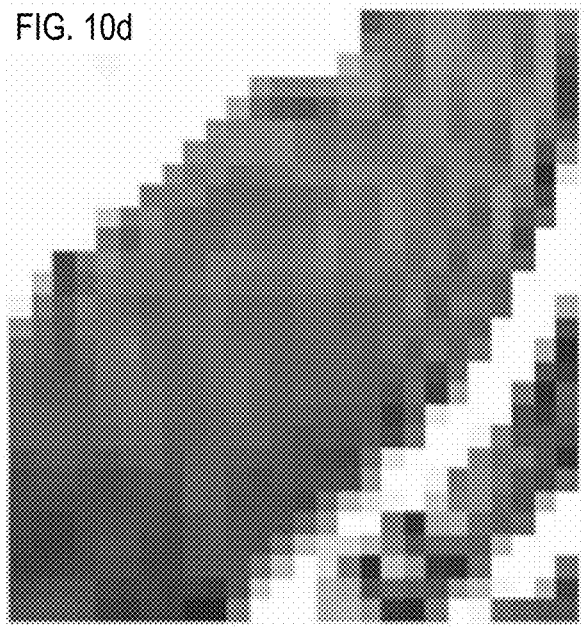
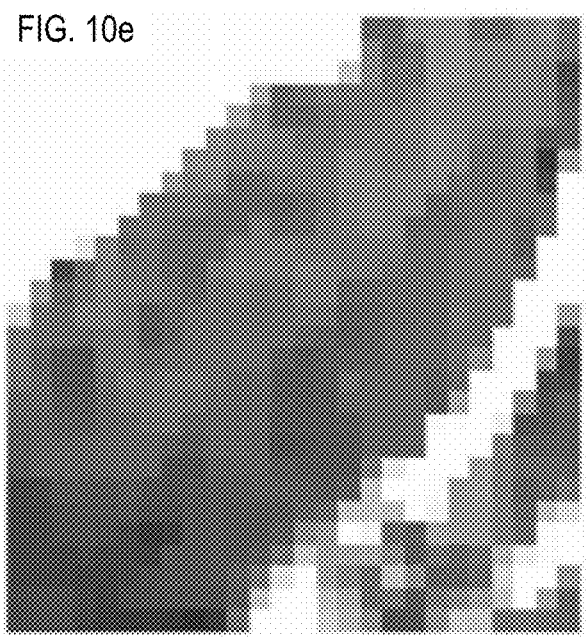
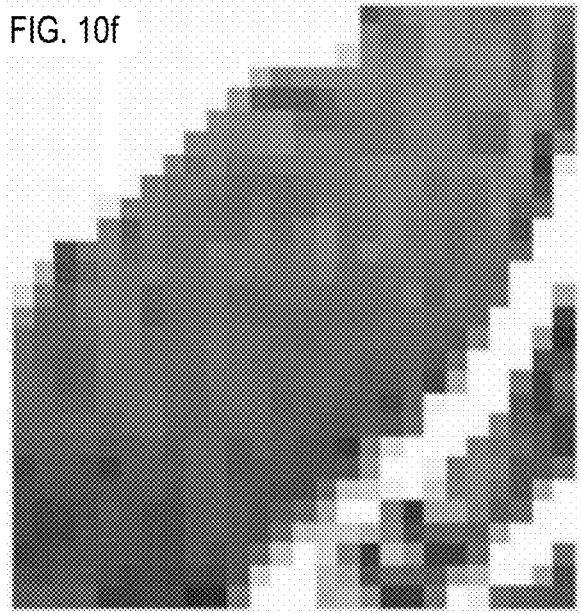
MRI

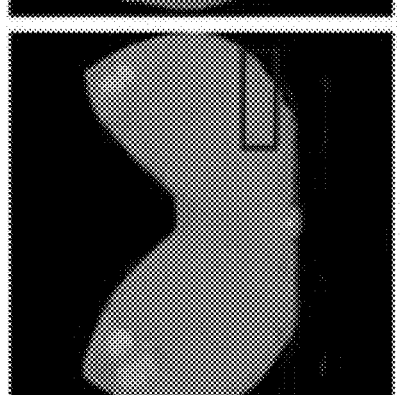
FIG. 12a
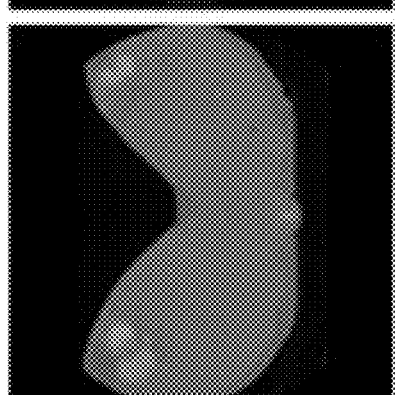
FIG. 12b
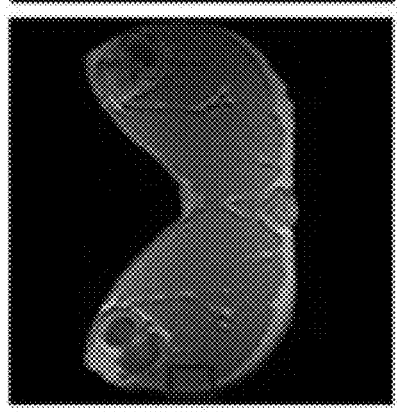
FIG. 12c
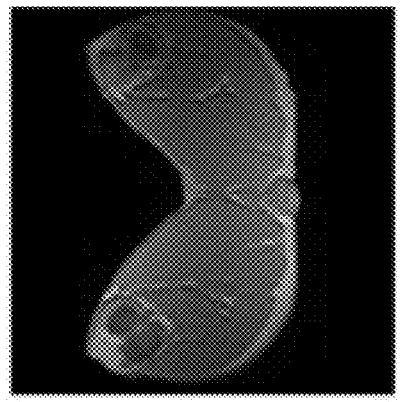
FIG. 12d
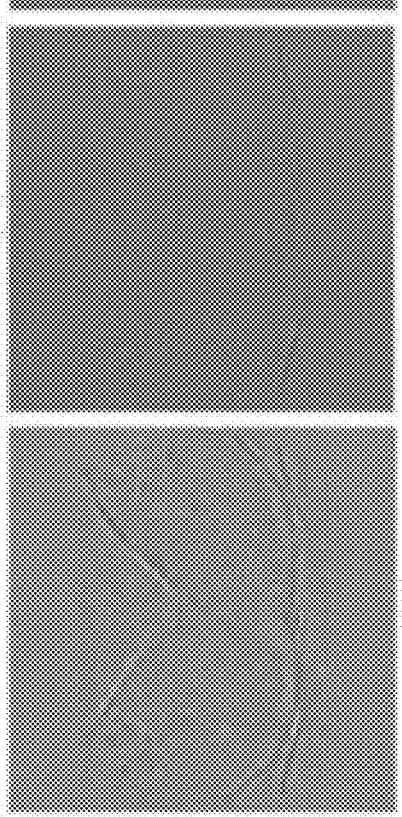
FIG. 12e
FIG. 12f
FIG. 12g
FIG. 12h CT
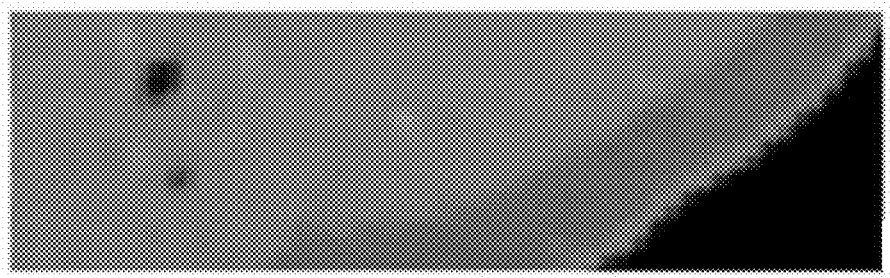
FIG. 13a
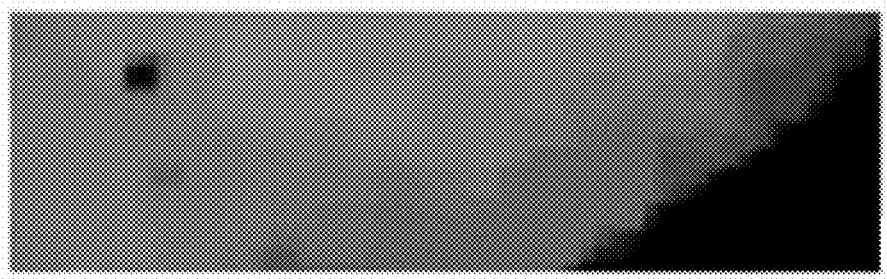
FIG. 13b
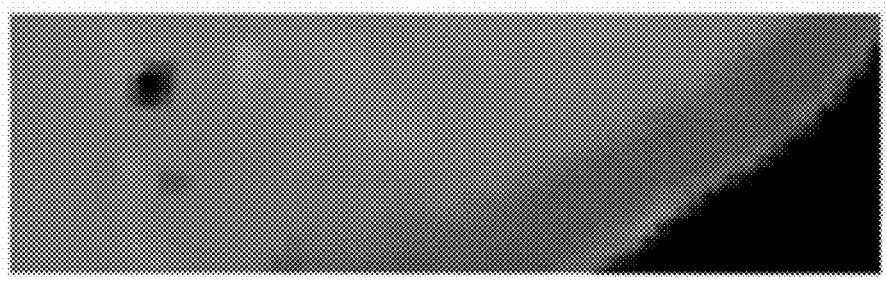
FIG. 13c
MRI
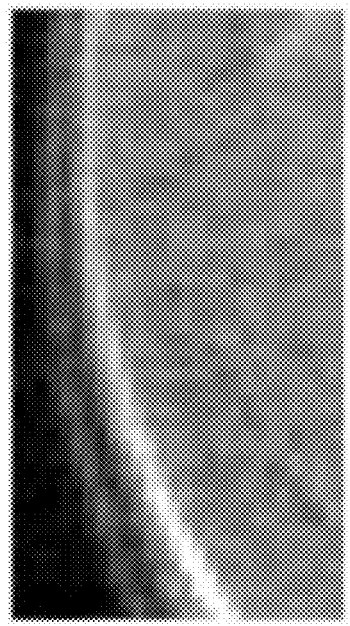 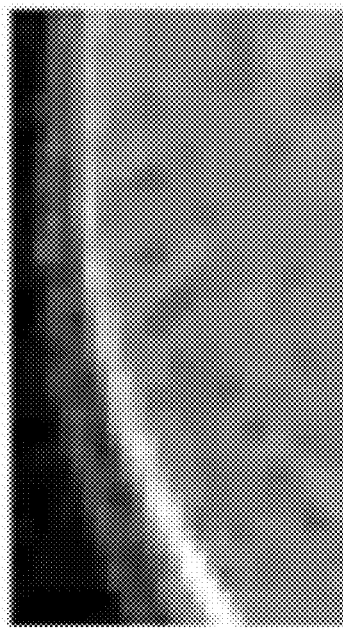 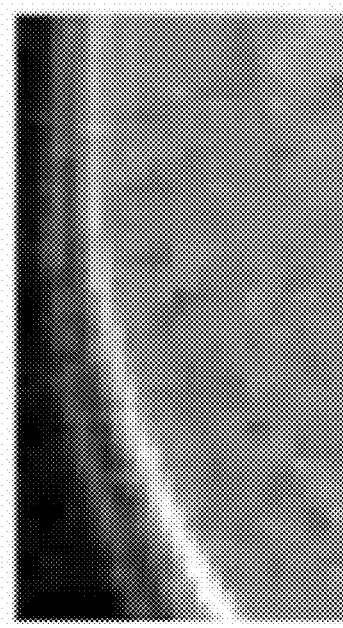
FIG. 13d     FIG. 13e     FIG. 13f

SIMULTANEOUS CT-MRI IMAGE RECONSTRUCTION

CROSS-REFERENCE TO A RELATED APPLICATION

This application is a national stage filing of International Patent Application No. PCT/US2016/051755, filed Sep. 14, 2016, which claims the benefit of U.S. Provisional Application Ser. No. 62/218,239, filed Sep. 14, 2015, which are incorporated herein by reference in their entirety.

GOVERNMENT LICENSE RIGHTS

This invention was made, at least in part, with government support under award no. NIH/NHLBI HL098912, awarded by the National Institutes of Health (NIH), National Heart, Lung, and Blood Institute (NHLBI) and National Research Service Award (NRSA) award no. T32HL098069, awarded by the NIH. The government has certain rights in the invention.

BACKGROUND

According to the National Center for Health Statistics, heart and oncologic diseases are the top two causes of mortality in the United States. Considerable strides have been made in imaging of these maladies with technologic innovations in computed tomography (CT), magnetic resonance imaging (MRI), single photon emission computed tomography/positron emission tomography (SPECT/PET), ultrasound, and optical imaging including optical coherence tomography (OCT) and fluorescence imaging. These imaging modalities are routinely used worldwide, producing critical tomographic information of the human body and enabling evaluation of not only anatomical and functional features but also cellular and molecular features in modern medicine. However, each individual imaging modality has its own contrast mechanism with strengths and weaknesses, and imaging protocols depend on many interrelated factors. Both individual (CT, MRI, PET, and SPECT) and hybrid modalities (PET/SPECT-CT and PET/MRI) are clinically accepted with strong evidence of healthcare benefits.

Prior to the availability of hybrid PET-CT, separate CT and PET scans were performed often with longer scanning time and poor anatomic localization of radionuclide uptake, due to post-acquisition image fusion errors. More recently, hybrid PET-CT has become an indispensable modality for cancer staging and assessing treatment response. Recent availability of hybrid PET-MRI goes a step further, providing both superior detection and characterization of abnormalities from MRI and metabolic information from PET. While PET provides critical functional information to PET-CT and PET-MRI, both CT and MRI help enhance PET information and enable better diagnostic performance.

Each tomographic modality has distinct advantages, including high temporal and spatial resolution with CT, excellent tissue characterization and nonionizing radiation with MRI; and high sensitivity for molecular imaging with SPECT or PET. However, no single modality is sufficient to depict the complex dynamics of mammalian physiology and pathology. As evidenced by SPECT-CT and PET-CT scanners, modality fusion imaging can be effective and synergistic and has had tremendous impact on both experimental discovery and clinical care. Even with current multi-modality imaging, though, limitations exist, including reconstruction techniques that are inefficient and/or inaccurate.

BRIEF SUMMARY

Embodiments of the subject invention provide novel and advantageous systems and method for obtaining and/or reconstructing simultaneous computed tomography (CT)-magnetic resonance imaging (MRI) images. Structural coupling (SC) and compressive sensing (CS) techniques can be combined to unify and improve CT and MRI reconstruction. A bidirectional image estimation method can be used to connect images from different modalities, with CT and MRI data serving as prior knowledge to each other to produce better CT and MRI image quality than would be realized with individual reconstruction.

In one embodiment, a method of reconstructing CT and MRI images can comprise: reconstructing a CT image from CT data; reconstructing an MRI image from MRI data; setting an iteration step to zero; transforming a CT-MRI dataset by the CT image and the MRI image; estimating the corresponded CT-MRI image according to the CT image and the MRI image aided by the CT-MRI dataset; reconstructing the CT image with the estimated CT-MRI image and the CT data; reconstructing the MRI image with the CT-MRI image and the MRI data; adding one to the iteration step; and repeating the steps between setting an iteration step to zero and adding one to the iteration step, until meeting stop criteria, at which point the current estimated reconstructed CT image is the reconstructed CT image and the current estimated reconstructed MRI image is the reconstructed MRI image.

In another embodiment, a system for simultaneous CT-MRI can comprise: a CT subsystem for obtaining CT data; an MRI subsystem for obtaining MRI data; at least one processor; and a machine-readable medium, in operable communication with the CT subsystem, the MRI subsystem, and the at least one processor, having machine-executable instructions stored thereon that, when executed by the at least one processor, perform a method of reconstructing CT and MRI images. The MRI subsystem can comprise superconducting magnets. Also, the method of reconstructing CT and MRI images can be such a method as described herein.

BRIEF DESCRIPTION OF THE DRAWINGS

FIG. 1c shows a line profile along the dotted line of FIG. 1a.

FIG. 6e is an image of the residual error relative to ground truth for the reconstruction of FIG. 6a.

FIG. 6f is an image of the residual error relative to ground truth for the reconstruction of FIG. 6b.

FIG. 6g is an image of the residual error relative to ground truth for the reconstruction of FIG. 6c.

FIG. 6h is an image of the residual error relative to ground truth for the reconstruction of FIG. 6d.

FIG. 8a shows a plot of RMSE with respect to various registration errors ($\Delta x, \Delta y$) for CT images in simultaneous CT-MRI construction in a mNCAT experiment.

FIG. 8b shows a plot of RMSE with respect to various registration errors ($\Delta x, \Delta y$) for MRI images in simultaneous CT-MRI construction in a mNCAT experiment.

FIG. 8c shows a plot of RMSE with respect to various noise levels for simultaneous CT-MRI construction (squares) and TV-based reconstruction ("x" data points) for CT images in a mNCAT experiment.

FIG. 8d shows a plot of RMSE with respect to various noise levels for simultaneous CT-MRI construction (circles) and TV-based reconstruction ("x" data points) for MRI images in a mNCAT experiment.

FIG. 9a shows a CT image for a VHP simulation, reconstructed using TV-based reconstruction.

FIG. 9b shows a CT image for a VHP simulation, reconstructed using simultaneous CT-MRI reconstruction according to an embodiment of the subject invention.

FIG. 9c shows an MRI image for a VHP simulation, reconstructed using TV-based reconstruction.

FIG. 9d shows an MRI image for a VHP simulation, reconstructed using simultaneous CT-MRI reconstruction according to an embodiment of the subject invention.

FIG. 9e is an image of the residual error relative to ground truth for the reconstruction of FIG. 9a.

FIG. 9f is an image of the residual error relative to ground truth for the reconstruction of FIG. 9b.

FIG. 9g is an image of the residual error relative to ground truth for the reconstruction of FIG. 9c.

FIG. 9h is an image of the residual error relative to ground truth for the reconstruction of FIG. 9d.

FIG. 10d shows a local enlarged view of a ground truth MRI image for a VHP experiment.

FIG. 10e shows a local enlarged view of a reconstructed MRI image for a VHP experiment, reconstructed using TV-based reconstruction.

FIG. 10f shows a local enlarged view of a reconstructed MRI image for a VHP experiment, reconstructed using simultaneous CT-MRI reconstruction according to an embodiment of the subject invention.

FIG. 12a shows a CT image for a porcine sample simulation, reconstructed using TV-based reconstruction.

FIG. 12b shows a CT image for a porcine sample simulation, reconstructed using simultaneous CT-MRI reconstruction according to an embodiment of the subject invention.

FIG. 12c shows an MRI image for a porcine sample simulation, reconstructed using TV-based reconstruction.

FIG. 12d shows an MRI image for a porcine sample simulation, reconstructed using simultaneous CT-MRI reconstruction according to an embodiment of the subject invention.

FIG. 12e is an image of the residual error relative to ground truth for the reconstruction of FIG. 12a.

FIG. 12f is an image of the residual error relative to ground truth for the reconstruction of FIG. 12b.

FIG. 12g is an image of the residual error relative to ground truth for the reconstruction of FIG. 12c.

FIG. 12h is an image of the residual error relative to ground truth for the reconstruction of FIG. 12d.

FIG. 13a shows a local enlarged view of a ground truth CT image for a porcine sample experiment.

FIG. 13b shows a local enlarged view of a reconstructed CT image for a porcine sample experiment, reconstructed using TV-based reconstruction.

FIG. 13c shows a local enlarged view of a reconstructed CT image for a porcine sample experiment, reconstructed using simultaneous CT-MRI reconstruction according to an embodiment of the subject invention.

FIG. 13d shows a local enlarged view of a ground truth MRI image for a porcine sample experiment.

FIG. 13e shows a local enlarged view of a reconstructed MRI image for a porcine sample experiment, reconstructed using TV-based reconstruction.

FIG. 13f shows a local enlarged view of a reconstructed MRI image for a porcine sample experiment, reconstructed using simultaneous CT-MRI reconstruction according to an embodiment of the subject invention.

DETAILED DESCRIPTION

Figure 1A:
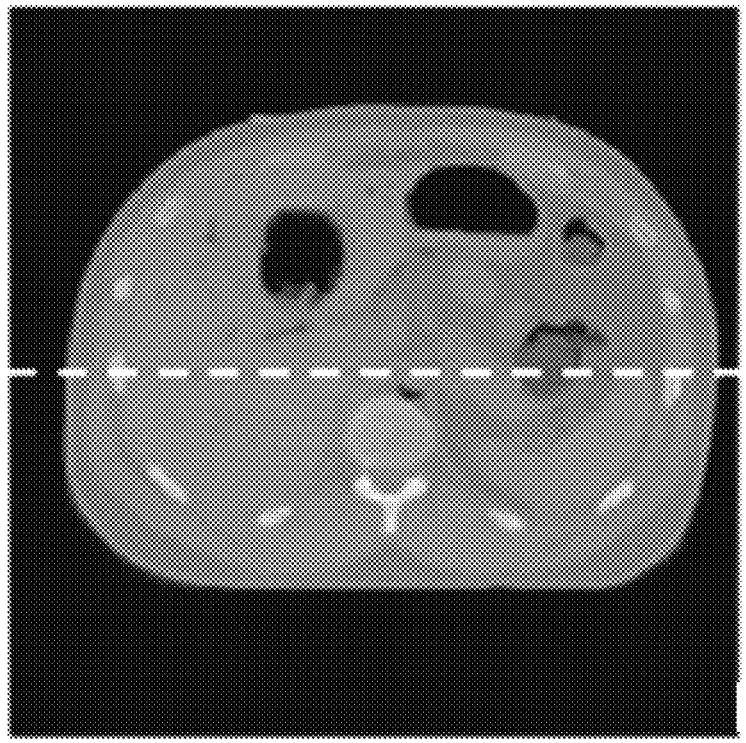
FIG. 1a shows a computed tomography (CT) image of a human abdomen, normalized into [0,1].

Embodiments of the subject invention provide novel and advantageous systems and method for obtaining and/or reconstructing simultaneous computed tomography (CT)-magnetic resonance imaging (MRI) images. Structural coupling (SC) and compressive sensing (CS) techniques can be combined to unify and improve CT and MRI reconstruction. A bidirectional image estimation method can be used to connect images from different modalities, with CT and MRI data serving as prior knowledge to each other to produce better CT and MRI image quality than would be realized with individual reconstruction.

Despite recent advances, CT as an independent imaging modality is limited by the associated radiation burden and lack of tissue characterization, and MRI as an independent imaging modality is limited by its longer imaging time and low signals from aerated lungs and calcified and/or ossified structures. Synchronized CT-MRI can address the limitations of each imaging modality individually while improving the diagnostic content and abbreviating the imaging processes.

Multimodality imaging has major clinical advantages. While there can be different versions, CT technologies has generally gone from the first generation for translation-rotation in parallel-beam geometry to the latest generation with spiral/helical multi-slice/cone-beam scanning. Analogous to CT generations, the development of multimodality imaging technologies progressed from sequential acquisition to simultaneous positron emission tomography (PET)-CT and PET-MRI scanners. Integrated multimodality imaging systems such as PET-CT, single photon emission computed tomography (SPECT)-CT, and PET-MRI have gained acceptance as clinical and research tools after initial skepticism, but CT-MRI has greater technical challenges. In many cases (e.g., vascular structures, osseous constructs, and some features of soft tissues/organs with exogenous contrast), CT offers exquisite anatomic information at fine resolution with fast speed. With photon-counting detectors, it is feasible to obtain spectral or multi-energy CT images for material characterization that promises significantly better diagnostic performance than current dual-energy CT techniques.

On the other hand, MRI captures functional, flow-related, and tissue-specific signals with excellent contrast. By using superconducting magnets (e.g., room-temperature superconducting magnets), embodiments of the subject invention can use localized and inhomogeneous field-based MRI techniques for higher imaging flexibility. Also, new pulse sequences can be designed to produce even richer physiological and pathological information, highly complementary to that from CT. For example, nanoparticles can be functionalized to target different peptides and receptors, made to enhance features for both CT and MRI, and have great clinical potential. In many embodiments, a simultaneous CT-MRI scanner can provide a synergistic imaging tool to study intrinsic complexity and dynamic character of real biological and pathological processes in non-contrast/contrast-enhanced cardiovascular and oncologic applications.

In existing clinical imaging, the synchronization of CT and MRI is the only missing link among the three most popular tomographic modalities: CT, MRI, and PET/SPECT. The two principal technical difficulties for simultaneous CT-MRI in the related art are: (1) space constraints given the physical bulkiness of CT and MRI scanners; and (2) the electromagnetic interference between them. Embodiments of the subject invention can take advantage of enabling technology for simultaneous CT-MRI in the form of interior tomography theory and methods. Simultaneous CT-MRI can enable synergistic physiological and morphologic imaging applications for cardiac diseases, stroke, and cancer, offering unique information for diagnosis and therapy of many common but complicated diseases.

Omnitomography can be considered an ultimate form of modality fusion, and a simultaneous CT-MRI scanner can be considered a special case of omnitomography that combines high spatial resolution of CT with high contrast resolution of MRI (see also Wang et al., Towards omnitomography—Grand fusion of multiple modalities for simultaneous interior tomography," PloS One, vol. 7, p. e39700, 2012; which is hereby incorporated by reference herein in its entirety). The advantages of merging tomographic imaging modalities can go beyond complementary attributes, potentially improving results for any individual modality and providing promise for improved functional imaging studies and radiation therapy.

Figure 16A:
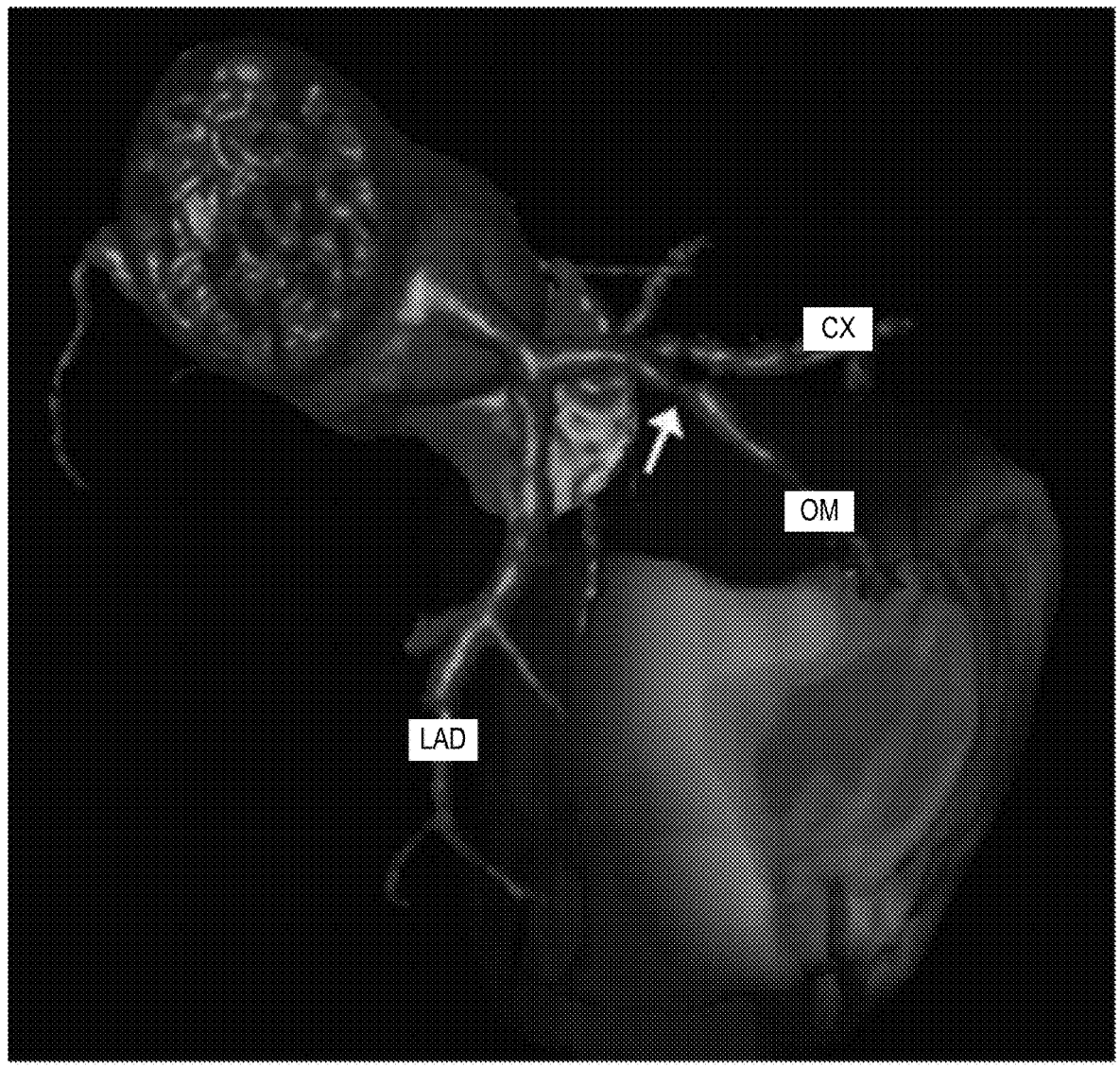
FIG. 16a shows an image of a retrospective combination of a CT coronary angiography scan and a cardiac MRI scan.
Figure 16B:
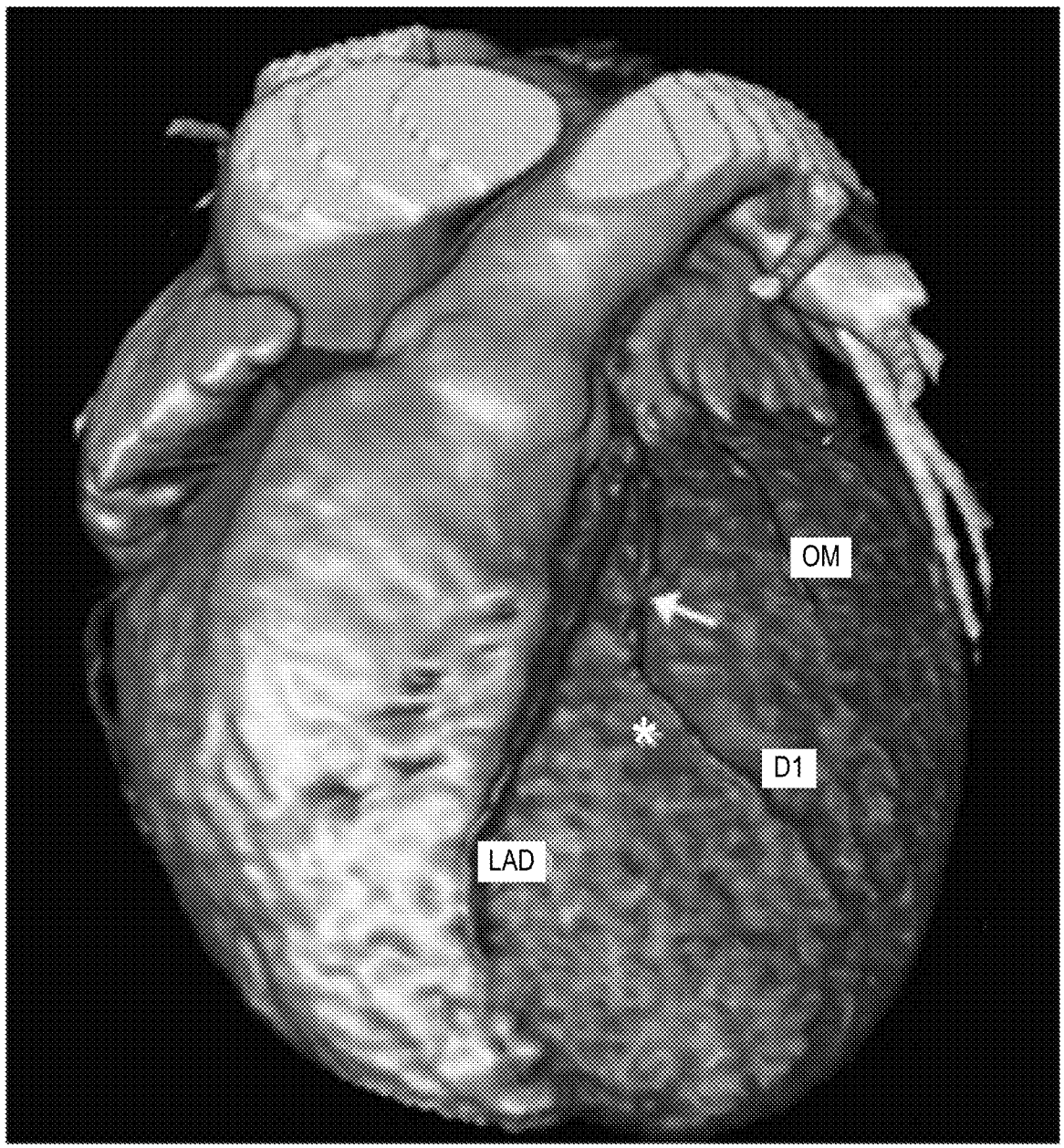
FIG. 16b shows an image of a retrospective combination of a CT coronary angiography scan and a cardiac MRI scan.

FIGS. 16a and 16b show two retrospective combinations of a CT coronary angiography scan and a cardiac MRI scan. Referring to FIG. 16a, a fused surface rendering of the segmented coronary artery tree from low-dose CT with the mask representing the myocardium of the left ventricle and the segmented data from late gadolinium enhancement (LGE) are shown. Lateral LGE can be assigned to a high grade stenosis (indicated by the arrow in FIG. 16a) of the obtuse marginal (OM) branch of the circumflex artery (CX). The extent of transmurality of LGE can be displayed in a color-coded fashion. No stenosis can be seen in the segmented left anterior descending (LAD) artery and proximal CX. Referring to FIG. 16b, segmented myocardial defects from cardiac MRI are integrated with a volume rendering based on low-dose CT. Low-dose CT can demonstrate the LAD and OM branch of circumflex artery and significant stenosis (indicated by arrow in FIG. 16b) of the first diagonal branch (D1). The fused images show an anterolateral perfusion deficit (indicated by the asterisk in FIG. 16b) in relation to the D1 stenosis (arrow). FIGS. 16a and 16b are adapted from Donati et al. (3D fusion of functional cardiac magnetic resonance imaging and computed tomography coronary angiography: Accuracy and added clinical value, Invest. Radiol. 46, 331-340, 2011), which is hereby incorporated by reference herein in its entirety.

Simultaneous CT-MRI has the potential to change the care of patients with cardiac diseases by allowing each modality to use its strengths to address the limitations of the other. Noninvasive identification and localization of vulnerable plaques may be optimally performed with synchronized CT (superior temporal and spatial resolution) and MRI (superior tissue contrast) scanning, which can substantially change prophylactic treatment of patients with vulnerable plaques. With simultaneous acquisition, CT can exclude significant coronary artery disease while synchronized MRI can assess plaque composition and myocardial function. In addition, simultaneous CT-MRI may have a crucial role in acute stroke. The window of opportunity is short to treat a patient with acute stroke, typically between three and six hours from the onset of symptoms. Simultaneous CT and MRI can help determine eligibility of the patient to receive thrombolytic therapy and recover or limit loss of neurological functions.

Simultaneous CT-MRI also has the potential to enrich information from dynamic contrast-enhanced (DCE) studies by cross calibrating each modality and coupling dynamic features. This can enable routine evaluation of sophisticated tumor perfusion metrics, which will help in tumor characterization and therapeutic assessment. Combined imaging modalities frequently use contrast agents—radiopharmaceuticals, intravascular agents, and multifunctional nanoparticles—to expand their capabilities. Because conventional CT and MRI use different dedicated agents, the potential for multifunctional CT-MRI nanoparticles is particularly important.

Figure 17A:
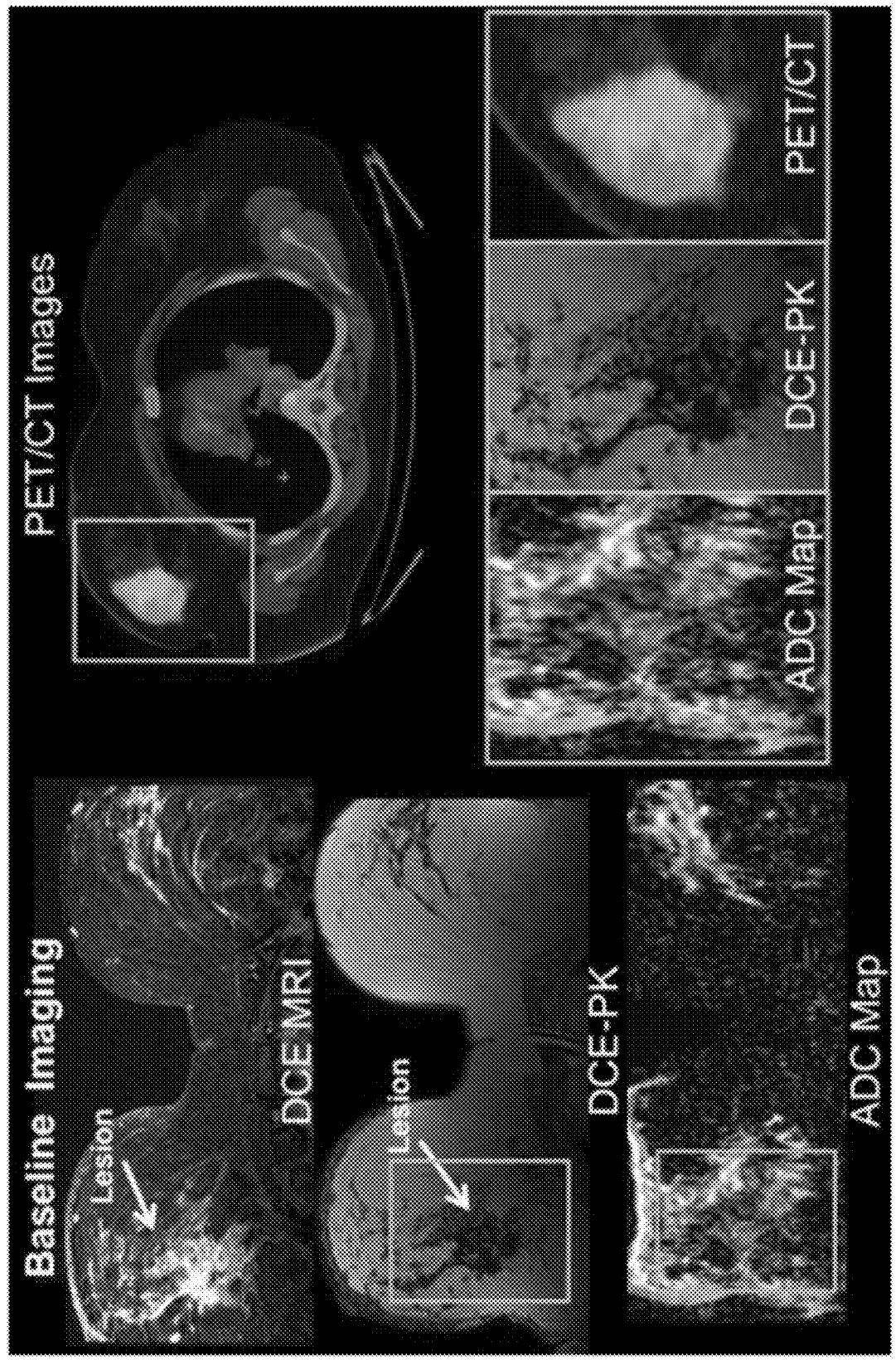
FIG. 17a shows parametric images (apparent diffusion coefficient (ADC) and pharmacokinetic (PK)) derived from measured data.
Figure 17B:
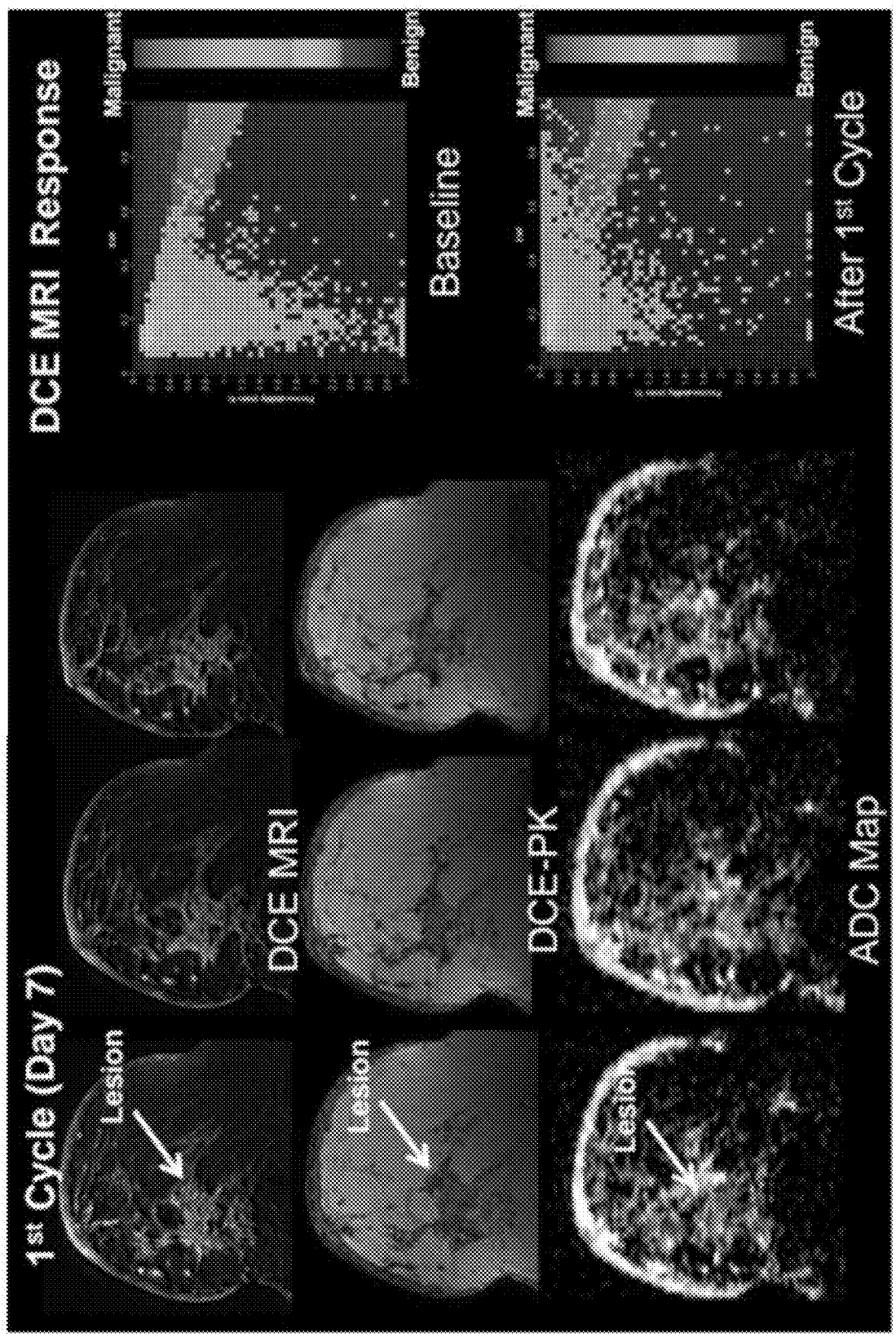
FIG. 17b shows comparison of the pretreatment baseline scan of FIG. 17a with a single cycle of therapy.

FIG. 17a shows parametric images (apparent diffusion coefficient (ADC) and pharmacokinetic (PK)) derived from measured data, and FIG. 17b shows comparison of the pretreatment baseline scan of FIG. 17a with a single cycle of therapy. Referring to FIG. 17a, ADC was computed from pre-contrast diffusion weighted MRI images, and dynamic contrast enhanced (DCE)-PK from PK compartmental modeling coefficients determined using a temporal sequence of pre- and post-contrast images. The kinetic model is known and not shown. Referring to FIG. 17b, the tumor displayed mostly high permeability red voxels before treatment and mostly green voxels (decreasing permeability and increasing extravascular fraction (EVF)) after treatment. The response to therapy is also depicted in the joint histograms at the right side of FIG. 17b-baseline above and "after 1 cycle" below. The color scale shows benign characteristics of DCE response in blue and malignant response in yellow red. The axes include EVF (abscissa) versus reciprocal permeability (ordinate). The results show major changes between baseline and therapy, indicating that the response to therapy can be known using parametric images long before morphologic changes, such as change in tumor size, may be detected. FIGS. 17a and 17b are reproduced from Jacobs et al. (Multiparametric and multimodality functional radiological imaging for breast cancer diagnosis and early treatment response assessment, J. Natl. Cancer Inst. Monogr. 2015, 40-46; see also the "References" section).

Multimodality imaging may be required for effective multimodality therapy, and modality integration can facilitate the principal tasks including target definition, treatment planning, verification, and monitoring. The advantage to acquiring CT and MRI data simultaneously during dynamic contrast enhancement comes from the fact that both modalities provide contrast kinetic parameters, but the assumptions, intrinsic errors, and limitations of the modeling processes are quite different and hence potentially synergistic. Therefore, better characterization of the imaged tissues may become available once simultaneously imaged.

While CT and MRI are the two most utilized tomographic modalities, their physical combination has not been attempted in a clinical setting. A CT scanner works with high-speed rotating metallic parts including at least one X-ray tube and a detector assembly. An MRI scanner relies on high-strength and high-frequency magnetic fields. The combination of the CT and MRI scanners is made challenging at least by the geometric constraints and electromagnetic interference. Interior tomography is a key strategy to overcome both in simultaneous CT-MRI, along with X-ray radiation dose reduction.

Interior tomography is a unique feature of simultaneous CT-MRI. The classic strategy in the CT field has been that a whole cross section must be completely covered by a fan- or cone-beam of X-rays, and resultant measures must be transformed into sufficient radon (line or planar integral) data, or equivalently the Fourier space must be fully sampled for accurate and reliable image reconstruction. However, biomedical applications often focus on a region of interest (ROI), for example, a cardiac chamber, a tumor mass, and/or a surgical region. Therefore, data truncation for theoretically exact tomographic quantification can be useful.

Figure 18A:
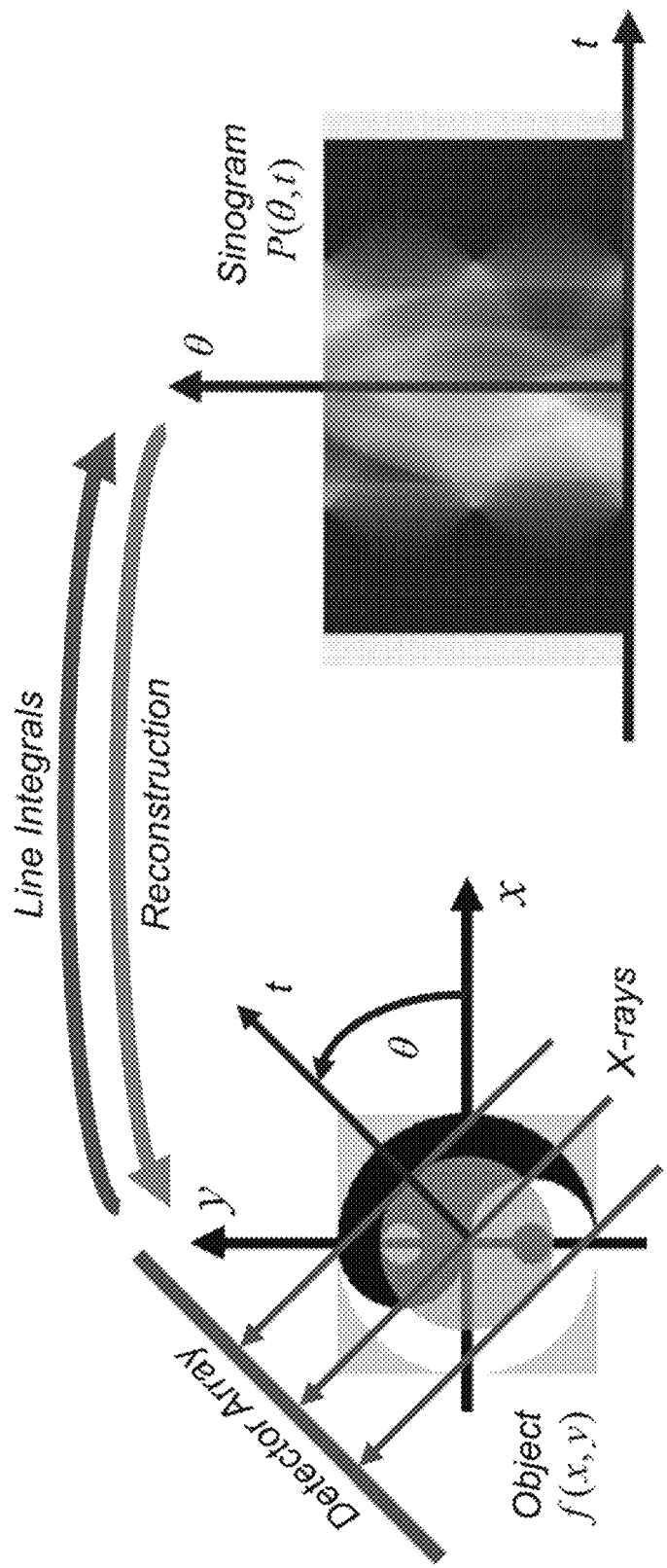
FIG. 18a shows a schematic view of traditional X-ray tomographic reconstruction.
Figure 18C:
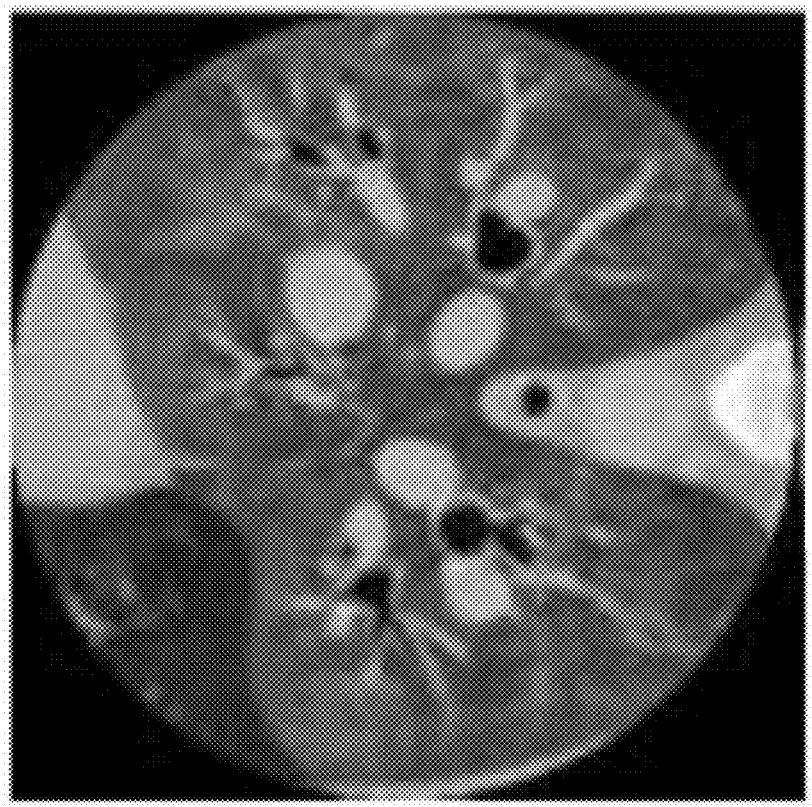
FIG. 18c shows an image of a reconstructed image of the ROI of FIG. 18b, using interior tomography.
Figure 18B:
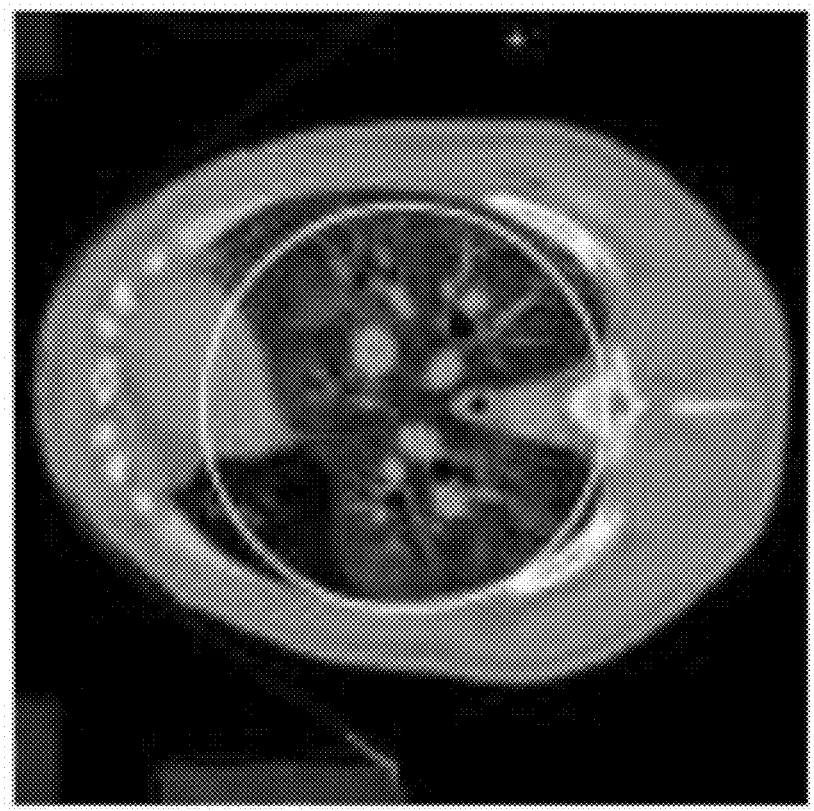
FIG. 18b shows a reconstructed image of a sheep chest from a complete dataset (region of interest (ROI) in the circle).

Mathematically speaking, cone-beam spiral CT reconstruction is essentially handling longitudinal data truncation complicated by the divergence of X-rays. Orthogonal to the longitudinal data truncation is the transverse data truncation problem. The conventional fan-beam scanning involves no data truncation. On the other hand, the interior problem is associated with a narrow scanning beam. Only X-rays that go through an interior ROI are used to generate truncated projection data, as shown in FIG. 18a. This interior problem has no unique solution, but if there is a known subregion in the ROI, the interior problem can be uniquely and stably solved. The assumption of a known subregion is practical such as air in an airway or blood in an aorta. However, once contrast material is injected for cardiac CT, blood density cannot be assumed as known. If the attenuation coefficients in a ROI can be well approximated by a piecewise constant/polynomial function, the solution to the interior problem is unique. For a piecewise polynomial ROI the solution to the interior problem is not only unique but also stable. Interior tomography produces excellent local reconstruction in practice, as shown in FIGS. 18b and 18c.

FIG. 18a shows a schematic view of traditional X-ray tomographic reconstruction; FIG. 18b shows a reconstructed image of a sheep chest from a complete dataset (region of interest (ROI) in the circle); and FIG. 18c shows an image of a reconstructed image of the ROI of FIG. 18b, using interior tomography (Wang et al., Can interior tomography outperform lambda tomography?, Proc. Natl. Acad. Sci. U.S.A 107, E92-E93, 2010; see also the "References" section). Referring to FIG. 18a, an internal region (the red disk on the left) can be reconstructed from truncated data (the red (innermost) rectangle on the right), and, in principle, line integrals along paths not directly involving the local region (the green (outer) rectangles on the right) can be irrelevant. Traditional X-ray tomographic reconstruction can be theoretically exact or very accurate if all the data are precisely acquired along paths through an object support.

Based on X-ray interior tomography results, it can be the case that accurate and reliable local image reconstruction only needs indirect measurement that directly involves a ROI. Indeed, this is theoretically valid for other medical imaging modalities. For interior MRI, the requirement of the background magnetic field can be relaxed. In contrast to the popular concept that a homogeneous background magnetic field large enough to contain a whole cross section through a patient is needed, a much smaller homogeneous background magnetic field can be used. Then, focused RF excitation and truly interior algorithms can be used for image reconstruction. Interior MRI with an inhomogeneous field can also be used. With interior tomography, CT and MRI systems can be made compact to provide space for coexistence and facilitate shielding for seamless integration.

In many embodiments, a unified reconstruction framework can be used for simultaneous and integrated CT-MRI image reconstruction. Structural coupling (SC) and compressive sensing (CS) techniques can be combined to unify and improve CT and MRI reconstruction. In some embodiments, a bidirectional image estimation method can be used to connect images from different modalities. CT and MRI data can serve as prior knowledge to each other to produce better CT and MRI image quality than would be realized with individual reconstruction. The SC method is similar to dictionary learning (DL), yet the former is more efficient and flexible than the latter for modality fusion imaging and content-based image estimation (see also Xi et al., United iterative reconstruction for spectral computed tomography, IEEE Trans. Med. Imag., vol. 34, no. 3, pp. 769-778, Mar. 2015; and Xi et al., A hybrid CT-MRI reconstruction method, presented at the IEEE Int. Symp. Biomedical Imaging, Beijing, China, 2014; both of which are incorporated by reference herein in their entireties). SC is based on local features and establishes a connection between different modality images via a table of paired image patches.

Figure 19:
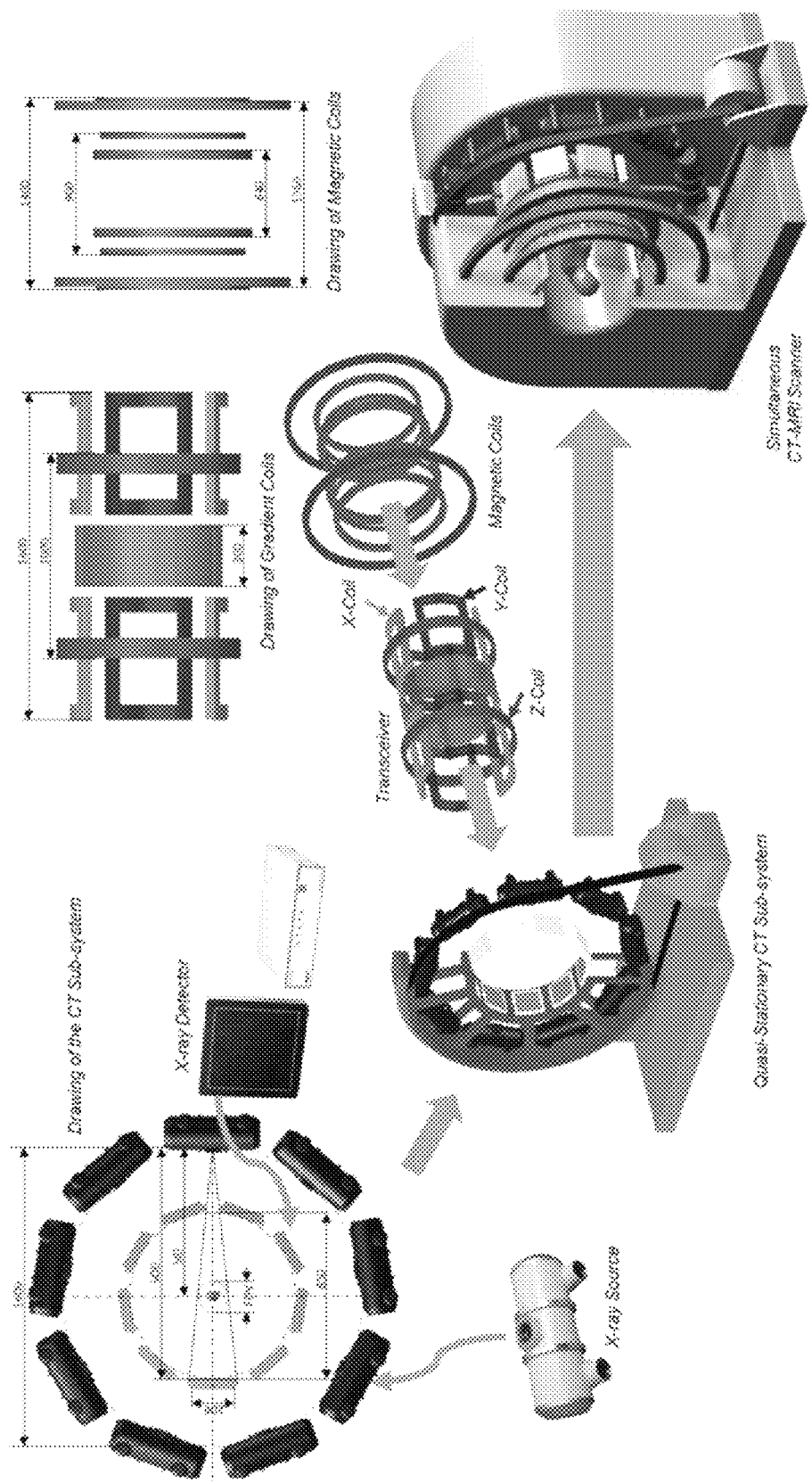
FIG. 19 shows a schematic view of a simultaneous CT-MRI scanner according to an embodiment of the subject invention.

FIG. 19 shows a schematic view of a simultaneous CT-MRI scanner according to an embodiment of the subject invention, including a breakdown of components and some possible dimensions. With the use of superconducting magnets, the clinical magnetic field strength can be achieved for uncompromised MRI performance (see also, Wang et al., Toplevel design of the first CT-MRI scanner, in Proceedings of The 12$^{th}$ International Meeting on Fully Three-Dimensional Image Reconstruction in Radiology and Nuclear Medicine, 2013, pp. 150-153; which is hereby incorporated by reference herein in its entirety). Though dimensions are shown in FIG. 19, these are for exemplary purposes only and should not be construed as limiting.

Based on the interior tomography oriented design, the peripheral magnetic field can be decreased rapidly (<0.5 Tesla) so as not to interfere with CT components significantly, and the static/quasistatic CT data acquisition system may not impose any substantial interference to the MRI process. Therefore, MRI image distortion may not be a problem in principle. To address conflicting space requirements by CT and MRI as well as suppress electromagnetic interference between CT and MRI for a simultaneous CT-MRI scanner, both CT and MRI can first be interiorized. A stationary multisource CT architecture with X-rays targeting a ROI can be used. Because the CT components stand still during data acquisition, the electromagnetic shielding can be greatly simplified. The physical complications can be handled using the same or similar techniques developed for X-ray/MRI. Correlation between CT and MRI datasets can be utilized to improve image quality. Superconducting design can be capable of offering clinically useful CT and MRI performance metrics.

In an embodiment, the CT-MRI instrumentation can target a relatively centralized ROI. Then, the extension from a centralized to a peripheral ROI can be attempted. There are multiple schemes to achieve this versatility. For example, a transversely elongated field of view could be used to accommodate the patient placement. Also, a local magnetic field can be developed that can be deflected using a superconducting technology and an adaptive X-ray beam collimation. Also, the CT setup can be either quasi-stationary or stationary. While the design in FIG. 19 is feasible to rotate X-ray imaging chains slightly between MRI acquisitions to cover more projection angles (as indicated by the belt in the bottom-right portion of FIG. 19), the heart motion can be utilized via biomechanical modeling and deformable matching based imaging in the ideal case of a stationary gantry with the sinogram limited to few views (e.g., 10 views or less).

Figure 20A:
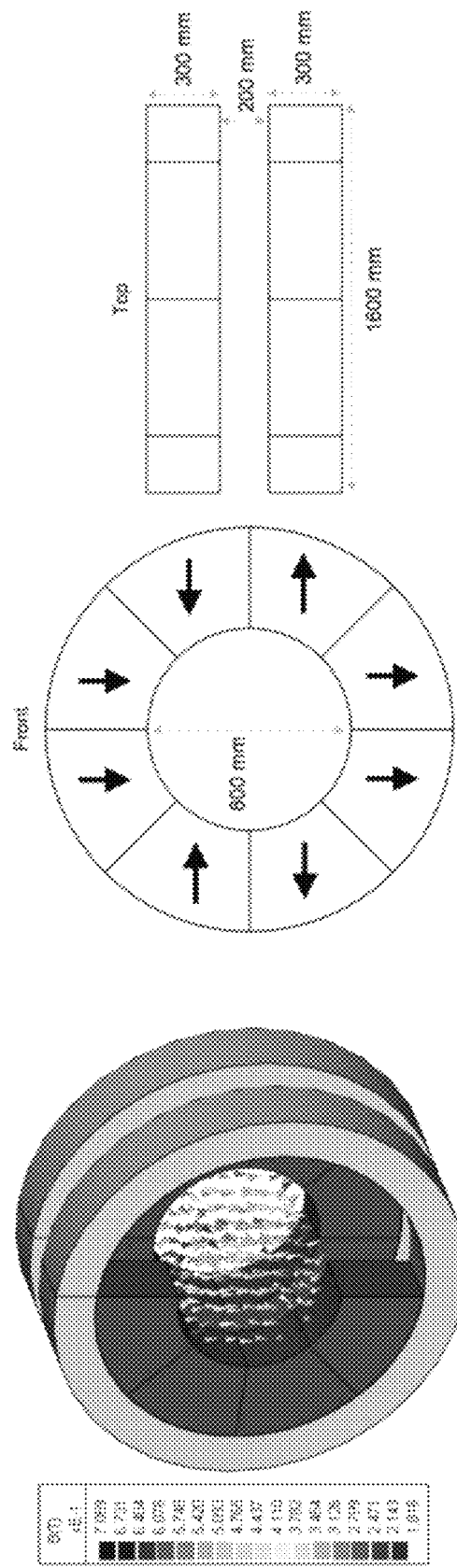
FIG. 20a shows a pair of donut-shaped magnets that can be used in a simultaneous CT-MRI scanner according to an embodiment of the subject invention.
Figure 20B:
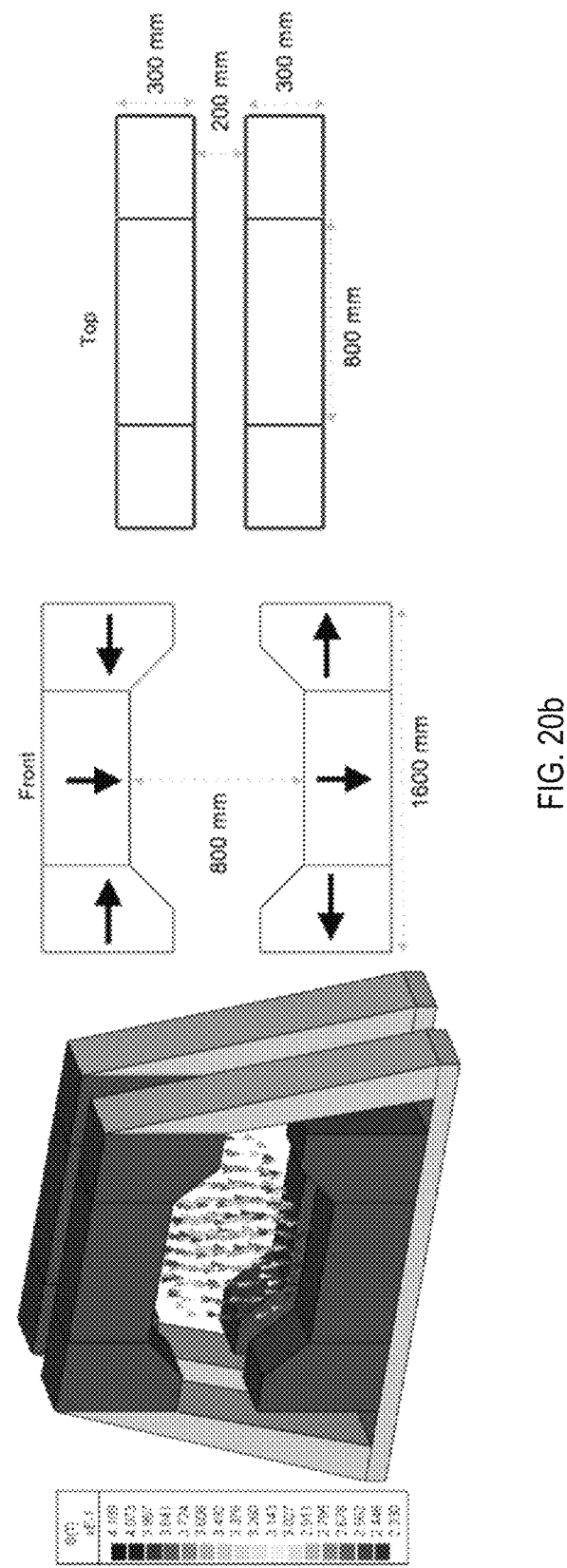
FIG. 20b shows a pair of hexagonal magnet arrays that can be used in a simultaneous CT-MRI scanner according to an embodiment of the subject invention.

FIG. 20a shows a pair of donut-shaped magnets that can be used in a simultaneous CT-MRI scanner according to an embodiment of the subject invention. Also, FIG. 20b shows a pair of hexagonal magnet arrays that can be used in a simultaneous CT-MRI scanner according to an alternative embodiment of the subject invention. In each of FIGS. 20a and 20b, the left side shows a 3-dimensional perspective view, the center section shows a cross-sectional side view, and the right side shows a top view. Though dimensions are shown in FIGS. 20a and 20b, these are for exemplary purposes only and should not be construed as limiting.

In a more cost-effective approach, permanent magnets can be used to replace superconducting magnets for simultaneous CT-MRI (e.g., in the designs shown in FIGS. 20a and 20b). The material for permanent magnets can be, for example, NdFeB (e.g., NdFeB 45 MGOe sintered). Referring again to FIG. 20a, a pair of donut-shaped permanent magnets can form a regionally uniform magnetic field (e.g., of about 0.35 T) and leave room for a CT gantry. The imaging parameters can include, for example, about 10 centimeters (cm) field of view, about 0.5 millimeters (mm) CT and MRI resolution (MRI resolution can be presumably enhanced with the associated CT data), and 1 CT-MRI scan/s in a continuous working mode (i.e., to be able to deliver hybrid images over a ROI or a volume of interest (VOI) every second). Electromagnetic interfering CT and MRI components can be easily shielded, which would otherwise be susceptible to electromagnetic interference. To construct a cost-effective background magnetic field, Halbach technology can be used in collaboration with low-field magnetic imaging. Referring again to FIG. 20b, a pair of hexagonal rings can be used to accommodate a patient and provide a gap for CT hardware. The hexagonal design can yield a magnetic field of, for example, about 0.3 T between the ring arrays. With appropriate shielding, shimming, and further refinements, the homogeneous field strength around the center of the magnet arrays can be brought up to about 0.5 T or more. The permanent magnets in any design can be upgraded to superconducting counterparts, for example, with a magnetic field of 1.5-3 T or more.

In an embodiment, an edge-guided dual-modality image reconstruction approach can be used. The key can be to establish a knowledge-based connection between the datasets in four steps: (1) image segmentation; (2) image initialization; (3) CT reconstruction; and (4) MRI reconstruction. One imaging modality can be significantly helped by the other imaging modality, even with highly under-sampled data. Generally speaking, such a synergistic CT-MRI reconstruction can be clinically beneficial. First, CT image noise and radiation dose can be reduced with correlative MRI data. Also, MRI spatial and temporal resolution may be improved with CT data. Furthermore, while CT-based motion mapping guides MRI reconstruction, MRI tagging information refines CT motion estimation.

Figure 21:
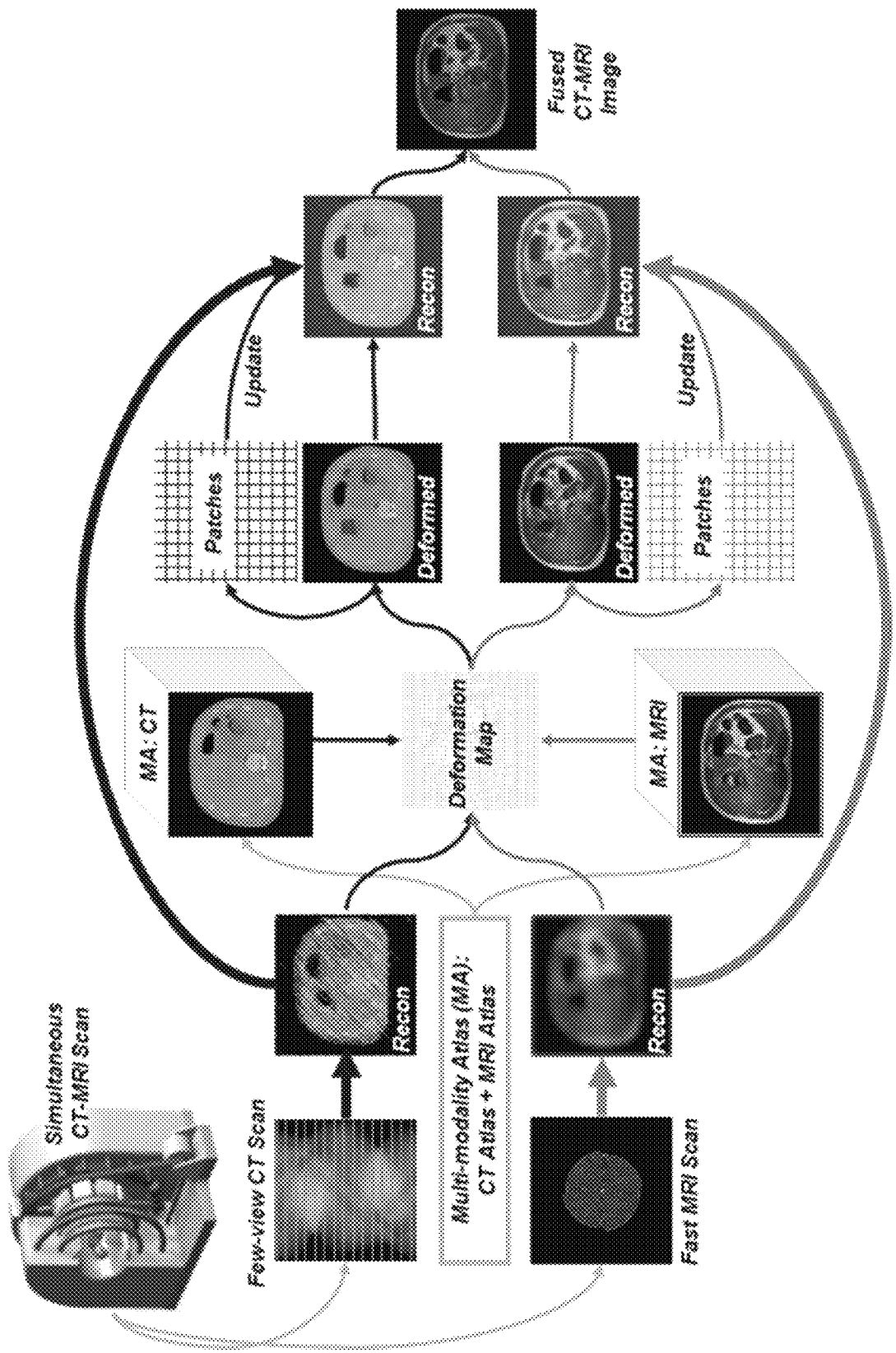
FIG. 21 shows a flowchart for simultaneous CT-MRI image reconstruction according to an embodiment of the subject invention.

FIG. 21 shows a flowchart for simultaneous CT-MRI image reconstruction according to an embodiment of the subject invention. Referring to FIG. 21, in an embodiment, a pair of co-registered CT and MRI atlases can be used to aid in the reconstruction process. Prior knowledge of CT and/or MRI results and inter-modality synergy can be utilized for reduced noise and biases. Multiple iterative loops can be performed.

Referring again to FIG. 21, in an embodiment, the overall framework for joint CT-MRI image reconstruction (or general multimodality image reconstruction) can be to perform image estimation for each modality based on a current scan and a corresponding high-quality atlas. For this purpose, a unified deformation map can be jointly constructed from CT and MRI scans as well as CT and MRI atlases. With this deformation map, estimated CT and MRI images can be generated as prior knowledge. Other image estimation methods can also be possible. For example, a CT image (or a MRI image) can be estimated from the corresponding high-quality MRI (or CT) image using a CT-MRI atlas. In this case, with the high-quality MRI image, a displacement field can be computed to deform an MRI image in the atlas into the target MRI image. Then, the same displacement field can be applied to deform the corresponding CT image in the atlas into an estimated CT image. Similarly, an MRI image can be estimated from a given target CT image. These estimated images can be used to regularize the joint CT-MRI image reconstruction. One of these powerful techniques is locally linear embedding (LLE), which can be adapted to reduce image noise or bias. According to LLE theory, each image patch from an imaging modality can be linearly represented in terms of nearby K most-similar patches (which is in the same spirit of known nonlocal mean methods but can capture more structural information). For example, it is feasible to find a LLE at any anatomical location for a deformed MRI image from the atlas. Then, this LLE for the deformed atlas image can be applied to a current MRI image as a noise/bias filter. Similarly, a current CT image can be improved via LLE. Although FIG. 21 shows global joint CT-MRI reconstruction, joint interior CT-MRI reconstruction can be done as long as interior CT and interior MRI algorithms replace the corresponding global reconstruction algorithms. In the case of an interior CT-MRI scan, an individualized patient surface contour can be captured using an optical imager for the associated atlas deformation.

Estimated CT and MRI images, as well as atlas-based embedding structures can be all incorporated into a single object function to facilitate a unified CT-MRI reconstruction.

In the case of cardiac imaging, both CT and MRI images should be used to meet demanding requirements for spatial, contrast, and temporal resolutions. However, there is a conflict between a stationary CT architecture and sufficient projections through a cardiac ROI. In other words, about 10 projections can acquired in parallel without mechanical motion of the CT subsystem, but this limited number of projections is generally not enough for excellent image quality. This challenge can be addressed by utilizing cardiac motion itself. Specifically, ventricular torsion can be taken advantage of to increase the number of X-ray projections of the stationary multisource CT subsystem. Left ventricular (LV) torsion refers to myocardial motion and deformation during systole and diastole. The cardiac myocytes are arranged in a spiral network from the apex to the base. As they contract during systole, the heart undergoes a twisting motion, which is largely due to opposite rotational contractions in the base and apex. Echo-tracking ultrasound imaging has shown rotation angles of 7.96°±1.57° and 9.49°±1.71° in the base and apex, respectively. ECG-gated acquisition protocols and/or tagged MRI would allow for sophisticated cardiac biomechanical modeling and model based image reconstruction that is equivalent to use of an increased number of views of the heart. This torsion is more complicated than a simple rotation as there are some linear displacements during a cardiac cycle. Nonetheless, an accurate and real-time depiction of the heart at any single time point can be obtained with imaging techniques as described herein.

A CT-MRI scanner can acquire MRI and CT measurements of the subject simultaneously. CT and MRI subsystems can be seamlessly integrated for local reconstruction, enabled by the generalized interior tomography principle (see also Wang et al., The meaning of interior tomography, Phys. Med. Biol., vol. 58, pp. R161-R181, 2013; which is hereby incorporated by reference herein in its entirety). The CT components can be made quasi-stationary with X-ray sources and detectors distributed face-to-face along a circle to overcome space limitations and electromagnetic interference. Given the geometrical constraints, the number of X-ray sources may be limited and can represent a "few-view" reconstruction problem. A pair of magnets or magnet arrays can be used to define a relatively small homogeneous magnetic field in the gap between the magnets or magnet arrays for the MRI subsystem; this, in combination with open configuration, allows room for the CT subsystem. The pair of magnet or magnet arrays can be, for example, donut-shaped or hexagonal, though embodiments are not limited thereto (see also FIGS. 20a and 20b).

In an embodiment of a CT-MRI scanner, the CT imaging process can be the same as for the current commercial CT systems except that the X-ray sources are fixed during a scan, but they could be rotated between scans if needed. Hence, the CT imaging model can be expressed as $$Mu_{CT} = f \qquad (1)$$

where $u_{CT}$ describes an object to be imaged in terms of linear attenuation coefficients, M is a system matrix, and f is line integral data after preprocessing.

In the MRI subsystem, the imaging model can also be similar to the conventional model, expressed as $$RFu_{MRI}=g \quad (2)$$

where $u_{MRI}$ describes the same object but in terms of MRI parameters related to T1, T2, proton density, etc. F denotes the Fourier transform, R is a sampling mask in the k-space, and g is data.

In the CT-MRI scanner, CT and MRI data can be spatially and temporally registered. Alternatively, separately acquired CT and MRI scans can be fused to simulate a simultaneous acquisition. This CT-MRI duality is the base of many embodiments of the simultaneous CT-MRI image reconstruction strategy described herein.

Given appropriate spatial and temporal co-registration of CT and MRI images, their features can be physically correlated despite their inherently different imaging characteristics. The physical correlation and image compressibility can be collectively utilized via CS, for example, using the PRISM method which was adapted for various applications (Wang et al., Towards omni-tomography—Grand fusion of multiple modalities for simultaneous interior tomography, PloS One, vol. 7, p. e39700, 2012). However, PRISM and similar CS methods capture correlation as low rank characteristics that are rather general but not very specific. Most other known methods cannot address the joint image reconstruction problem over imaging modalities. Embodiments of the subject invention can use SC to reflect local similarity more specifically and more effectively for joint multimodality image reconstruction.

Figure 1B:
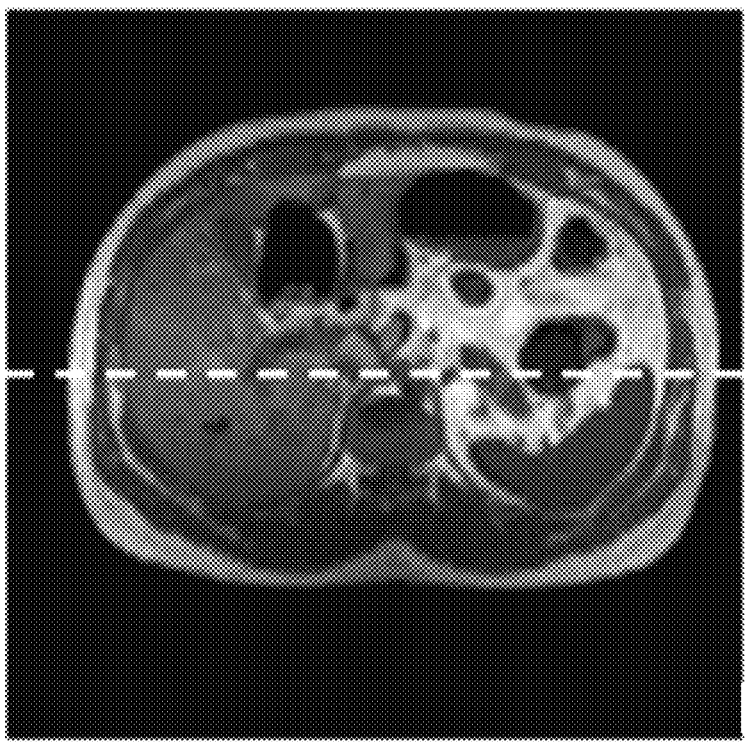
FIG. 1b shows a magnetic resonance imaging (MRI) image of the human abdomen of FIG. 1a, normalized into [0,1].
Figure 1C:
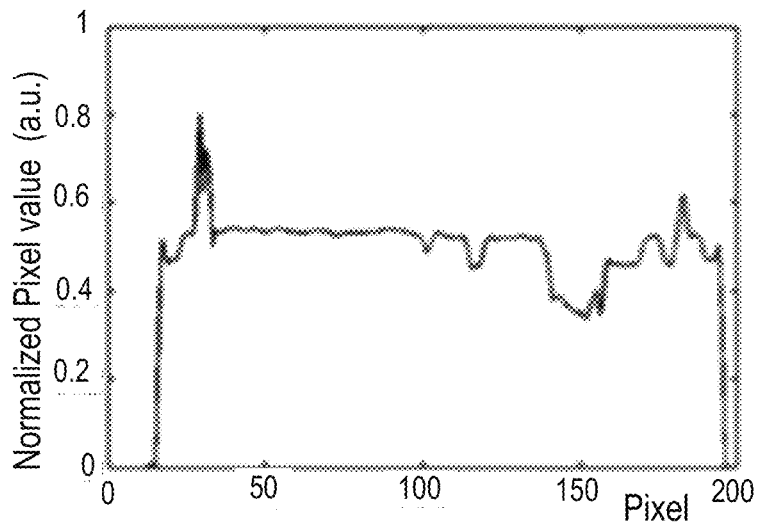
Figure 1D:
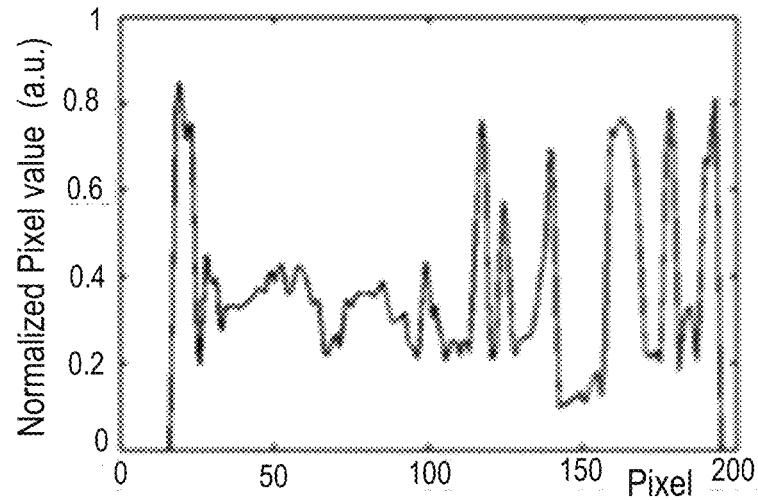
FIG. 1d shows a line profile along the dotted line of FIG. 1b.
Figure 1E:
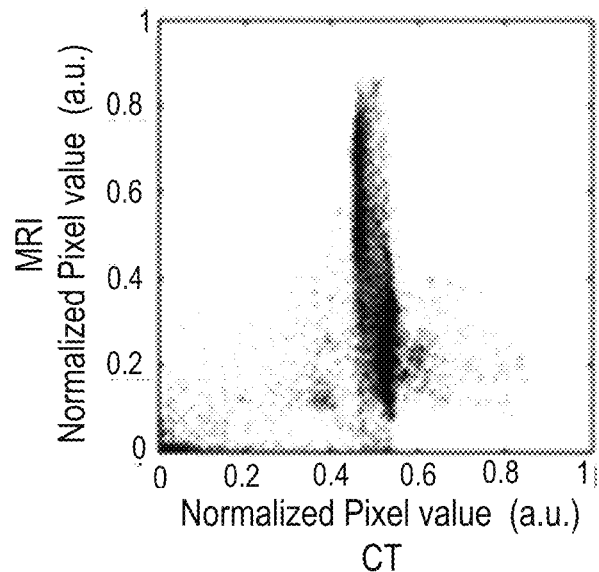
FIG. 1e shows a joint histogram of FIGS. 1a and 1b.

FIGS. 1a and 1b show a CT image and an MRI image of a human abdomen, respectively, both normalized into [0,1]. FIGS. 1c and 1d show line profiles along the dotted line of FIG. 1a and the dotted line of FIG. 1b, respectively, and FIG. 1e shows a joint histogram of FIGS. 1a and 1b. Referring to FIGS. 1a-1e, the reconstructed pixel values are not well correlated, as suggested by FIGS. 1c-1e. Nevertheless, their structural boundaries are quite consistent, and different human beings share very similar anatomic structures.

A principal concept for utilization of CT-MRI image correlation is to pair their local structures in intrinsic corresponding relations, which is a natural coupling of relevant image features. In many embodiments, the connection between CT and MRI image features is maintained in paired CT-MRI patches. They can be generated from one-to-one corresponding CT and MRI image datasets. Given such a CT-MRI dataset, one-to-one corresponding patches can be extracted.

First, prior CT and MRI images can be deformed according to currently reconstructed CT and MRI images. The deformed CT-MRI images can be much closer to target CT and MRI images under reconstruction. This step will be further described herein.

Next, bidirectional CT and MRI image estimations can be performed using the SC method. The SC method is inspired by the locally linear embedding (LLE) theory, in which each data point in a high-dimensional space can be linearly represented in terms of the surrounding data points (see also Roweis et al., "Nonlinear dimensionality reduction by locally linear embedding, Science, vol. 290, pp. 2323-2326, 2000; which is hereby incorporated by reference herein in its entirety). Specifically, in the SC method, each patch is treated as a point in a high-dimensional space. Any patch p, in given images can be linearly expressed with its similar patches $p_{*,i}$. Involved weights $\{w_{*,i}\}$ can be determined by a Gaussian function, similar to those used in the nonlocal mean filtering:

$$w'_{*,i} = \exp(-\|p_* - p_{*,i}\|_2^2/h^2) \text{ and } w_{*,i} = w'_{*,i} \Big/ \sum_i^K w'_{*,i}, \quad (3)$$

where h is an empirical value that controls contributions of involved patches, and K is the number of surrounding data points.

The fundamental principle of the SC method of embodiments is based on the LLE theory, and the corresponded CT image patch $p_{CT}$ can be linearly approximated with the associated patches in CT dataset $T_{CT}$ and the same weighting factors $\{w_i\}$, formulated as $p_{CT}$ and $\approx \sum_i^k w_i\, p_{CT,i}$, and $p_{CT,i} \in T_{CT}$, and $p_{CT,i} \neq p_{CT}$, as that for $p_{MRI}$ in MRI dataset $T_{MRI}$. Thus, with the weights $\{w_{*,i}\}$ and the one-to-one correspondence in extracted patch pairs, CT and MRI images are correlated. To implement bidirectional CT and MRI image estimations, a selection vector $\beta_i$ can be applied to both CT and MRI datasets $$\min_{\beta_i} \left\| p_{MRI} - \sum_i w_i T_{MRI}\beta_i \right\|_2^2 + \left\| p_{CT} - \sum_i w_i T_{CT}\beta_i \right\|_2^2, \quad (4)$$

where $w_i$ equals the average of CT and MRI weightings calculated according to Equation (3), $w_i=(w_{CT,i}+w_{MRI,i})/2$, $\beta_i$ identifies surrounding high-dimensional data points. Thus, CT and MRI patches are linked based on prior CT-MRI datasets by sharing the same selection vector and weights. Given a CT image, its corresponding MRI image can be predicted based on prior CT-MRI patches and representation weights. The same scheme can be also applied on the mapping from MRI image to CT image. Here, the optimization of Equation (4) is empirically implemented: first, find ten K-nearest data points in CT and MRI spaces; then, compute the objective function—Equation (4)—with the first step results; and finally, choose CT and MRI patches for the minimum value of Equation (4).

The SC method of embodiments utilizes the fact that a corresponding CT patch and MRI patch are correlated via $T_{CT\text{-}MRI}$ in terms of patch pairs. This principle has been demonstrated to be valid in (see, e.g., the examples). An example of the random tests is demonstrated in FIG. 2, where given an MRI patch $p_{MRI}$ the corresponding CT patch $$p\frac{est}{CT}$$

can be estimated using a pre-trained image pair table $T_{CT\text{-}MRI}$, and the resultant $$p\frac{est}{CT}$$

is very close to the true CT patch $$p\frac{true}{CT}.$$

FIG. 3 shows the estimation results using the SC method from given MRI images. The ground truth CT images and input MRI images are in the first and second columns, respectively.

Figure 2:
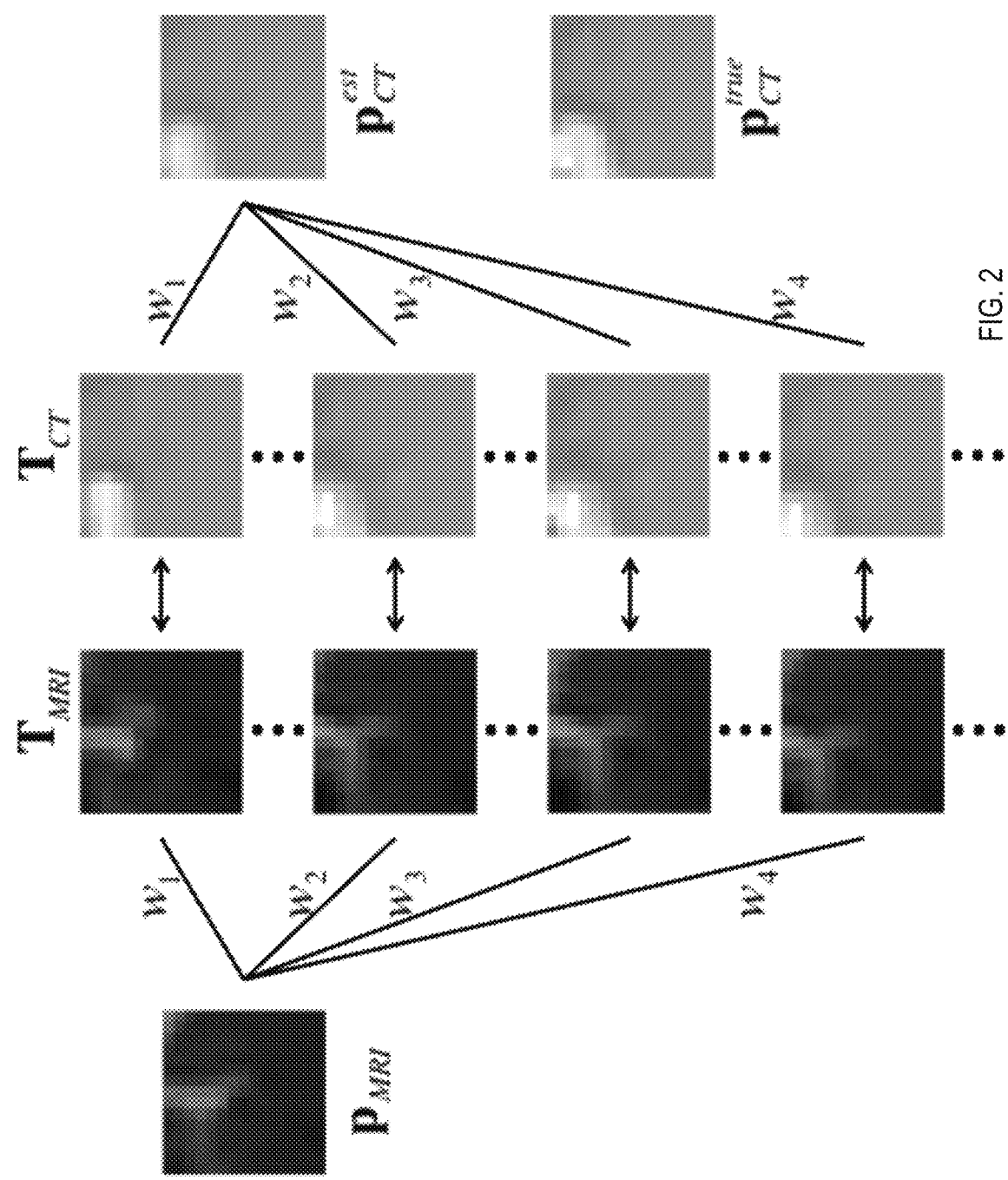
FIG. 2 shows structural coupling (SC) for image estimation.

In detail, FIG. 2 shows SC for image estimation. Referring to FIG. 2, any given MRI patch $p_{MRI}$ can be linearly represented with similar patches in $T_{MRI}$. Then, the corresponding CT patch $p_{CT}$ can be linearly represented by the corresponding patches in $T_{CT}$ with the same weighting factors $\{w_i\}$ as used for representing $p_{MRI}$.

Figure 3A:
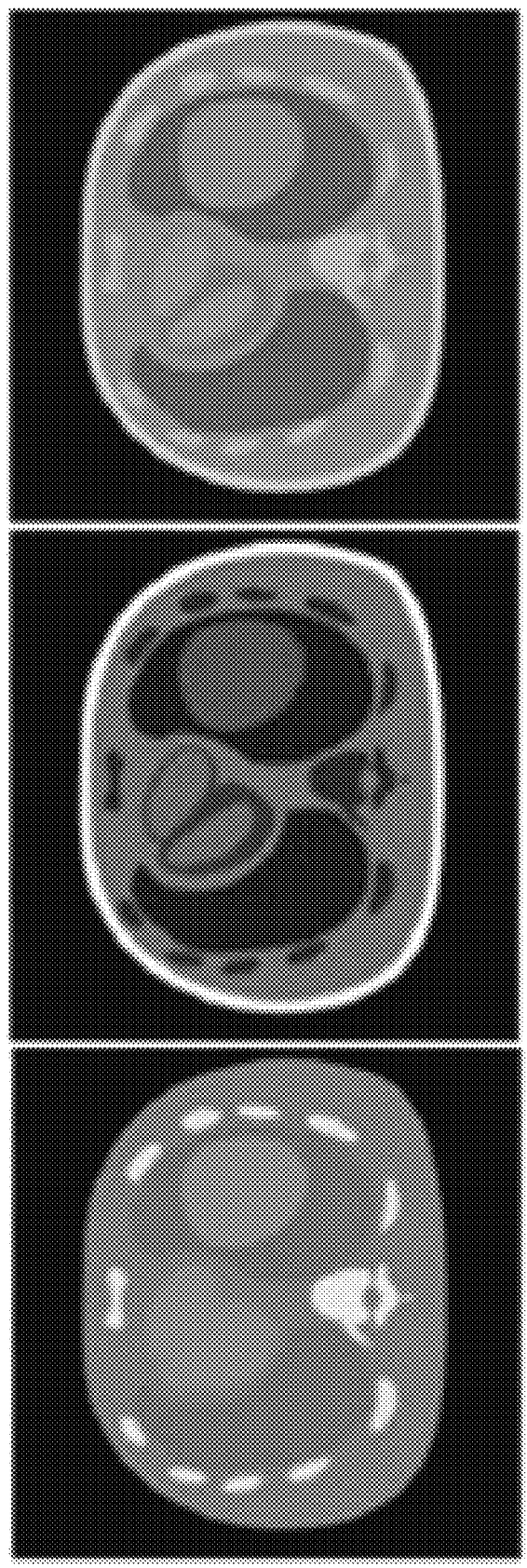
FIG. 3a shows a ground truth CT image (left), a ground truth MRI image (center), and a registration result image (right) for a modified NCAT phantom (mNCAT).
Figure 3B:
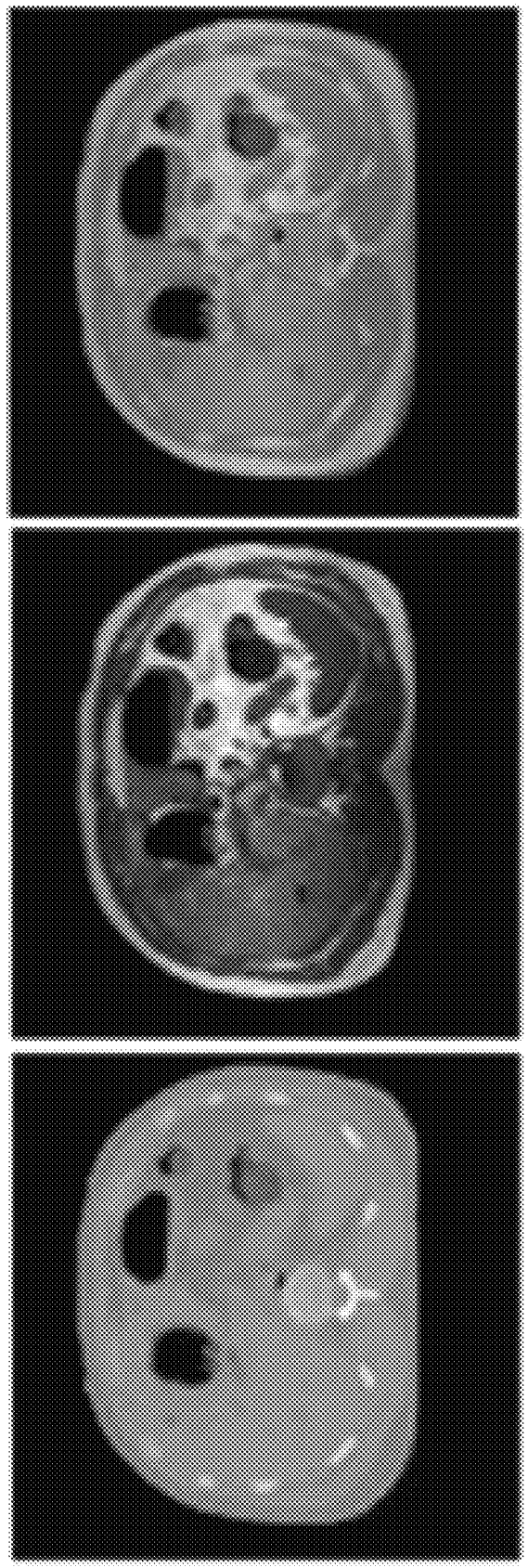
FIG. 3b shows a ground truth CT image (left), a ground truth MRI image (center), and a registration result image (right) for a visible human project phantom (VHP).
Figure 3C:
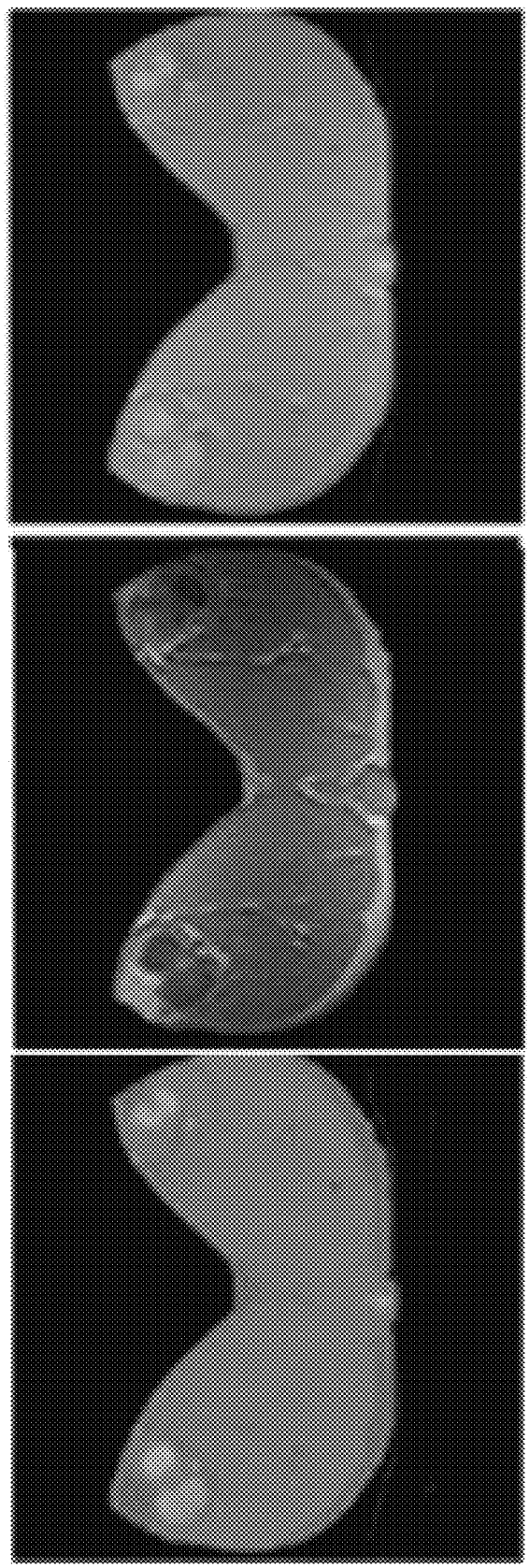
FIG. 3c shows a ground truth CT image (left), a ground truth MRI image (center), and a registration result image (right) for a porcine sample.

FIG. 3a shows a ground truth CT image (left), a ground truth MRI image (center), and a registration result image (right) for a modified NCAT phantom (mNCAT). FIG. 3b shows a ground truth CT image (left), a ground truth MRI image (center), and a registration result image (right) for a visible human project phantom (VHP). FIG. 3c shows a ground truth CT image (left), a ground truth MRI image (center), and a registration result image (right) for a porcine sample.

It should be noted that weighting factors $\{w_i\}$ defined in Equation (3), and used in Equation (4) are not the same results as that obtained by the classic LLE theory. One advantage of the methods described herein is that they measure weight by the Euclidean distance from the reference patch $p_{MRI}$, and guarantee that $\{w_i\}$ is positive and in a proper range. In the CT-MRI reconstruction methods of many embodiments of the subject invention, Equation (4) plays a key role in bidirectional image estimation by sharing the same selection vector $\beta_i$ and $\{w_i\}$ determined from both MRI and CT sides.

CS has been proven effective for most tomographic modalities. CS theory seeks a "sparse" solution for an underdetermined linear system. Total variation (TV) is a widely used sparsifying transformation for CS-based CT and MRI reconstruction (see also Rudin et al., Nonlinear total variation based noise removal algorithms, Phys. D, Nonlinear Phenom., vol. 60, pp. 259-268, 1992; and Chambolle, An algorithm for total variation minimization and applications, J. Math. Imag. Vis., vol. 20, pp. 89-97, 2004; both of which are hereby incorporated by reference herein in their entireties). The TV based CT and MRI reconstruction algorithms are, respectively, written as $$\min_{u_{CT}} \|u_{CT}\|_{TV} \quad \text{s.t.} \quad Mu_{CT} = f \quad (5)$$

and $$\min_{u_{MRI}} \|u_{MRI}\|_{TV} \quad \text{s.t.} \quad RFu_{MRI} = g \quad (6)$$

where $\|\cdot\|_{TV}$ represents the TV transformation.

In simultaneous CT-MRI reconstruction, CT and MRI datasets can be assumed to be spatially and temporally registered. These datasets can be separately reconstructed, and then combined. Intuitively, a joint CT-MRI image reconstruction framework should offer significantly better image quality than individual reconstructions because there are substantial correlations and complementary features between CT and MRI images.

There are two main steps in the simultaneous CT-MRI reconstruction according to many embodiments of the subject invention: patch-based image estimation; and guided image reconstruction. They can be iteratively and alternatively performed. The image reconstruction can first be started with regular CS-based CT and MRI reconstructions as suggested in Equations (5) and (6). Then, in the image estimation step, the reconstructed CT and MRI images can be set as the basis to predict their MRI and CT counterparts with the SC method. In the reconstruction step, the estimated CT and MRI results can be used to guide CT and MRI reconstructions, respectively. Thus, individual CT and MRI reconstructions can be linked together to guide the composite reconstruction synergistically.

Figure 4:
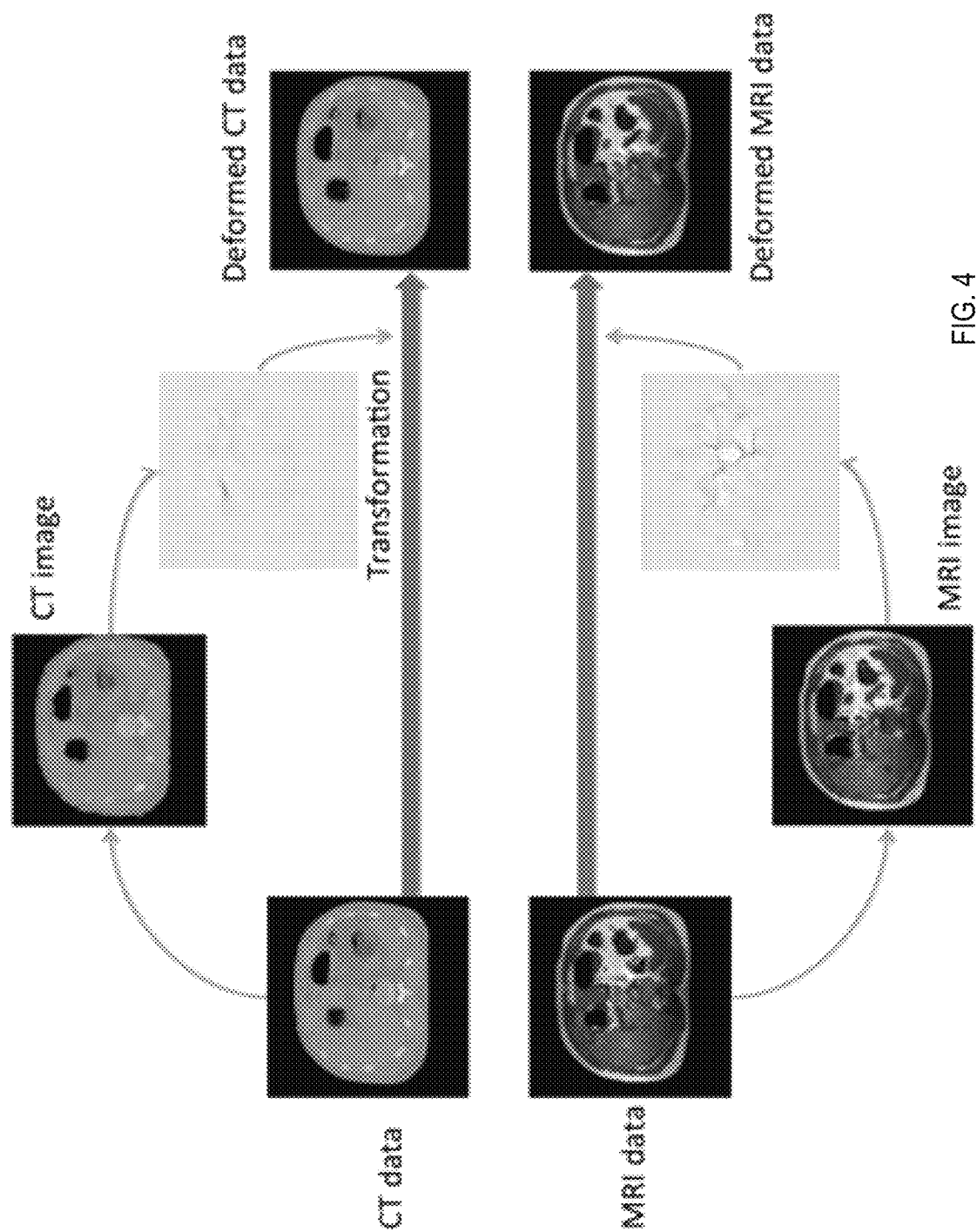
FIG. 4 shows a diagram of examples of CT and MRI datasets deformation.

In the image reconstruction, prior CT-MRI image patches can serve as a bridge to connect the two modalities. The SC method can perform the mapping between reconstructed CT and MRI images. In the SC method, prior CT and MRI datasets can first be deformed according to the given reconstructed CT and MRI images, as shown in FIG. 4. The newly deformed CT-MRI datasets can be much closer to target CT and MRI images in reconstruction. Then, corresponding image patches can be extracted from the deformed prior CT and MRI datasets. Subsequently, both reconstructed CT and MRI images can be decomposed into patches and updated according to the paired image patches that share the same weighting factors $\{w_i\}$ and the same selection vector $\beta_i$ in the deformed table $T_{CT-MRI}$. This process can be performed by finding the most similar patches and refining intermediate image patches via linear embedding, as described above. In the guided image reconstruction, estimated CT and MRI images, which can be based on previously reconstructed MRI and CT images, can be used to regularize their images in each individual modality reconstruction. They can be written as $$\min_{u_{CT}} (1-\alpha)\|u_{CT}\|_{TV} + \alpha\|u_{CT} - u_{CT}^{est}\|_{TV} \quad \text{s.t.} \quad Mu_{CT} = f \quad (7)$$

and $$\min_{u_{MRI}} (1-\alpha)\|u_{MRI}\|_{TV} + \alpha\|u_{MRI} - u_{MRI}^{est}\|_{TV} \quad \text{s.t.} \quad Fu_{MRI} = g, \quad (8)$$

where $$u_{CT}^{est} \text{ and } u_{MRI}^{est}$$

are estimated images using the SC method according to the corresponding CT and MRI images. Equations (7) and (8) are well-posed convex optimization problems and can be effectively solved using the Split-Bregman method (see also Xi et al., United iterative reconstruction for spectral computed tomography, IEEE Trans. Med. Imag., vol. 34, no. 3, pp. 769-778, Mar. 2015; and Goldstein et al., The split Bregman method for L1-regularized problems, SIAM J. Imag. Sci., vol. 2, pp. 323-343, 2009; both of which are hereby incorporated herein by reference in their entireties).

TABLE I

WORKFLOW FOR SIMULTANEOUS CT-MRI IMAGE RECONSTRUCTION

| Inputs | CT projection data f and MRI k-space data g |
|---|---|
| Reconstruction: | 1. Reconstruct a CT image $u_{CT}$ from f by (5);<br>2. Reconstruct an MRI image $u_{MRI}$ from g by (6);<br>3. k = 0;<br>4. Loop until meeting the stop criteria<br>5. Transform CT-MRI datasets $T_{CT\text{-}MRI}$ by given $u_{MRI}$ and $u_{CT}$;<br>6. Estimate the corresponded CT-MRI image $u_{CT}^{est}$ and $u_{MRI}^{est}$ according to $u_{MRI}$ $u_{CT}$ aided by $T_{CT\text{-}MRI}$ using the SC method (see Table II);<br>7. Reconstruct the CT image with $u_{CT}^{est}$ and f by (7);<br>8. Reconstruct the MRI image with $u_{MRI}^{est}$ and g by (8);<br>9. k = k + 1;<br>10. end |

Overall, the simultaneous CT-MRI image reconstruction approach can be formulated as follows:

$$\min_{(u_{CT}, u_{MRI}, \beta)} \|u_{CT}\|_{TV} + \lambda \|u_{MRI}\|_{TV} + \quad (9)$$

$$\gamma \sum_j \left( \left\| E_j u_{MRI} - \sum_i w_i T_{MRI} \beta_{j,i} \right\|_2^2 + \left\| E_j u_{CT} - \sum_i w_i T_{CT} \beta_{j,i} \right\|_2^2 \right)$$

$$\text{s.t. } M u_{CT} = f, \, RF u_{MRI} = g$$

where E is an operator to extract patches from an image, and β determines which patch is selected for linear approximation by assigning appropriate weighting factors $\{w_i\}$. It is underlined that the same weighting vector $\{w_i\}$ and the same selection vector β are used for both CT and MRI patches that reflect the physical correlation between the two images in Equation (9). Table I presents the workflow for simultaneous CT-MRI reconstruction according to an embodiment. Table II presents the workflow for SC-based CT and MRI image estimation.

In practice, SC can be implemented using the hashing method to accelerate the patch searching process (see also Xi et al., United iterative reconstruction for spectral computed tomography, IEEE Trans. Med. Imag., vol. 34, no. 3, pp. 769-778, Mar. 2015). For example, the hashing-based SC step can be implemented in MATLAB (Math-Works, Massachusetts, USA) or can be accelerated using a high-efficiency programming language, such as C++ (e.g., on a parallel computing framework such as CUDA, because the patch wise operations are naturally parallel).

Simultaneous CT-MRI reconstruction systems and methods of the subject invention are superior to individual TV-based reconstructions. A main reason for such improvement in image quality is utilization of physical correlation between CT and MRI images. The physical correlation can regularize and enhance the imaging performance of either CT or MRI (assuming accurate co-registration of involved datasets); and the synergy is more significant in challenging cases such as few-view CT and low-field MRI. The CT and MRI image registration error can degrade the CT image quality significantly, but has a diminished effect on the MRI image quality.

TABLE II

WORKFLOW FOR SC-BASED CT AND MRI IMAGE ESTIMATION

| Input | MRI image $u_{MRI}$, CT image $u_{CT}$, the number of similar patches K |
|---|---|
| Data transformation: | According to FIG. 4, deform CT and MRI datasets based on given CT and MRI images.<br>1. Decompose $u_{CT}$ into patches $p_{CT}^j = E_j u_{CT}$; |
| Estimation: | 2. Decompose $u_{MRI}$ into patches $p_{MRI}^j = E_j u_{MRI}$;<br>3. Optimize (4) by finding K-best suitable patches $\{p_{CT,i}^j\}$ and $\{p_{MRI,i}^j\}$, and their weights $\{w_i\}$ in $T_{CT}$ and $T_{MRI}$ to represent $p_{CT}^j$ and $p_{MRI}^j$;<br>4. Estimate CT and MRI image patches with the corresponded CT and MRI image pairs in $T_{CT\text{-}MRI}$ and new weights $\{w_i\}$,<br><br>$$p_{new,CT}^j \approx \sum_i^K w_i p_{CT,i}^j \cdot p_{new,MRI}^j \approx \sum_i^K w_i p_{MRI,i}^j;$$<br><br>5. Estimate the corresponded CT image with $p_{new,CT}^j$,<br><br>$$u_{CT}^{est} = \left( \sum_j E_j^T E_j \right)^{-1} \left( \sum_j E_j^T p_{new,CT}^j \right).$$<br><br>6. Estimate the corresponded MRI image with $p_{new,MRI}^j$,<br><br>$$u_{MRI}^{est} = \left( \sum_j E_j^T E_j \right)^{-1} \left( \sum_j E_j^T p_{new,MRI}^j \right).$$ |

Although TV is discussed herein as being used for image sparseness, more advanced sparsifying transformations, such as DL can be used and may yield better image quality. In Table I, α was used to balance the regularization effects of TV in an image and TV between images in Equations (7) and (8), and was empirically set to 0.5 in Example 1 below. However, the iteratively estimated image should be increasingly closer to the true image, and the distance between the reconstructed and estimated images should gradually decrease. Thus, the parameter α can be adaptively set with respect to the iteration index for better image quality.

In simultaneous CT-MRI reconstruction according to embodiments of the subject invention, the SC method can link CT and MRI image reconstructions based on physical correlations in the form of paired image patches. The physical correlation can be important to improve the performance of each individual imaging modality. Thus, the size, amount, and type of these patches can be important. If the patch size were too small, there would be insufficient local features for close coupling of different modalities, and the image estimation workflow (see Table II) would be degraded. On the other hand, if the patch size were too large, it would be difficult to approximate a patch accurately via a linear combination of its K-most similar patches. Other important factors are the amount and types of patches that determine whether the K-most similar patches are powerful enough to represent a given patch. However, this does not imply that a larger number of patches is always preferred, because a longer image patch table will dramatically increase computational complexity.

In many embodiments, simultaneous CT-MRI image reconstruction uses SC and CS techniques as key components. A simultaneous CT-MRI scanner can give CT and MRI datasets that are spatially and temporally co-registered. Alternatively, separately acquired CT and MRI datasets can be preprocessed and retrospectively registered as inputs to the reconstruction framework. This retrospectively integrated CT-MRI reconstruction approach can improve studies acquired sequentially, when individual scans are separately acquired under suboptimal conditions due to technical limitations or patient issues (e.g., fast heart rate, unstable medical condition). The results in Example 1 have demonstrated that the performance of the CT-MRI reconstruction algorithm is superior to conventional decoupled CT and MRI reconstructions.

The reconstruction methodology described herein can be generalized to combinations of other tomographic modalities, such as SPECT-CT, PET-MRI, optical-MRI, and omni-tomography in general. ROI-oriented scanning, simultaneous data acquisition, and advanced image reconstruction, modeling and analysis for in vivo tomographic sampling, can have important applications such as those suggested in FIGS. 23a-23d.

Figure 23:
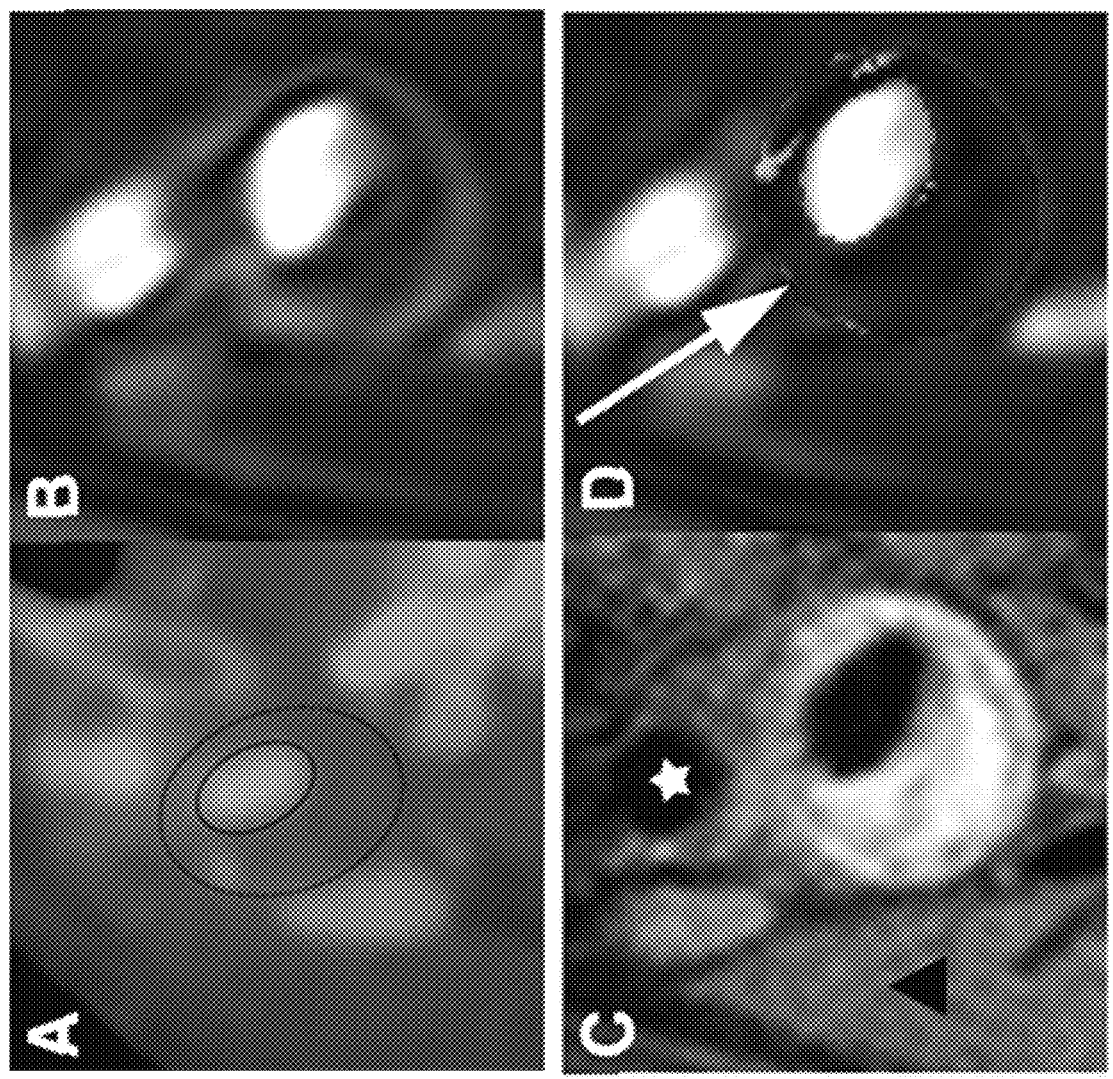
FIG. 23a shows a PET-CT scan of a transverse section of the carotid plaque from a 64-yr-old man.
FIG. 23b shows a dynamic contrast enhanced (DCE) MRI scan of a transverse section of the carotid plaque from a 64-yr-old man.
FIG. 23c shows a dynamic contrast enhanced (DCE) MRI scan of a transverse section of the carotid plaque from a 64-yr-old man.
FIG. 23d shows a dynamic contrast enhanced (DCE) MRI scan of a transverse section of the carotid plaque from a 64-yr-old man.

FIG. 23a shows a PET-CT scan of a transverse section of the carotid plaque from a 64-yr-old man, and FIGS. 23b-23d show DCE-MRI scans of the same transverse section of the carotid plaque. Referring to FIG. 23a, the lumen is delineated by the black line, and the plaque is delineated by the dashed black line. FIG. 23b shows an image six minutes after contrast injection, and FIG. 23c shows a T1-weighted turbo spin echo MRI. FIG. 23d shows parametric K-trans map overlaid on DCE-MRI. Voxel K-trans values are color-encoded from 0 to 0.2 $min^{-1}$. The lipid-rich necrotic core exhibits low K-trans values at the center of the plaque, and the highly vascularized adventitia (high K-trans values) at the outer rim (indicated by the arrow in FIG. 23d) is clearly visualized. The star in FIG. 23c denotes the external carotid artery, and the triangle in FIG. 23 denotes the sternocleidoid muscle. FIGS. 23a-23d are adapted from Truijman et al. (Combined 18F-FDG PET-CT and DCE-MRI to assess inflammation and microvascularization in atherosclerotic plaques, Stroke 44, 3568-3570, 2013).

The synergistic reconstruction strategy and novel fusion of tomographic imaging modalities not only takes advantage of complementary attributes from each modality but also potentially optimizes the results of any individual modality and leads to hybrid imaging that is time efficient, cost effective, and more importantly, superior in imaging performance for biomedical applications, such as dynamic contrast enhancement studies on cancer and cardiovascular diseases.

Embodiments of the subject invention allow for simultaneous acquisition of CT and MRI data (e.g., during dynamic contrast enhancement), and advantageously enables both modalities to provide contrast kinetic parameters, while limiting assumptions, intrinsic errors, and limitations of the modeling processes. This synergistic approach can lead to better characterization of the imaged tissues. Simultaneous CT-MRI imaging systems and reconstruction methods fill a major gap of modality coupling and represent a key step toward omnitomography, which is the integration of all relevant imaging modalities for systems biology and precision medicine.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The simultaneous reconstruction methods and processes described herein can improve performance of a combined CT-MRI scanner by drastically improving image quality, time efficiency, cost effectiveness, and imaging performance in general.

The subject invention includes, but is not limited to, the following exemplified embodiments.

Embodiment 1

A system for simultaneous computed tomography (CT)-magnetic resonance imaging (MRI), the system comprising:
 a CT subsystem for obtaining CT data;
 an MRI subsystem for obtaining MRI data;
 at least one processor; and
 a machine-readable medium, in operable communication with the CT subsystem, the MRI subsystem, and the at least one processor, having machine-executable instructions stored thereon that, when executed by the at least one processor, perform a method of reconstructing CT and MRI images, the method comprising:
 i) reconstructing a CT image $u_{CT}$ from the CT data;
 ii) reconstructing an MRI image $u_{MRI}$ from the MRI data;
 iii) setting an iteration step k=0;
 iv) transforming a CT-MRI dataset $T_{CT\text{-}MRI}$ by the $u_{CT}$ and $u_{MRI}$;
 v) estimating the corresponded CT-MRI image $$u\frac{est}{CT} \text{ and } u\frac{est}{MRI}$$

according to $u_{CT}$ and $u_{MRI}$ aided by the CT-MRI dataset $T_{CT\text{-}MRI}$;
 vi) reconstructing the CT image $u_{CT}$ with $$u\frac{est}{CT}$$

and the CT data;
vii) reconstructing the MRI image $u_{MRI}$ with $$u\frac{est}{MRI}$$

and the MRI data;
viii) setting k=k+1; and
ix) repeating steps iv)-viii) until meeting stop criteria, at which point the current $$u\frac{est}{CT}$$

is the reconstructed CT image and the current $$u\frac{est}{MRI}$$

is the reconstructed MRI image.

Embodiment 2

The system according to embodiment 1, wherein reconstructing a CT image $u_{CT}$ from the CT data comprises using the following equation:

$$\min_{u_{CT}} \|u_{CT}\|_{TV} \text{ s.t. } Mu_{CT} = f,$$

where M is a system matrix, f is the (line integral) CT data (after preprocessing), and $\|\cdot\|_{TV}$ represents a total variation (TV) transformation.

Embodiment 3

The system according to any of embodiments 1-2, wherein reconstructing an MRI image $u_{MRI}$ from the MRI data comprises using the following equation:

$$\min_{u_{MRI}} \|u_{MRI}\|_{TV} \text{ s.t. } RFu_{MRI} = g,$$

where F denotes the Fourier transform, R is a sampling mask in the k-space, g is the MRI data, and $\|\cdot\|_{TV}$ represents a total variation (TV) transformation.

Embodiment 4

The system according to any of embodiments 1-3, wherein estimating the corresponded CT-MRI image comprises using a structural coupling (SC) method.

Embodiment 5

The system according to embodiment 4, wherein the SC method comprises:
a) decomposing $u_{CT}$ into patches $p'_{CT} = E_j u_{CT}$;
b) decomposing $u_{MRI}$ into patches $p'_{MRI} = E_j u_{MRI}$;
c) optimizing the following equation by finding K-best suitable patches $\{p_{CT,i}{}^j\}$ and $\{p_{MRI,i}{}^j\}$, and their weights $\{w_i\}$ in $T_{CT}$ and $T_{MRI}$ to represent $p'_{CT}$ and $p'_{MRI}$ $$\min_{\beta_i}\left\|p_{MRI} - \sum_i w_i T_{MRI}\beta_i\right\|_2^2 + \left\|p_{CT} - \sum_i w_i T_{CT}\beta_i\right\|_2^2,$$

where $w_i$ equals the average of CT and MRI weightings calculated according to the below equation, $w_i=(w_{CT,i}+w_{MRI,i})/2$, and $\beta_i$ identifies surrounding high-dimensional data points, $$w'_{*,i} = \exp(-\|p_* - p_{*,i}\|_2^2/h^2) \text{ and } w_{*,i} = w'_{*,i}\bigg/\sum_i^K w'_{*,i},$$

where h is an empirical value that controls contributions of involved patches, and K is the number of surrounding data points;

d) estimating CT and MRI image patches with the corresponded CT and MRI image pairs in $T_{CT-MRI}$ and new weights $\{w_i\}$, $$p_{new,CT}^j \approx \sum_i^K w_i p_{CT,i}^j \cdot p_{new,MRI}^j \approx \sum_i^K w_i p_{MRI,i}^j;$$

e) estimating the corresponded CT image with $p'_{new,CT}$, $$u_{CT}^{est} = \left(\sum_j E_j^T E_j\right)^{-1}\left(\sum_j E_j^T p_{new,CT}^j\right);$$

and f) estimating the corresponded CT image with $p'_{new,CT}$, $$u_{MRI}^{est} = \left(\sum_j E_j^T E_j\right)^{-1}\left(\sum_j E_j^T p_{new,MRI}^j\right).$$

Embodiment 6

The system according to any of embodiments 1-5, wherein reconstructing the CT image $u_{CT}$ with $$u\frac{est}{CT}$$

and the CT data comprises using the following equation, $$\min_{u_{CT}}(1-\alpha)\|u_{CT}\|_{TV} + \alpha\|u_{CT} - u_{CT}^{est}\|_{TV} \text{ s.t. } Mu_{CT} = f,$$

where M is a system matrix, f is the (line integral) CT data (after preprocessing), a is a relaxation parameter, and $\|\cdot\|_{TV}$ represents a total variation (TV) transformation.

Embodiment 7

The system according to any of embodiments 1-6, wherein reconstructing the MRI image $u_{MRI}$ with $$u_{MRI}^{est}$$

and the MRI data comprises using the following equation, $$\min_{u_{MRI}} (1-\alpha)\|u_{MRI}\|_{TV} + \alpha\|u_{MRI} - u_{MRI}^{est}\|_{TV} \text{ s.t. } Fu_{MRI} = g,$$

where F denotes the Fourier transform, R is a sampling mask in the k-space, g is the MRI data, $\alpha$ is a relaxation parameter, and $\|\cdot\|_{TV}$ represents a total variation (TV) transformation.

Embodiment 8

The system according to any of embodiments 1-7, wherein steps iv) through vii) can be formulated as follows, $$\min_{(u_{CT}, u_{MRI}, \beta)} \|u_{CT}\|_{TV} + \lambda\|u_{MRI}\|_{TV} +$$
$$\gamma \sum_j \left( \left\| E_j u_{MRI} - \sum_i w_i T_{MRI} \beta_{j,i} \right\|_2^2 + \left\| E_j u_{CT} - \sum_i w_i T_{CT} \beta_{j,i} \right\|_2^2 \right)$$
$$\text{s.t. } Mu_{CT} = f, RFu_{MRI} = g,$$

where E is an operator to extract patches from an image, $\beta$ determines which patch is selected for linear approximation by assigning appropriate weighting factors $\{w_i\}$, M is a system matrix, f is the (line integral) CT data (after preprocessing), F denotes the Fourier transform, R is a sampling mask in the k-space, g is the MRI data, and $\|\cdot\|_{TV}$ represents a total variation (TV) transformation.

Embodiment 9

The system according to any of embodiments 1-8, wherein estimating the corresponded CT-MRI image comprises using an SC method implemented using a hashing method to accelerate the patch searching process.

Embodiment 10

The system according to any of embodiments 1-9, wherein the method of reconstructing CT and MRI images further comprises utilizing prior knowledge of CT images.

Embodiment 11

The system according to embodiment 10, wherein the prior knowledge of CT images comprises information from a CT image atlas.

Embodiment 12

The system according to any of embodiments 10-11, wherein the prior knowledge of CT images is utilized in step i).

Embodiment 13

The system according to any of embodiments 1-12, wherein the method of reconstructing CT and MRI images further comprises utilizing prior knowledge of MRI images.

Embodiment 14

The system according to embodiment 13, wherein the prior knowledge of MRI images comprises information from an MRI image atlas.

Embodiment 15

The system according to any of embodiments 13-14, wherein the prior knowledge of MRI images is utilized in step i).

Embodiment 16

The system according to any of embodiments 1-15, wherein the MRI subsystem comprises superconducting magnets.

Embodiment 17

The system according embodiment 16, wherein the superconducting magnets are room temperature superconducting magnets.

Embodiment 18

The system according to any of embodiments 1-17, wherein the MRI subsystem comprises two donut shaped magnets facing each other.

Embodiment 19

The system according to any of embodiments 1-18, wherein the MRI subsystem comprises two hexagonal magnet arrays facing each other.

Embodiment 20

The system according to any of embodiments 1-19, wherein the CT subsystem and the MRI subsystem are seamlessly integrated with one another.

Embodiment 21

The system according to any of embodiments 1-20, wherein components of the CT subsystem are quasi-stationary.

Embodiment 22

The system according to embodiment 22, wherein X-ray sources and detectors of the CT subsystem are distributed face-to-face along a circle.

Embodiment 23

The system according to any of embodiments 1-22, wherein the CT data comprises only a few-view set of CT data.

Embodiment 24

The system according to any of embodiments 1-23, wherein the method of reconstructing CT and MRI images comprises using an SC method and a compressive sensing (CS) method.

Embodiment 25

A machine-readable medium, having machine-executable instructions stored thereon that, when executed by at least one processor, perform a method of reconstructing CT and MRI images, the method comprising:
i) reconstructing a CT image $u_{CT}$ from CT data;
ii) reconstructing an MRI image $u_{MRI}$ from MRI data;
iii) setting an iteration step k=0;
iv) transforming a CT-MRI dataset $T_{CT-MRI}$ by the $u_{CT}$ and $u_{MRI}$;
v) estimating the corresponded CT-MRI image $$u_{CT}^{est} \text{ and } u_{MRI}^{est}$$

according to $u_{CT}$ and $u_{MRI}$ aided by the CT-MRI dataset $T_{CT-MRI}$;
vi) reconstructing the CT image $u_{CT}$ with $$u_{CT}^{est}$$

and the CT data;
vii) reconstructing the MRI image $u_{MRI}$ with $$u_{MRI}^{est}$$

and the MRI data;
viii) setting k=k+1; and
ix) repeating steps iv)-viii) until meeting stop criteria, at which point the current $$u_{CT}^{est}$$

is the reconstructed CT image and the current $$u_{MRI}^{est}$$

is the reconstructed MRI image.

Embodiment 26

The machine-readable medium according to embodiment 25, wherein reconstructing a CT image $u_{CT}$ from the CT data comprises using the following equation:

$$\min_{u_{CT}} \|u_{CT}\|_{TV} \text{ s.t. } Mu_{CT} = f,$$

where M is a system matrix, f is the (line integral) CT data (after preprocessing), and $\|\cdot\|_{TV}$ represents a total variation (TV) transformation.

Embodiment 27

The machine-readable medium according to any of embodiments 25-26, wherein reconstructing an MRI image $u_{MRI}$ from the MRI data comprises using the following equation:

$$\min_{u_{MRI}} \|u_{MRI}\|_{TV} \text{ s.t. } RFu_{MRI} = g,$$

where F denotes the Fourier transform, R is a sampling mask in the k-space, g is the MRI data, and $\|\cdot\|_{TV}$ represents a total variation (TV) transformation.

Embodiment 28

The machine-readable medium stem according to any of embodiments 25-27, wherein estimating the corresponded CT-MRI image comprises using a structural coupling (SC) method.

Embodiment 29

The machine-readable medium according to embodiment 28, wherein the SC method comprises:
a) decomposing $u_{CT}$ into patches $p_{CT}^j = E_j u_{CT}$;
b) decomposing $u_{MRI}$ into patches $p_{MRI}^j = E_j u_{MRI}$;
c) optimizing the following equation by finding K-best suitable patches $\{p_{CT,i}^j\}$ and $\{p_{MRI,i}^j\}$, and their weights $\{w_i\}$ in $T_{CT}$ and $T_{MRI}$ to represent $p_{CT}^j$ and $p_{MRI}^j$ $$\min_{\beta_i} \left\| p_{MRI} - \sum_i w_i T_{MRI} \beta_i \right\|_2^2 + \left\| p_{CT} - \sum_i w_i T_{CT} \beta_i \right\|_2^2,$$

where $w_i$ equals the average of CT and MRI weightings calculated according to the below equation, $w_i = (w_{CT,i} + w_{MRI,i})/2$, and $\beta_i$ identifies surrounding high-dimensional data points, $$w'_{*,i} = \exp(-\|p_* - p_{*,i}\|_2^2 / h^2) \text{ and } w_{*,i} = w'_{*,i} \Big/ \sum_i^K w'_{*,i},$$

where h is an empirical value that controls contributions of involved patches, and K is the number of surrounding data points;
d) estimating CT and MRI image patches with the corresponded CT and MRI image pairs in $T_{CT-MRI}$ and new weights $\{w_i\}$, $$p_{new,CT}^j \approx \sum_i^K w_i p_{CT,i}^j, \ p_{new,MRI}^j \approx \sum_i^K w_i p_{MRI,i}^j;$$

e) estimating the corresponded CT image with $p^j_{new,CT}$, $$u^{est}_{CT} = \left(\sum_j E_j^T E_j\right)^{-1}\left(\sum_j E_j^T p^j_{new,CT}\right);$$

and f) estimating the corresponded CT image with $p^j_{new,CT}$, $$u^{est}_{MRI} = \left(\sum_j E_j^T E_j\right)^{-1}\left(\sum_j E_j^T p^j_{new,MRI}\right).$$

Embodiment 30

The machine-readable medium according to any of embodiments 25-29, wherein reconstructing the CT image $u_{CT}$ with $$u^{est}_{CT}$$

and the CT data comprises using the following equation, $$\min_{u_{CT}}(1-\alpha)\|u_{CT}\|_{TV} + \alpha\|u_{CT} - u^{est}_{CT}\|_{TV} \text{ s.t. } Mu_{CT} = f,$$

where M is a system matrix, f is the (line integral) CT data (after preprocessing), $\alpha$ is a relaxation parameter, and $\|\cdot\|_{TV}$ represents a total variation (TV) transformation.

Embodiment 31

The machine-readable medium according to any of embodiments 25-30, wherein reconstructing the MRI image $u_{MRI}$ with $$u^{est}_{MRI}$$

and the MRI data comprises using the following equation, $$\min_{u_{MRI}}(1-\alpha)\|u_{MRI}\|_{TV} + \alpha\|u_{MRI} - u^{est}_{MRI}\|_{TV} \text{ s.t. } Fu_{MRI} = g,$$

where F denotes the Fourier transform, R is a sampling mask in the k-space, g is the MRI data, $\alpha$ is a relaxation parameter, and $\|\cdot\|_{TV}$ represents a total variation (TV) transformation.

Embodiment 32

The machine-readable medium according to any of embodiments 25-31, wherein steps iv) through vii) can be formulated as follows, $$\min_{(u_{CT},u_{MRI},\beta)} \|u_{CT}\|_{TV} + \lambda\|u_{MRI}\|_{TV} +$$

$$\gamma \sum_j \left(\left\|E_j u_{MRI} - \sum_i w_i T_{MRI}\beta_{j,i}\right\|_2^2 + \left\|E_j u_{CT} - \sum_i w_i T_{CT}\beta_{j,i}\right\|_2^2\right)$$

$$\text{s.t. } Mu_{CT} = f, RFu_{MRI} = g,$$

where E is an operator to extract patches from an image, $\beta$ determines which patch is selected for linear approximation by assigning appropriate weighting factors $\{w_i\}$, M is a system matrix, f is the (line integral) CT data (after preprocessing), F denotes the Fourier transform, R is a sampling mask in the k-space, g is the MRI data, and $\|\cdot\|_{TV}$ represents a total variation (TV) transformation.

Embodiment 33

The machine-readable medium according to any of embodiments 25-32, wherein estimating the corresponded CT-MRI image comprises using an SC method implemented using a hashing method to accelerate the patch searching process.

Embodiment 34

The machine-readable medium according to any of embodiments 25-33, wherein the method of reconstructing CT and MRI images further comprises utilizing prior knowledge of CT images.

Embodiment 35

The machine-readable medium according to embodiment 34, wherein the prior knowledge of CT images comprises information from a CT image atlas.

Embodiment 36

The machine-readable medium according to any of embodiments 34-35, wherein the prior knowledge of CT images is utilized in step i).

Embodiment 37

The machine-readable medium according to any of embodiments 25-36, wherein the method of reconstructing CT and MRI images further comprises utilizing prior knowledge of MRI images.

Embodiment 38

The machine-readable medium according to embodiment 37, wherein the prior knowledge of MRI images comprises information from an MRI image atlas.

Embodiment 39

The machine-readable medium according to any of embodiments 37-38, wherein the prior knowledge of MRI images is utilized in step i).

Embodiment 40

The machine-readable medium according to any of embodiments 25-39, wherein the CT data comprises only a few-view set of CT data.

Embodiment 41

The machine-readable medium according to any of embodiments 25-40, wherein the method of reconstructing CT and MRI images comprises using an SC method and a compressive sensing (CS) method.

Embodiment 42

A method of reconstructing CT and MRI images, the method comprising:
  i) reconstructing a CT image $u_{CT}$ from CT data;
  ii) reconstructing an MRI image $u_{MRI}$ from MRI data;
  iii) setting an iteration step k=0;
  iv) transforming a CT-MRI dataset $T_{CT\text{-}MRI}$ by the $u_{CT}$ and $u_{MRI}$;
  v) estimating the corresponded CT-MRI image $$u\frac{est}{CT} \text{ and } u\frac{est}{MRI}$$

according to $u_{CT}$ and $u_{MRI}$ aided by the CT-MRI dataset $T_{CT\text{-}MRI}$;
  vi) reconstructing the CT image $u_{CT}$ with $$u\frac{est}{CT}$$

and the CT data;
  vii) reconstructing the MRI image $u_{MRI}$ with $$u\frac{est}{MRI}$$

and the MRI data;
  viii) setting k=k+1; and
  ix) repeating steps iv)-viii) until meeting stop criteria, at which point the current $$u\frac{est}{CT}$$

is the reconstructed CT image and the current $$u\frac{est}{MRI}$$

is the reconstructed MRI image.

Embodiment 43

The method according to embodiment 42, wherein reconstructing a CT image $u_{CT}$ from the CT data comprises using the following equation:

$$\min_{u_{CT}} \|u_{CT}\|_{TV} \text{ s.t.} Mu_{CT} = f,$$

where M is a system matrix, f is the (line integral) CT data (after preprocessing), and $\|\bullet\|_{TV}$ represents a total variation (TV) transformation.

Embodiment 44

The method according to any of embodiments 42-43, wherein reconstructing an MRI image $u_{MRI}$ from the MRI data comprises using the following equation:

$$\min_{u_{MRI}} \|u_{MRI}\|_{TV} \text{ s.t.} RFu_{MRI} = g,$$

where F denotes the Fourier transform, R is a sampling mask in the k-space, g is the MRI data, and $\|\bullet\|_{TV}$ represents a total variation (TV) transformation.

Embodiment 45

The method stem according to any of embodiments 42-44, wherein estimating the corresponded CT-MRI image comprises using a structural coupling (SC) method.

Embodiment 46

The method according to embodiment 45, wherein the SC method comprises:
  a) decomposing $u_{CT}$ into patches $p^j_{CT}=E_j u_{CT}$;
  b) decomposing $u_{MRI}$ into patches $p^j_{MRI}=E_j u_{MRI}$;
  c) optimizing the following equation by finding K-best suitable patches $\{p_{CT,i}{}^j\}$ and $\{p_{MRI,i}{}^j\}$, and their weights $\{w_i\}$ in $T_{CT}$ and $T_{MRI}$ to represent $p^j_{CT,i}$ and $p^j_{MRI}$ $$\min_{\beta_i} \left\|p_{MRI} - \sum_i w_i T_{MRI}\beta_i\right\|_2^2 + \left\|p_{CT} - \sum_i w_i T_{CT}\beta_i\right\|_2^2,$$

where $w_i$ equals the average of CT and MRI weightings calculated according to the below equation, $w_i=(w_{CT,i} w_{MRI,i})/2$, and $\beta_i$ identifies surrounding high-dimensional data points, $$w'_{*,i} = \exp(-\|p_* - p_{*,i}\|_2^2/h^2) \text{ and } w_{*,i} = w'_{*,i} \Big/ \sum_i^K w'_{*,i},$$

where h is an empirical value that controls contributions of involved patches, and K is the number of surrounding data points;
  d) estimating CT and MRI image patches with the corresponded CT and MRI image pairs in $T_{CT\text{-}MRI}$ and new weights $\{w_i\}$, $$p_{new,CT}^j \approx \sum_i^K w_i p_{CT,i}^j, \quad p_{new,MRI}^j \approx \sum_i^K w_i p_{MRI,i}^j;$$

e) estimating the corresponded CT image with $p_{new,CT}^j$, $$u_{CT}^{est} = \left(\sum_j E_j^T E_j\right)^{-1}\left(\sum_j E_j^T p_{new,CT}^j\right);$$

and f) estimating the corresponded CT image with $p_{new,CT}^j$, $$u_{MRI}^{est} = \left(\sum_j E_j^T E_j\right)^{-1}\left(\sum_j E_j^T p_{new,MRI}^j\right).$$

Embodiment 47

The method according to any of embodiments 42-46, wherein reconstructing the CT image $u_{CT}$ with $$u_{CT}^{est}$$

and the CT data comprises using the following equation, $$\min_{u_{CT}} (1-\alpha)\|u_{CT}\|_{TV} + \alpha\|u_{CT} - u_{CT}^{est}\|_{TV} \quad \text{s.t.} \quad Mu_{CT} = f,$$

where M is a system matrix, f is the (line integral) CT data (after preprocessing), α is a relaxation parameter, and $\|\cdot\|_{TV}$ represents a total variation (TV) transformation.

Embodiment 48

The method according to any of embodiments 42-47, wherein reconstructing the MRI image $u_{MRI}$ with $$u_{MRI}^{est}$$

and the MRI data comprises using the following equation, $$\min_{u_{MRI}} (1-\alpha)\|u_{MRI}\|_{TV} + \alpha\|u_{MRI} - u_{MRI}^{est}\|_{TV} \quad \text{s.t.} \quad Fu_{MRI} = g,$$

where F denotes the Fourier transform, R is a sampling mask in the k-space, g is the MRI data, α is a relaxation parameter, and $\|\cdot\|_{TV}$ represents a total variation (TV) transformation.

Embodiment 49

The method according to any of embodiments 42-48, wherein steps iv) through vii) can be formulated as follows, $$\min_{(u_{CT}, u_{MRI}, \beta)} \|u_{CT}\|_{TV} + \lambda\|u_{MRI}\|_{TV} +$$
$$\gamma \sum_j \left(\left\|E_j u_{MRI} - \sum_i w_i T_{MRI} \beta_{j,i}\right\|_2^2 + \left\|E_j u_{CT} - \sum_i w_i T_{CT} \beta_{j,i}\right\|_2^2\right)$$
$$\text{s.t.} \quad Mu_{CT} = f, \quad RFu_{MRI} = g,$$

where E is an operator to extract patches from an image, β determines which patch is selected for linear approximation by assigning appropriate weighting factors $\{w_i\}$, M is a system matrix, f is the (line integral) CT data (after preprocessing), F denotes the Fourier transform, R is a sampling mask in the k-space, g is the MRI data, and $\|\cdot\|_{TV}$ represents a total variation (TV) transformation.

Embodiment 50

The method according to any of embodiments 42-49, wherein estimating the corresponded CT-MRI image comprises using an SC method implemented using a hashing method to accelerate the patch searching process.

Embodiment 51

The method according to any of embodiments 42-50, wherein the method of reconstructing CT and MRI images further comprises utilizing prior knowledge of CT images.

Embodiment 52

The method according to embodiment 51, wherein the prior knowledge of CT images comprises information from a CT image atlas.

Embodiment 53

The method according to any of embodiments 51-52, wherein the prior knowledge of CT images is utilized in step i).

Embodiment 54

The method according to any of embodiments 42-53, wherein the method of reconstructing CT and MRI images further comprises utilizing prior knowledge of MRI images.

Embodiment 55

The method according to embodiment 54, wherein the prior knowledge of MRI images comprises information from an MRI image atlas.

Embodiment 56

The method according to any of embodiments 54-55, wherein the prior knowledge of MRI images is utilized in step i).

Embodiment 57

The method according to any of embodiments 42-56, wherein the CT data comprises only a few-view set of CT data.

Embodiment 58

The method according to any of embodiments 42-57, wherein the method of reconstructing CT and MRI images comprises using an SC method and a compressive sensing (CS) method.

Embodiment 59

A system for simultaneous computed tomography (CT)-magnetic resonance imaging (MRI), the system comprising:
a CT subsystem for obtaining CT data;
an MRI subsystem for obtaining MRI data;
at least one processor; and
a machine-readable medium, in operable communication with the CT subsystem, the MRI subsystem, and the at least one processor, having machine-executable instructions stored thereon that, when executed by the at least one processor, perform a method of reconstructing CT and MRI images,
wherein the MRI subsystem comprises superconducting magnets.

Embodiment 60

The system according embodiment 59, wherein the superconducting magnets are room temperature superconducting magnets.

Embodiment 61

The system according to any of embodiments 59-60, wherein the MRI subsystem comprises two donut shaped magnets facing each other.

Embodiment 62

The system according to any of embodiments 59-61, wherein the MRI subsystem comprises two hexagonal magnet arrays facing each other.

Embodiment 63

The system according to any of embodiments 59-62, wherein the CT subsystem and the MRI subsystem are seamlessly integrated with one another.

Embodiment 64

The system according to any of embodiments 59-63, wherein components of the CT subsystem are quasi-stationary.

Embodiment 65

The system according to embodiment 64, wherein X-ray sources and detectors of the CT subsystem are distributed face-to-face along a circle.

Embodiment 66

The system according to any of embodiments 59-65, wherein the method of reconstructing CT and MRI images is the method according to any of embodiments 42-58.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

EXAMPLE 1

Numerical simulations were performed with representative CT and MRI datasets to evaluate the results of the simultaneous CT-MRI image reconstruction approaches as described herein. In the simultaneous CT-MRI scanner, there was a limited number of X-ray sources in the CT subsystem, and a low-background magnetic field in the MRI subsystem. This cost-effective starting point actually posed an interesting challenge to investigate few-view CT and low resolution MRI coupling using a simultaneous CT-MRI image reconstruction algorithm.

In the simulations, CT and MRI datasets were derived from various sources: 1) established numerical phantoms (modified NCAT phantom (mNCAT)—see also Segars et al., Development and application of the new dynamic Nurbs-based Cardiac-Torso (NCAT) phantom, J. Nucl. Med., vol. 42, pp. 7p-7p, 2001; which is hereby incorporated by reference herein in its entirety); 2) the visible human project (VHP) (Ackerman, The visible human project, Proc. IEEE, vol. 86, no. 3, pp. 504-511, Mar. 1998; which is hereby incorporated by reference herein in its entirety); and 3) in vivo multimodality porcine imaging studies. In these experiments, identical samples were sequentially imaged by CT and MRI scanners.

FIG. 3a shows a ground truth CT image (left), a ground truth MRI image (center), and a registration result image (right) for the modified NCAT phantom (mNCAT). FIG. 3b shows a ground truth CT image (left), a ground truth MRI image (center), and a registration result image (right) for the visible human project phantom (VHP). FIG. 3c shows a ground truth CT image (left), a ground truth MRI image (center), and a registration result image (right) for the in vivo porcine sample.

In the numerical phantom experiment, the CT and MRI datasets have perfect spatial registration, as shown in FIG. 3a. In the other two real-dataset experiments, the CT and MRI scans were performed sequentially; thus, there were small non-rigid movements between their CT and MRI datasets, and their volumes were in different voxel sizes. Hence, a rigid registration and interpolation process was incorporated to align the CT and MRI datasets, as shown in FIG. 3. In the VHP experiment (FIG. 3b), the MRI dataset was composed of T2-weighted images. In the porcine multimodality imaging study (FIG. 3c), dynamic trans-axial CT and MRI images were collected. Sequential CT and MRI images were acquired at the Yale University of the porcine lower extremity of an anesthetized animal in a fixed position, with the full approval of the Institutional Animal Care and Use Committee. The high-resolution porcine CT images of the lower extremities were acquired on a 64-slice CT scanner (Discovery VCT, GE Healthcare) following administration of iodinated contrast (Omnipaque 350 mgI/ml) to define vascular anatomy. MRI time-off-light and phase velocity images were acquired on a 1.5-T MR system (Sonata, Siemens) as non-contrast alternative approaches to define vascular anatomy and flow physiology respectively.

Figures 5A, 5B, 5C:
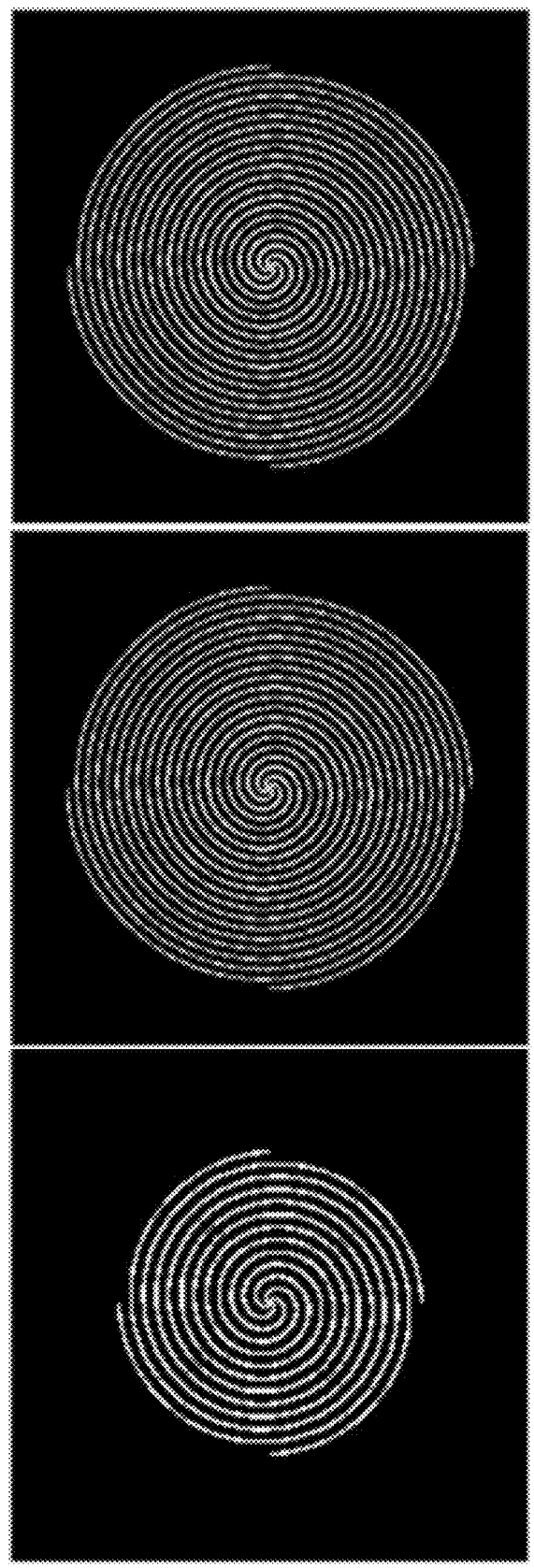
FIG. 5a shows an image of a low magnetic field measurement in an MRI sub-system for mNCAT.
FIG. 5b shows an image of a low magnetic field measurement in an MRI sub-system for VHP.
FIG. 5c shows an image of a low magnetic field measurement in an MRI sub-system for a porcine sample.

To simulate a simultaneous CT-MRI scan, the CT and MRI images in each experiment were re-projected and re-sampled according to appropriate imaging protocols. In the CT subsystem, the number of X-ray sources was set to 10 in the mNCAT experiment, and 15 sources were assumed in each of the VHP and porcine experiments. Without the loss of generality, only fan-beam geometry was considered. There were 512 channels per detector array for the numerical phantom, and 400 in each of the VHP and porcine experiments. In the MRI subsystem, the k-space was sampled in a low-frequency area (see FIG. 5) due to the low-background field utilized in the combined CT-MRI design. FIGS. 5a, 5b, and 5c show images of low magnetic field measurements in an MRI sub-system for the mNCAT, the VHP, and the porcine sample, respectively. Referring to FIGS. 5a-5c, sampling patterns in the k-space are shown under sampling rates of 92.5%, 82.7%, and 89.0%, respectively.

Reconstructed images in mNCAT, VHP, and porcine experiments comprised 256×256, 200×200, 320×320 pixels, respectively. During the offline process for the simultaneous CT-mNCAT MRI reconstruction, three tables of paired CT-MRI image patches, $T_{CT-MRI}^{mNCAT}, T_{CT-MRI}^{VHP}$, and $T_{CT-MRI}^{porcine}$ were constructed with CT and MRI slices from mNCAT, VHP, and porcine datasets, respectively. It should be noted that there was no overlap between the images used for training CT-MRI patch tables and the images tested for simultaneous CT-MRI reconstruction.

For comparison, the conventional TV-based approach was implemented and applied for separate CT and MRI reconstructions. Both the conventional and proposed algorithms were implemented in the Split-Bregman framework. Images were reconstructed with competing algorithms and quantitatively compared in terms of the root-mean-square error (RMSE) and the structural similarity index (SSIM). The RMSE quantifies the difference between the reconstructed image and the ground truth. The SSIM measures similarity between a reconstructed image and the ground truth. The higher the structural similarity between the two images, the closer the SSIM value approaches to 1. In each experiment, RMSE was used to quantify the differences between the reconstructed and ground truth images with varying patch size ($p_n$) in $T_{CT-MRI}$ to choose an optimal value.

Figure 6A:
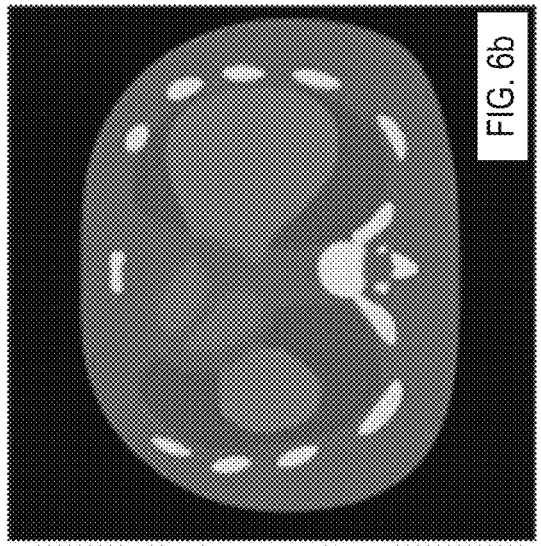
FIG. 6a shows a CT image for a mNCAT simulation, reconstructed using total variation (TV)-based reconstruction.
Figure 6B:
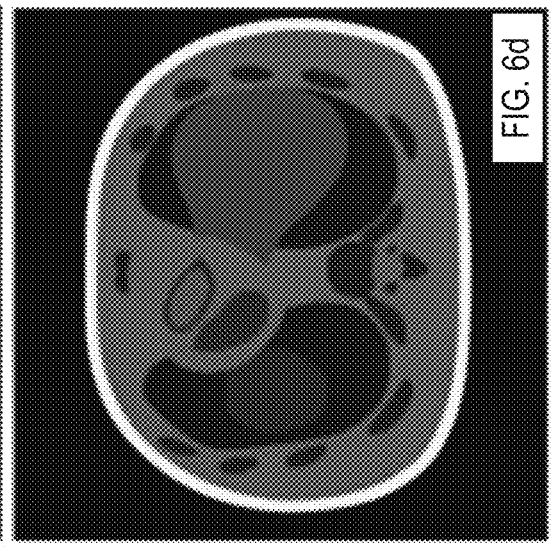
FIG. 6b shows a CT image for a mNCAT simulation, reconstructed using simultaneous CT-MRI reconstruction according to an embodiment of the subject invention.
Figure 6C:
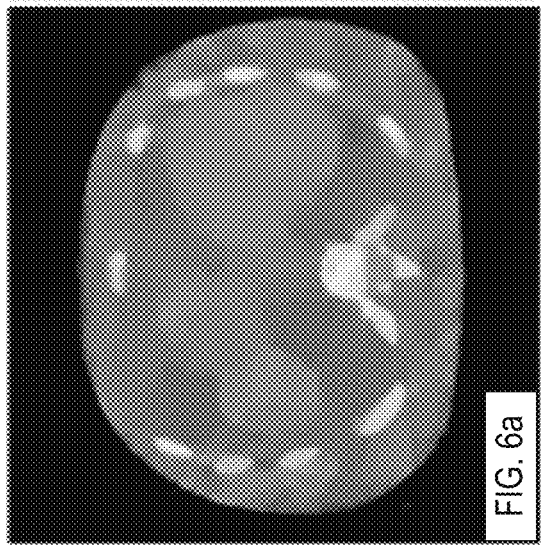
FIG. 6c shows an MRI image for a mNCAT simulation, reconstructed using TV-based reconstruction.
Figure 6D:
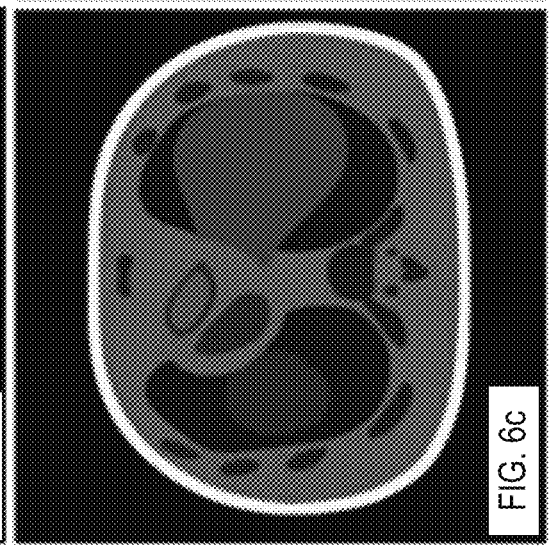
FIG. 6d shows an MRI image for a mNCAT simulation, reconstructed using simultaneous CT-MRI reconstruction according to an embodiment of the subject invention.

FIGS. 6a and 6b show CT images for the mNCAT simulation, reconstructed using total variation (TV)-based reconstruction and simultaneous CT-MRI reconstruction according to an embodiment of the subject invention, respectively. FIGS. 6c and 6d show MRI images for the mNCAT simulation, reconstructed using TV-based reconstruction and simultaneous CT-MRI reconstruction according to an embodiment of the subject invention, respectively. FIGS. 6e-6h show images of the residual errors relative to ground truth for the reconstructions of FIGS. 6a-6d, respectively. FIGS. 6a-6d are displayed in [0,1], and FIGS. 6e-6h are displayed in [−0.15, 0.15].

Figure 7A:
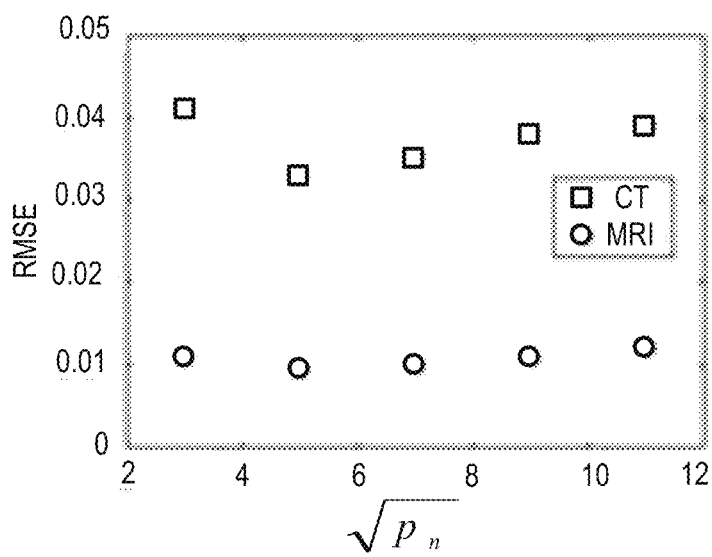
FIG. 7a shows a plot of root-mean-square error (RMSE) with respect to patch size ($\sqrt{p_n}$) for simultaneous CT-MRI construction in a mNCAT experiment.
Figure 7B:
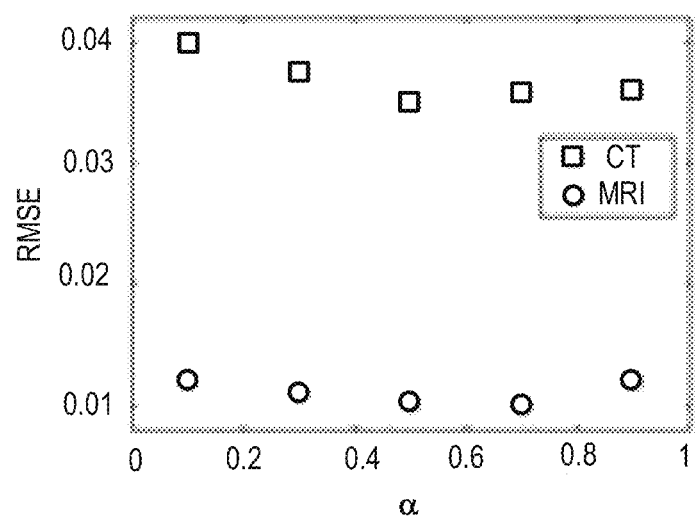
FIG. 7b shows a plot of RMSE with respect to relaxation parameter (a) for simultaneous CT-MRI construction in a mNCAT experiment.
Figure 7C:
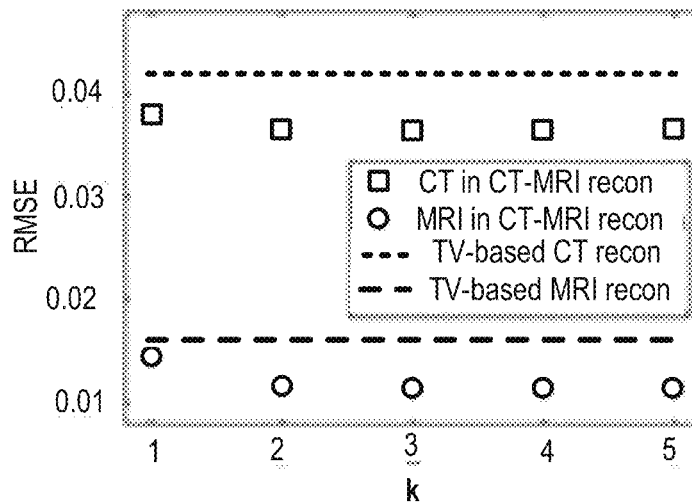
FIG. 7c shows a plot of RMSE with respect to iteration index (k) for simultaneous CT-MRI construction in a mNCAT experiment.

FIGS. 7a, 7b, and 7c show plots of root-mean-square error (RMSE) with respect to patch size ($\sqrt{p_n}$), relaxation parameter (α), and iteration index (k), respectively, for simultaneous CT-MRI construction in the mNCAT experiment. Referring to FIGS. 7a-7c, RMSE quantifies the differences between the reconstructed and ground truth images with respect to various patch sizes and relaxation parameter values, as well as the intermediate results as a function of the iteration index k (with $\sqrt{p_n}$=5). In each of FIGS. 7a and 7b, the square points (upper section of plot) are for CT, and the circle points (lower section of plot) are for MRI. In FIG. 7c, the square points (upper section of plot) are for CT-MRI-based CT reconstruction, and the circle points (lower section of plot) are for CT-MRI-based MRI reconstruction, the upper dotted line is for TV-based CT reconstruction, and the lower dotted line is for TV-based MRI reconstruction.

FIGS. 8a and 8b show plots of RMSE with respect to various registration errors (Δx, Δy) for CT images and MRI images, respectively, in simultaneous CT-MRI construction in the mNCAT experiment. FIGS. 8c and 8d show plots of RMSE with respect to various noise levels for simultaneous CT-MRI construction (squares) and TV-based reconstruction ("x" data points) for CT images and MRI images, respectively, in the mNCAT experiment. The RMSE of FIGS. 8a and 8b quantifies the differences between the reconstructed and ground truth images with respective to various registration errors between CT and MRI images, respectively, and the RMSE of FIGS. 8c and 8d quantifies the differences between the reconstructed and ground truth images at different noise levels.

FIGS. 9a and 9b show CT images for the VHP simulation, reconstructed using TV-based reconstruction and simultaneous CT-MRI reconstruction according to an embodiment of the subject invention, respectively. FIGS. 9c and 9d show MRI images for the VHP simulation, reconstructed using TV-based reconstruction and simultaneous CT-MRI reconstruction according to an embodiment of the subject invention, respectively. FIGS. 9e-9h show images of the residual errors relative to ground truth for the reconstructions of FIGS. 9a-9d, respectively. FIGS. 9a-9d are displayed in [0,1], and FIGS. 9e-9h are displayed in [−0.2, 0.2].

Figure 10A:
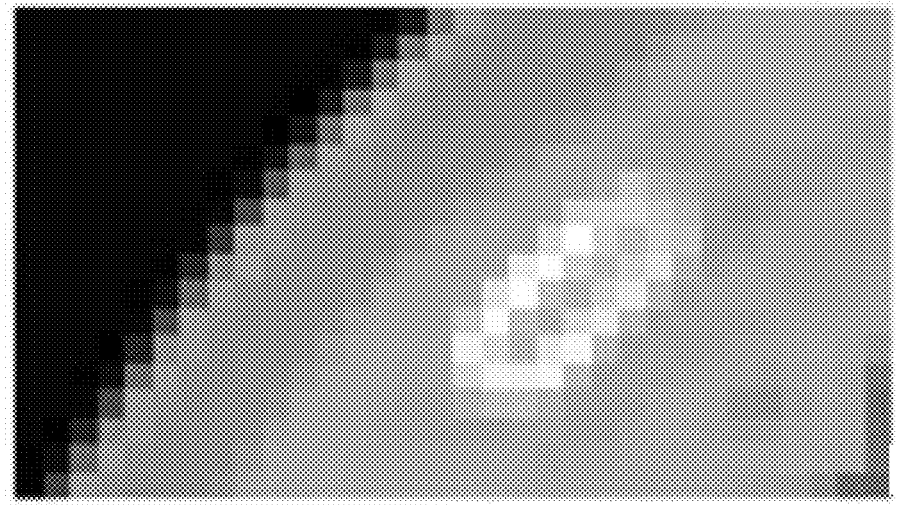
FIG. 10a shows a local enlarged view of a ground truth CT image for a VHP experiment.
Figure 10B:
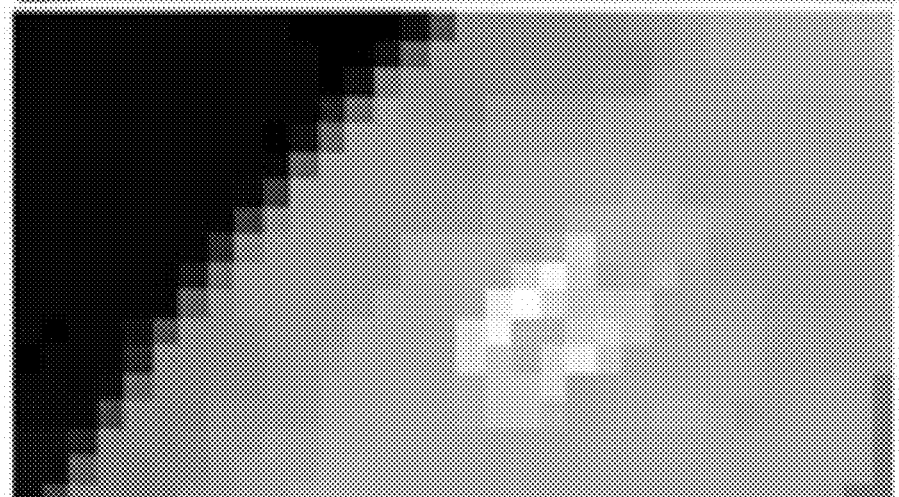
FIG. 10b shows a local enlarged view of a reconstructed CT image for a VHP experiment, reconstructed using TV-based reconstruction.
Figure 10C:
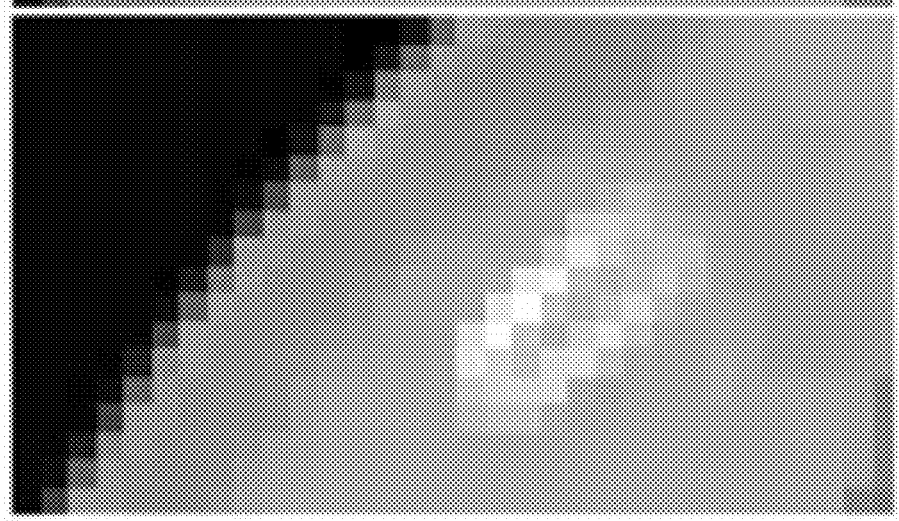
FIG. 10c shows a local enlarged view of a reconstructed CT image for a VHP experiment, reconstructed using simultaneous CT-MRI reconstruction according to an embodiment of the subject invention.

FIGS. 10a-10c show local enlarged views of a ground truth CT image, a reconstructed CT image using TV-based reconstruction, and a reconstructed CT image using simultaneous CT-MRI reconstruction, respectively, for the VHP experiment. FIGS. 10d-10f show local enlarged views of a ground truth MRI image, a reconstructed MRI image using TV-based reconstruction, and a reconstructed MRI image using simultaneous CT-MRI reconstruction, respectively, for the VHP experiment.

Figure 11A:
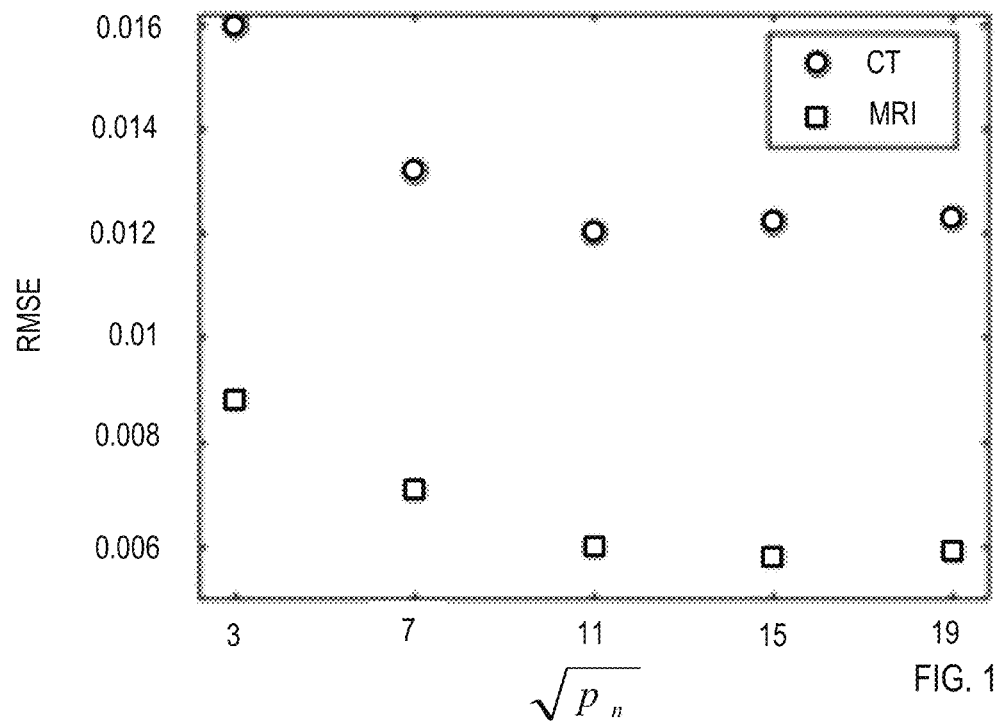
FIG. 11a shows a plot of root-mean-square error (RMSE) with respect to patch size ($\sqrt{p_n}$) for simultaneous CT-MRI construction in a VHP experiment.
Figure 11B:
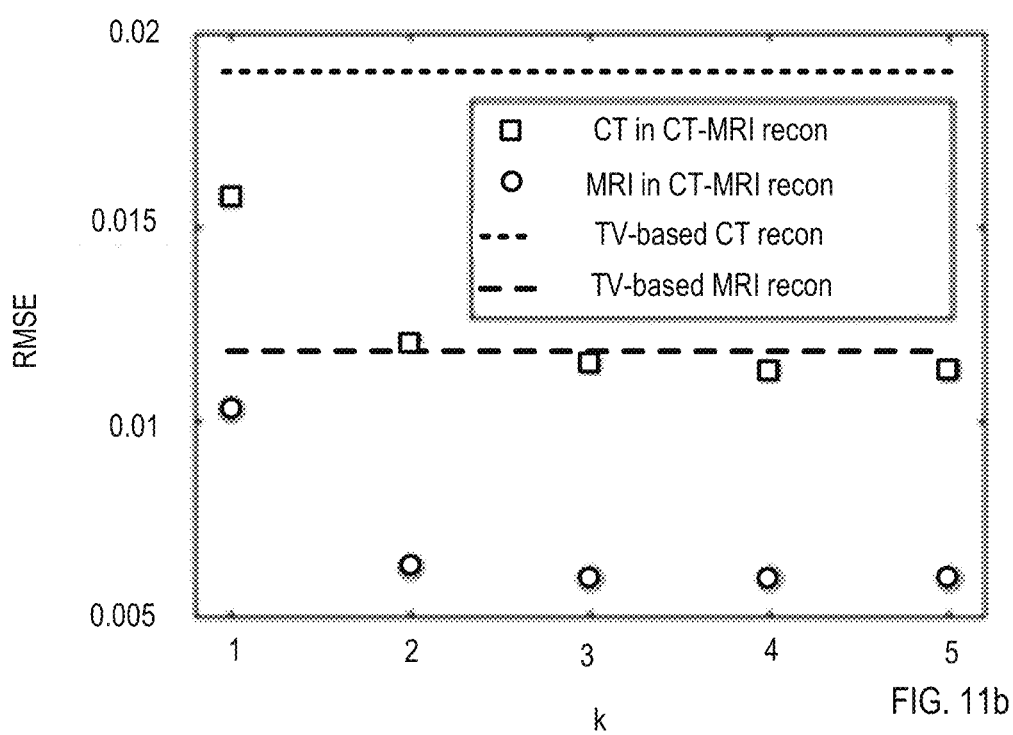
FIG. 11b shows a plot of RMSE with respect to iteration index (k) for simultaneous CT-MRI construction in a VHP experiment.

FIGS. 11a and 11b show plots of RMSE with respect to patch size ($\sqrt{p_n}$) and iteration index (k), respectively, for simultaneous CT-MRI construction in the VHP experiment. Referring to FIGS. 11a and 11b, RMSE quantifies the differences between the reconstructed and ground truth images with respect to various patch sizes, as well as the intermediate results as a function of the iteration index k (with $\sqrt{p_n}$=15). In FIG. 11a, the circle points (upper section of plot) are for CT, and the square points (lower section of plot) are for MRI. In FIG. 11b, the square points (upper section of plot) are for CT-MRI-based CT reconstruction, and the circle points (lower section of plot) are for CT-MRI-based MRI reconstruction, the upper dotted line is for TV-based CT reconstruction, and the lower dotted line is for TV-based MRI reconstruction.

FIGS. 12a and 12b show CT images for the porcine sample simulation, reconstructed using TV-based reconstruction and simultaneous CT-MRI reconstruction according to an embodiment of the subject invention, respectively. FIGS. 12c and 12d show MRI images for the porcine sample simulation, reconstructed using TV-based reconstruction and simultaneous CT-MRI reconstruction according to an embodiment of the subject invention, respectively. FIGS. 12e-12h show images of the residual errors relative to ground truth for the reconstructions of FIGS. 12a-12d, respectively. FIGS. 12a-12d are displayed in [0,1], FIGS. 12e and 12f are displayed in [−0.3, 0.3], and FIGS. 12g and 12h are displayed in [−0.2, 0.2].

FIGS. 13a-13c show local enlarged views of a ground truth CT image, a reconstructed CT image using TV-based reconstruction, and a reconstructed CT image using simultaneous CT-MRI reconstruction, respectively, for the porcine sample experiment. FIGS. 13d-13f show local enlarged views of a ground truth MRI image, a reconstructed MRI image using TV-based reconstruction, and a reconstructed MRI image using simultaneous CT-MRI reconstruction, respectively, for the porcine sample experiment. Veins show as black and arteries show as white, demonstrating improved definition of small vascular structures.

Figure 14A:
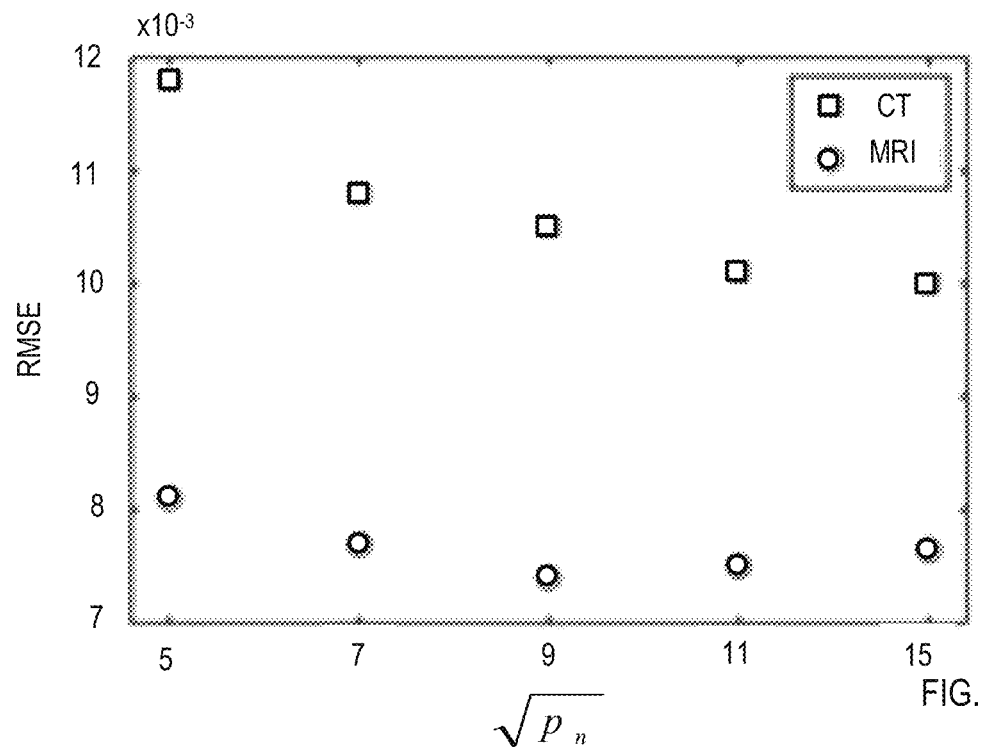
FIG. 14a shows a plot of root-mean-square error (RMSE) with respect to patch size ($\sqrt{p_n}$) for simultaneous CT-MRI construction in a porcine sample experiment.
Figure 14B:
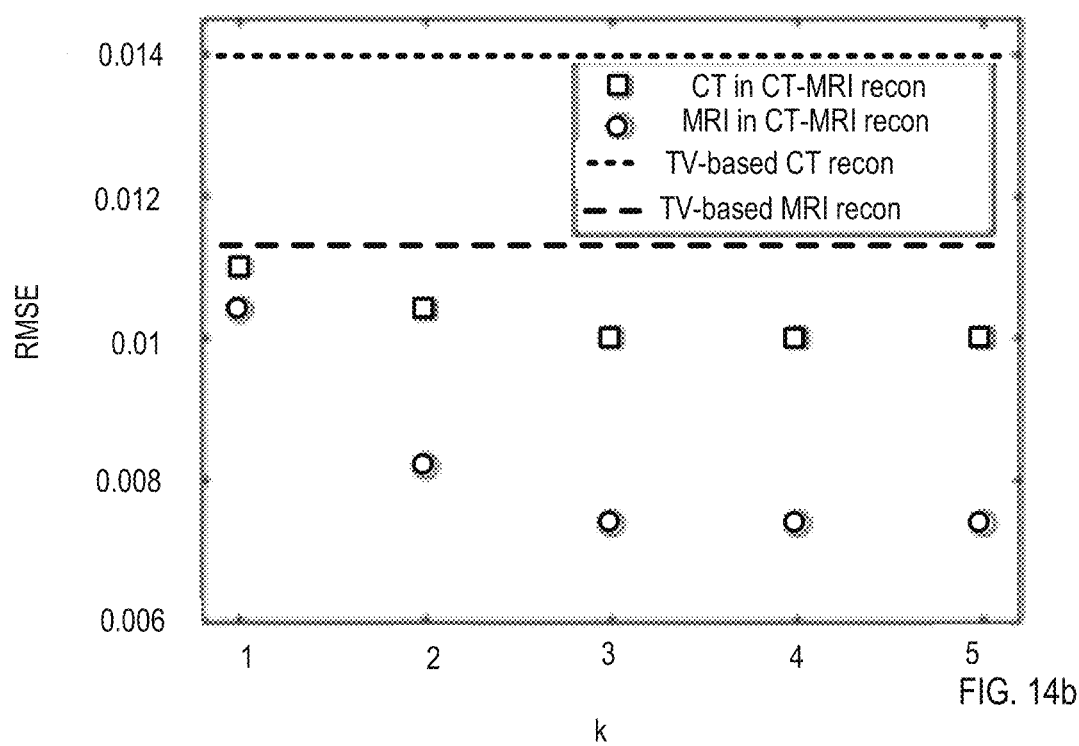
FIG. 14b shows a plot of RMSE with respect to iteration index (k) for simultaneous CT-MRI construction in a porcine sample experiment.

FIGS. 14a and 14b show plots of RMSE with respect to patch size ($\sqrt{p_n}$) and iteration index (k), respectively, for simultaneous CT-MRI construction in the porcine sample experiment. Referring to FIGS. 14a and 14b, RMSE quantifies the differences between the reconstructed and ground truth images with respect to various patch sizes, as well as the intermediate results as a function of the iteration index k (with $\sqrt{p_n}$=15). In FIG. 14a, the square points (upper section of plot) are for CT, and the circle points (lower section of plot) are for MRI. In FIG. 14b, the square points (upper section of plot) are for CT-MRI-based CT reconstruction, and the circle points (lower section of plot) are for CT-MRI-based MRI reconstruction, the upper dotted line is for TV-based CT reconstruction, and the lower dotted line is for TV-based MRI reconstruction.

Figure 15A:
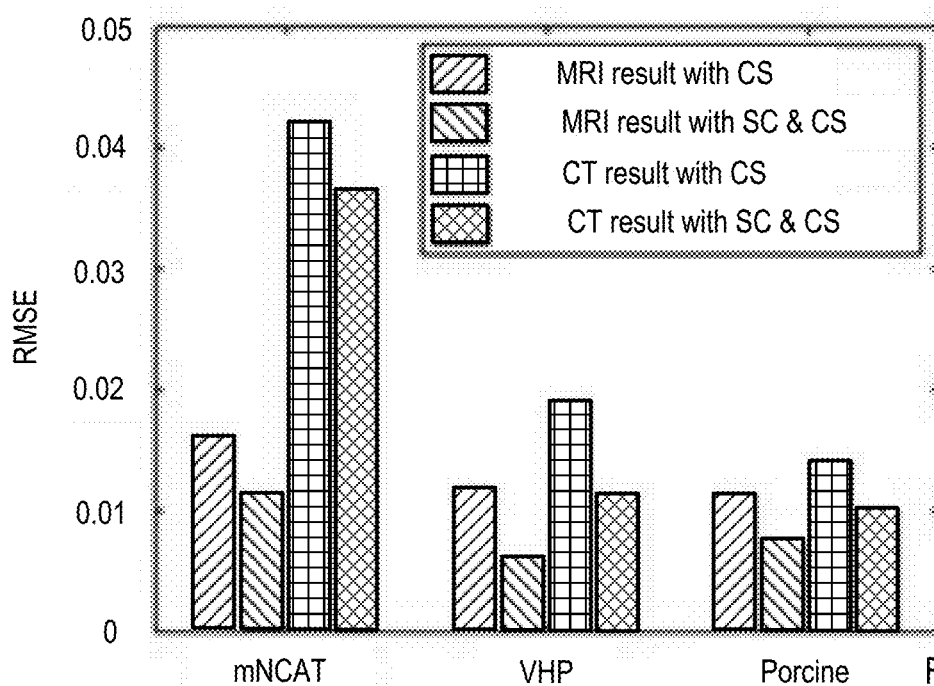
FIG. 15a shows a quantitative summary of the RMSE for mNCAT, VHP, and porcine sample experiments, for MRI results with compressive sensing (CS), MRI results with SC and CS, CT results with CS, and CT results with SC and CS.
Figure 15B:
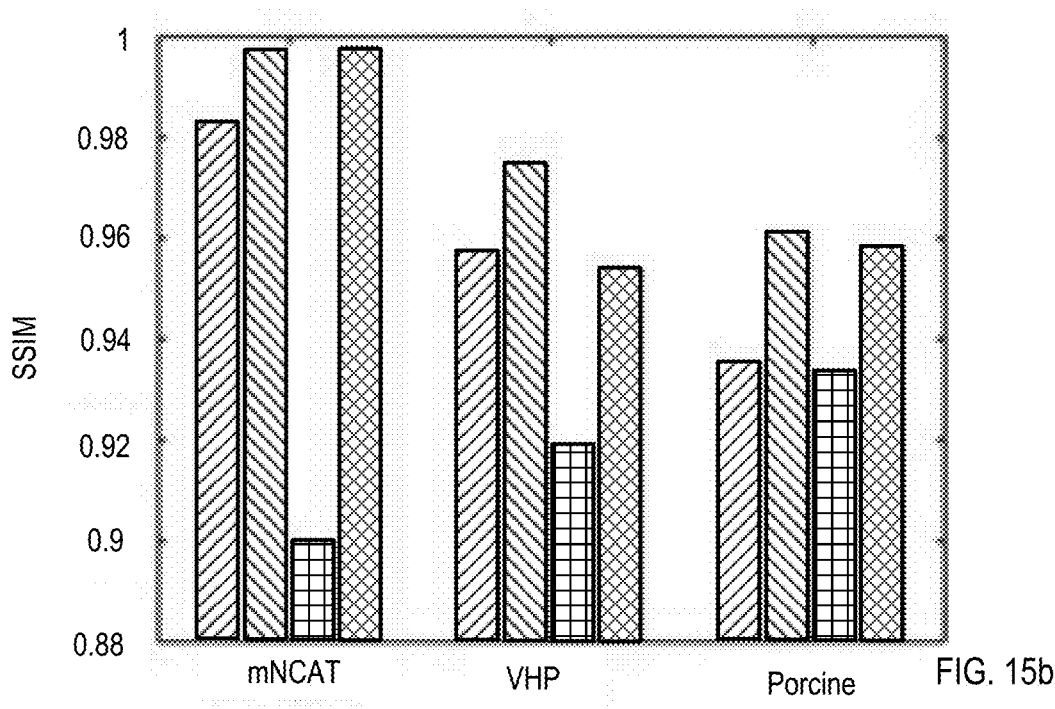
FIG. 15b shows a quantitative summary of the structural similarity index (SSIM) for mNCAT, VHP, and porcine sample experiments, for MRI results with CS, MRI results with SC and CS, CT results with CS, and CT results with SC and CS.

FIGS. 15a and 15b show a quantitative summary of the RMSE and structural similarity index (SSIM), respectively, for the mNCAT, VHP, and porcine sample experiments. In each data grouping (mNCAT, VHP, and porcine in each of FIGS. 15a and 15b), the left-most bar is for MRI result with CS, the second-from-the-left bar is for MRI result with SC and CS, the second-from-the-right bar is for CT result with CS, and the right-most bar is for CT result with SC and CS.

Based on the results, (e.g., FIG. 7a), the optimal patch size was 5×5 pixels for the mNCAT experiment. The same approach was applied to the VHP and porcine experiments, both of which yielded the optimal patch size 15×15 pixels, as shown in FIGS. 11a and 14a, respectively. In each modality-specific reconstruction, the relaxation parameter α was used to balance the regularization effects of TV in an image and TV between images in Equations (7) and (8). FIG. 7b shows the RMSE results with different α values. The optimized setting of the parameter α is affected by many factors, such as estimation accuracy, measurement noise, and others. Without loss of generality, in our experiments, α was empirically set to α=0.5.

With the well-trained CT-MRI image pair table, the simultaneous CT-MRI reconstruction method was compared with the conventional TV-based method, and the residual errors relative to the ground truths were displayed for the mNCAT, VHP, and porcine experiments in FIGS. 6, 9, and 12, respectively. Enlarged views of local regions, denoted by a red box in FIGS. 9 and 12, were plotted and compared with the ground truth images for VHP and porcine experiments in FIGS. 10 and 13, respectively. In FIG. 8, an error analysis on the mNCAT experiment was performed. Registration errors between CT and MRI images were considered, represented by (Δx,Δy) in the unit of pixel. FIGS. 8a and 8b show the results for different registration errors, and FIGS. 8c and 8d present the results from 3%, 5%, and 10% noisy measurements. In the experiments, the Gaussian-type noise was added into both the CT and MRI measurements.

Referring again to FIGS. 6, 8, 9, 11, and 12, it is clear that there are less intensity fluctuations in the residual errors of images reconstructed with the simultaneous CT-MRI reconstruction method, as compared with the conventional TV-based reconstruction methods. The RMSE index quantified results are shown in FIGS. 7c, 11b, and 14b. The intermediate reconstruction results of the proposed method, quantified with RMSE, are plotted with respect to the iteration index k for comparison. The results suggest that the simultaneous CT-MRI reconstruction algorithm has a fast convergence speed: two outer iterations appeared optimal in the experiments. In each loop, two optimization problems (see Equations (6) and (7)) were involved, which are started with zero initial guesses and accordingly estimated images. As compared with conventional iterative reconstructions for CT and MRI, the simultaneous CT-MRI reconstruction method can require an extra patch searching step and two iterations.

In FIGS. 10 and 11, local regions in the CT images from the TV-based and simultaneous CT-MRI reconstructions are enlarged and compared with the ground truth images. By utilizing the physical correlation between CT and MRI images, the simultaneous CT-MRI performance was good even though the view number of the CT subsystem was significantly lower than that of a conventional CT scan.

The reconstructions for the mNCAT, VHP, and porcine experiments were quantitatively compared. The results are summarized in FIG. 15. In these three experiments, the simultaneous CT-MRI image reconstruction using the SC and CS framework always provided better reconstructions compared with the individual reconstructions.

EXAMPLE 2

A numerical simulation was run to perform simultaneous CT-MRI image reconstruction. CT and MRI datasets were derived from the Visible Human Project (VHP). The MRI dataset included T2-weighted images. The CT and MRI images were deformed to be different from the atlas and reprojected to simulate CT and MRI measurements. In the CT setup, 15 sources were assumed. In the MRI setup, the k-space was spirally sampled only in a low-frequency area.

Figure 22:
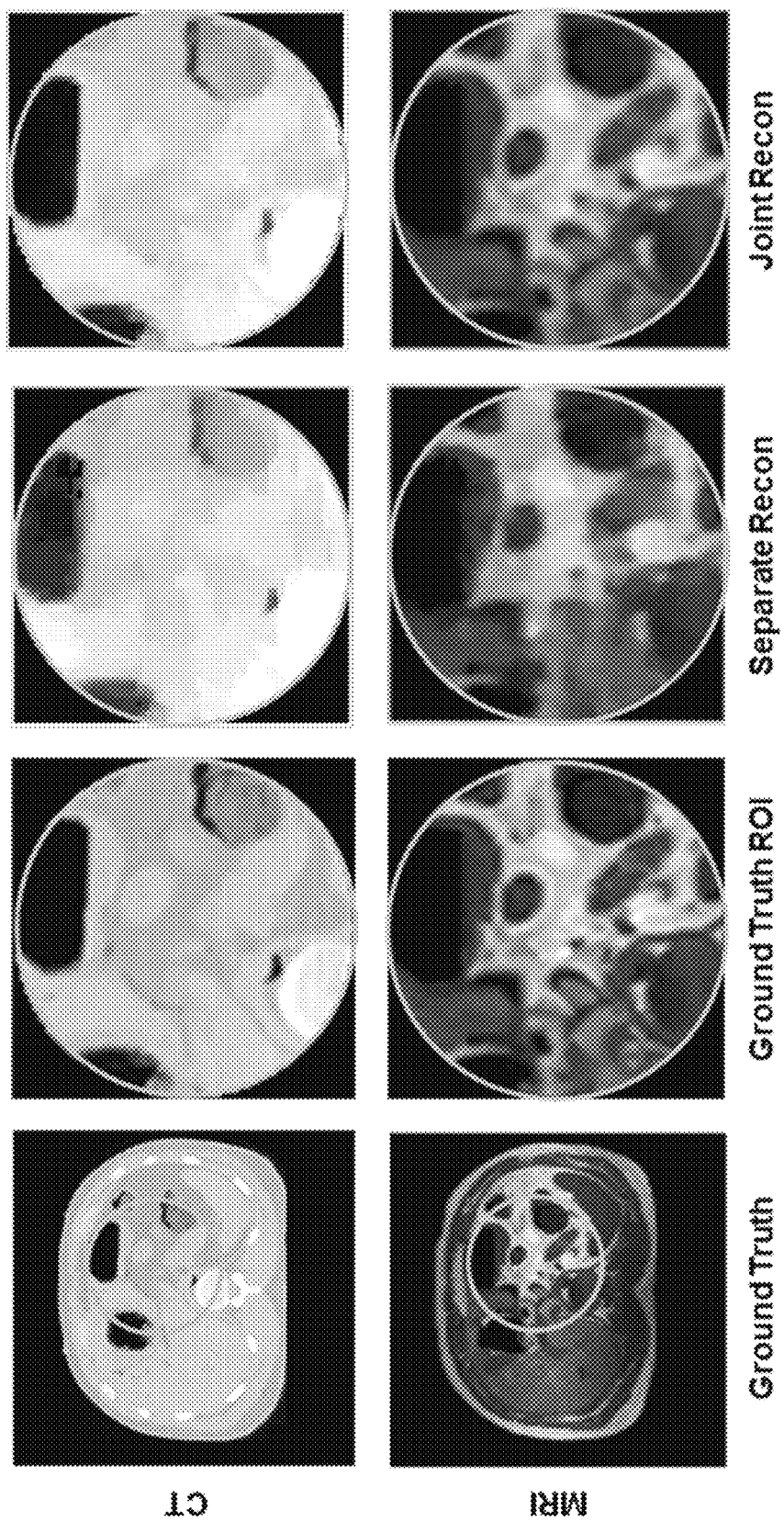
FIG. 22 shows images of an interior scan with 15 views.

FIG. 22 shows images of the interior scan with 15 views. Each image in the first row is CT, and each image in the second row is for MRI. The first column is ground truth for the entire scan; the second column is ground truth for the ROI in the circle in the first column images; the third column is using separate CT (first row) and MRI (second row) reconstruction; and the fourth column is using joint reconstruction. Referring to FIG. 22, the results from the joint CT-MRI reconstruction were good.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

What is claimed is:

1. A system for simultaneous computed tomography (CT)-magnetic resonance imaging (MRI), the system comprising:
   a CT subsystem for obtaining CT data;
   an MRI subsystem for obtaining MRI data;
   at least one processor; and
   a machine-readable medium, in operable communication with the CT subsystem, the MRI subsystem, and the at least one processor, having machine-executable instructions stored thereon that, when executed by the at least one processor, perform a method of reconstructing CT and MRI images, the method comprising:
   i) reconstructing a CT image $u_{CT}$ from the CT data;
   ii) reconstructing an MRI image $u_{MRI}$ from the MRI data;
   iii) setting an iteration step k=0;
   iv) transforming a CT-MRI dataset $T_{CT\text{-}MRI}$ by the $u_{CT}$ and $u_{MRI}$;
   v) estimating a corresponded CT-MRI image $u\frac{est}{CT}$ and $u\frac{est}{MRI}$ according to $u_{CT}$ and $u_{MRI}$ aided by the CT-MRI dataset $T_{CT\text{-}MRI}$;
   vi) reconstructing the CT image $u_{CT}$ with $u\frac{est}{CT}$ and the CT data;
   vii) reconstructing the MRI image $u_{MRI}$ with $u\frac{est}{MRI}$ and the MRI data;
   viii) setting k=k+1; and
   ix) repeating steps iv)-viii) until meeting stop criteria, at which point the current $u\frac{est}{CT}$ is the reconstructed CT image and the current $u\frac{est}{MRI}$ is the reconstructed MRI image,
   wherein estimating the corresponded CT-MRI image comprises using a structural coupling (SC) method, the SC method comprising:
   a) decomposing $u_{CT}$ into patches $p^j_{CT}=E_j u_{CT}$ where E is an operator to extract patches from an image;
   b) decomposing $u_{MRI}$ into patches $p^j_{MRI}=E_j u_{MRI}$;
   c) optimizing the following equation by finding K-best suitable patches $\{p^j_{CT,i}\}$ and $\{p^j_{MRI,i}\}$, and their weights $\{w_i\}$ in $T_{CT}$ and $T_{MRI}$ to represent $p^j_{CT}$ and $p^j_{MRI}$ $$\min_{\beta_i} \left\| p_{MRI} - \sum_i w_i T_{MRI}\beta_i \right\|_2^2 + \left\| p_{CT} - \sum_i w_i T_{CT}\beta_i \right\|_2^2,$$

where $w_i$ equals the average of CT and MRI weightings calculated according to the below equation, $w_i=(w_{CT,i}+w_{MRI,i})/2$, and $\beta_i$ identifies surrounding high-dimensional data points, $$w'_{*,i} = \exp(-\|p_* - p_{*,i}\|_2^2 / h^2) \text{ and } w_{*,i} = w'_{*,i} \Big/ \sum_i^K w'_{*,i},$$

where h is an empirical value that controls contributions of involved patches, and K is the number of surrounding data points;
   d) estimating CT and MRI image patches with the corresponded CT and MRI image pairs in $T_{CT\text{-}MRI}$ and new weights $\{w_i\}$, $$p^j_{new,CT} \approx \sum_i^K w_i p^j_{CT,i}, \quad p^j_{new,MRI} \approx \sum_i^K w_i p^j_{MRI,i};$$

e) estimating the corresponded CT image with $p^j_{new,CT}$, $$u^{est}_{CT} = \left(\sum_j E_j^T E_j\right)^{-1} \left(\sum_j E_j^T p^j_{new,CT}\right);$$

and
   f) estimating the corresponded MRI image with $p^j_{new,MRI}$, $$u^{est}_{MRI} = \left(\sum_j E_j^T E_j\right)^{-1} \left(\sum_j E_j^T p^j_{new,MRI}\right).$$

2. The system according to claim 1, wherein reconstructing the CT image $u_{CT}$ from the CT data comprises using the following equation:

$$\min_{u_{CT}} \|u_{CT}\|_{TV} \text{ s.t. } Mu_{CT} = f,$$

where M is a system matrix, f is line integral data after preprocessing, and $\|\cdot\|_{TV}$ represents a total variation (TV) transformation.

3. The system according to claim 1, wherein reconstructing the MRI image $u_{MRI}$ from the MRI data comprises using the following equation:

$$\min_{u_{MRI}} \|u_{MRI}\|_{TV} \text{ s.t. } RFu_{MRI} = g,$$

where F denotes a Fourier transform, R is a sampling mask in the k-space, g is the MRI data, and $\|\cdot\|_{TV}$ represents a total variation (TV) transformation.

4. The system according to claim 1, wherein reconstructing the CT image $u_{CT}$ with $$u_{CT}^{est}$$

and the CT data comprises using the following equation, $$\min_{u_{CT}}(1-\alpha)\|u_{CT}\|_{TV} + \alpha\|u_{CT} - u_{CT}^{est}\|_{TV} \text{ s.t. } Mu_{CT} = f,$$

where M is a system matrix, f is line integral data after preprocessing, $\alpha$ is a relaxation parameter, and $\|\cdot\|_{TV}$ represents a total variation (TV) transformation.

5. The system according to claim 1, wherein reconstructing the MRI image $u_{MRI}$ with $$u_{MRI}^{est}$$

and the MRI data comprises using the following equation, $$\min_{u_{MRI}}(1-\alpha)\|u_{MRI}\|_{TV} + \alpha\|u_{MRI} - u_{MRI}^{est}\|_{TV} \text{ s.t. } Fu_{MRI} = g,$$

where F denotes a Fourier transform, R is a sampling mask in the k-space, g is the MRI data, $\alpha$ is a relaxation parameter, and $\|\cdot\|_{TV}$ represents a total variation (TV) transformation.

6. The system according to claim 1, wherein steps iv) through vii) can be formulated as follows, $$\min_{(u_{CT}, u_{MRI}, \beta)} \|u_{CT}\|_{TV} + \lambda\|u_{MRI}\|_{TV} +$$

$$\gamma \sum_j \left( \left\| E_j u_{MRI} - \sum_i w_i T_{MRI} \beta_{j,i} \right\|_2^2 + \left\| E_j u_{CT} - \sum_i w_i T_{CT} \beta_{j,i} \right\|_2^2 \right)$$

$$\text{s.t. } Mu_{CT} = f, RFu_{MRI} = g,$$

where E is an operator to extract patches from an image, $\beta$ determines which patch is selected for linear approximation by assigning appropriate weighting factors $\{w_i\}$, M is a system matrix, f is line integral data after preprocessing, F denotes a Fourier transform, R is a sampling mask in the k-space, g is the MRI data, and $\|\cdot\|_{TV}$ represents a total variation (TV) transformation.

7. The system according to claim 1, wherein the SC method is implemented using a hashing method to accelerate a patch searching process.

8. The system according to claim 1, wherein the method of reconstructing CT and MRI images further comprises utilizing prior knowledge of prior CT images.

9. The system according to claim 8, wherein the prior knowledge of CT images comprises information from a CT image atlas.

10. The system according to claim 9, wherein the prior knowledge of CT images is utilized in step i).

11. The system according to claim 1, wherein the method of reconstructing CT and MRI images further comprises utilizing prior knowledge of prior MRI images.

12. The system according to claim 11, wherein the prior knowledge of MRI images comprises information from an MRI image atlas.

13. The system according to claim 12, wherein the prior knowledge of MRI images is utilized in step i).

14. The system according to claim 1, wherein the MRI subsystem comprises superconducting magnets.

15. The system according to claim 1, wherein the MRI subsystem comprises two donut shaped magnets facing each other.

16. The system according to claim 1, wherein the MRI subsystem comprises two hexagonal magnet arrays facing each other.

17. The system according to claim 1, wherein the CT subsystem and the MRI subsystem are seamlessly integrated with one another.

18. The system according to claim 1, wherein components of the CT subsystem are quasi-stationary.

19. The system according to claim 18, wherein X-ray sources and detectors of the CT subsystem are distributed face-to-face along a circle.

20. The system according to claim 1, wherein the CT data comprises only a few-view set of CT data.

21. The system according to claim 1, wherein the method of reconstructing CT and MRI images further comprises using a compressive sensing (CS) method.

22. A non transitory machine-readable medium, having machine-executable instructions stored thereon that, when executed by at least one processor, perform a method of reconstructing CT and MRI images, the method comprising:
  i) reconstructing a CT image $u_{CT}$ from CT data;
  ii) reconstructing an MRI image $u_{MRI}$ from MRI data;
  iii) setting an iteration step k=0;
  iv) transforming a CT-MRI dataset $T_{CT\text{-}MRI}$ by the $u_{CT}$ and $u_{MRI}$;
  v) estimating a corresponded CT-MRI image $$u_{CT}^{est} \text{ and } u_{MRI}^{est}$$

according to $u_{CT}$ and $u_{MRI}$ aided by the CT-MRI dataset $T_{CT\text{-}MRI}$;
  vi) reconstructing the CT image $u_{CT}$ with $$u_{CT}^{est}$$

and the CT data;
  vii) reconstructing the MRI image $u_{MRI}$ with $$u_{MRI}^{est}$$

and the MRI data;
  viii) setting k=k+1; and
  ix) repeating steps iv)-viii) until meeting stop criteria, at which point the current $$u_{CT}^{est}$$

is the reconstructed CT image and the current $$u_{MRI}^{est}$$

is the reconstructed MRI image,
wherein estimating the corresponded CT-MRI image comprises using a structural coupling (SC) method, the SC method comprising:
a) decomposing $u_{CT}$ into patches $p^j_{CT}=E_j u_{CT}$ where E is an operator to extract patches from an image;
b) decomposing $u_{MRI}$ into patches $p^j_{MRI}=E_j u_{MRI}$;
c) optimizing the following equation by finding K-best suitable patches $\{p^j_{CT,i}\}$ and $\{p^j_{MRI,i}\}$, and their weights $\{w_i\}$ in $T_{CT}$ and $T_{MRI}$ to represent $p^j_{CT}$ and $p^j_{MRI}$, $$\min_{\beta_i} \left\| p_{MRI} - \sum_i w_i T_{MRI} \beta_i \right\|_2^2 + \left\| p_{CT} - \sum_i w_i T_{CT} \beta_i \right\|_2^2,$$

where $w_i$ equals the average of CT and MRI weightings calculated according to the below equation, $w_i=(w_{CT,i}+w_{MRI,i})/2$, and $\beta_i$ identifies surrounding high-dimensional data points, $$w'_{*,i} = \exp(-\|p_* - p_{*,i}\|_2^2/h^2) \text{ and } w_{*,i} = w'_{*,i} / \sum_i^K w'_{*,i},$$

where h is an empirical value that controls contributions of involved patches, and K is the number of surrounding data points;
d) estimating CT and MRI image patches with the corresponded CT and MRI image pairs in $T_{CT-MRI}$ and new weights $\{w_i\}$, $$p^j_{new,CT} \approx \sum_i^K w_i p^j_{CT,i}, \quad p^j_{new,MRI} \approx \sum_i^K w_i p^j_{MRI,i};$$

e) estimating the corresponded CT image with $p^j_{new,CT}$, $$u_{CT}^{est} = \left(\sum_j E_j^T E_j\right)^{-1} \left(\sum_j E_j^T p^j_{new,CT}\right);$$

and
f) estimating the corresponded MRI image with $p^j_{new,MRI}$, $$u_{MRI}^{est} = \left(\sum_j E_j^T E_j\right)^{-1} \left(\sum_j E_j^T p^j_{new,MRI}\right).$$

23. The machine-readable medium according to claim 22, wherein reconstructing the CT image $u_{CT}$ from the CT data comprises using the following equation:

$$\min_{u_{CT}} \|y_{CT}\|_{TV} \text{ s.t. } Mu_{CT}=f,$$

where M is a system matrix, f is line integral data after preprocessing, and $\|\bullet\|_{TV}$ represents a total variation (TV) transformation.

24. The machine-readable medium according to claim 22, wherein reconstructing an MRI image $u_{MRI}$ from the MRI data comprises using the following equation:

$$\min_{u_{MRI}} \|u_{MRI}\|_{TV} \text{ s.t. } RFu_{MRI}=g,$$

where F denotes a Fourier transform, R is a sampling mask in the k-space, g is the MRI data, and $\|\bullet\|_{TV}$ represents a total variation (TV) transformation.

25. The machine-readable medium according to claim 22, wherein reconstructing the CT image $u_{CT}$ with $$u_{CT}^{est}$$

and CT data comprises using the following equation, $$\min_{u_{CT}} (1-\alpha)\|u_{CT}\|_{TV} + \alpha\|u_{CT} - u_{CT}^{est}\|_{TV} \text{ s.t. } Mu_{CT}=f,$$

where M is a system matrix, f is line integral data after preprocessing, α is a relaxation parameter, and $\|\bullet\|_{TV}$ represents a total variation (TV) transformation.

26. The machine-readable medium according to claim 22, wherein reconstructing the MRI image $u_{MRI}$ with $$u_{MRI}^{est}$$

and the MRI data comprises using the following equation, $$\min_{u_{MRI}} (1-\alpha)\|u_{MRI}\|_{TV} + \alpha\|u_{MRI} - u_{MRI}^{est}\|_{TV}$$

s.t. $Fu_{MRI}=g,$ where F denotes a Fourier transform, R is a sampling mask in the k-space, g is the MRI data, α is a relaxation parameter, and $\|\bullet\|_{TV}$ represents a total variation (TV) transformation.

27. The machine-readable medium according to claim 22, wherein steps iv) through vii) can be formulated as follows, $$\min_{(u_{CT}, u_{MRI}, \beta)} \|u_{CT}\|_{TV} + \lambda\|u_{MRI}\|_{TV} +$$

$$\gamma \sum_j \left( \left\|E_j u_{MRI} - \sum_i w_i T_{MRI} \beta_{j,i}\right\|_2^2 + \left\|E_j u_{CT} - \sum_i w_i T_{CT} \beta_{j,i}\right\|_2^2 \right)$$

s.t. $Mu_{CT}=f, RFu_{MRI}=g,$ where E is an operator to extract patches from an image, β determines which patch is selected for linear approximation by assigning appropriate weighting factors {$w_i$}, M is a system matrix, f is line integral data after preprocessing, F denotes a Fourier transform, R is a sampling mask in the k-space, g is the MRI data, and $\|\cdot\|_{TV}$ represents a total variation (TV) transformation.

28. The machine-readable medium according to claim 22, wherein the SC method is implemented using a hashing method to accelerate a patch searching process.

29. The machine-readable medium according to claim 22, wherein the method of reconstructing CT and MRI images further comprises utilizing prior knowledge of prior CT images.

30. The machine-readable medium according to claim 29, wherein the prior knowledge of CT images comprises information from a CT image atlas.

31. The machine-readable medium according to claim 30, wherein the prior knowledge of CT images is utilized in step i).

32. The machine-readable medium according to claim 22, wherein the method of reconstructing CT and MRI images further comprises utilizing prior knowledge of prior MRI images.

33. The machine-readable medium according to claim 32, wherein the prior knowledge of MRI images comprises information from an MRI image atlas.

34. The machine-readable medium according to claim 33, wherein the prior knowledge of MRI images is utilized in step i).

35. The machine-readable medium according to claim 22, wherein the CT data comprises only a few-view set of CT data.

36. The machine-readable medium according to claim 22, wherein the method of reconstructing CT and MRI images further comprises using a compressive sensing (CS) method.

37. A method of reconstructing CT and MRI images, the method comprising:
  i) reconstructing a CT image $u_{CT}$ from CT data;
  ii) reconstructing an MRI image $u_{MRI}$ from MRI data;
  iii) setting an iteration step k=0;
  iv) transforming a CT-MRI dataset $T_{CT-MRI}$ by the $u_{CT}$ and $u_{MRI}$;
  v) estimating a corresponded CT-MRI image $$u^{est}_{CT} \text{ and } u^{est}_{MRI}$$

according to $u_{cT}$ and $u_{MRI}$ aided by the CT-MRI dataset $T_{CT-MRI}$;
  vi) reconstructing the CT image $u_{cT}$ with $$u^{est}_{CT}$$

and the CT data;
  vii) reconstructing the MRI image $u_{MRI}$ with $$u^{est}_{MRI}$$

and the MRI data;
  viii) setting k=k+1; and
  ix) repeating steps iv)-viii) until meeting stop criteria, at which point the current $$u^{est}_{CT}$$

is the reconstructed CT image and the current $$u^{est}_{MRI}$$

is the reconstructed MRI image,
    wherein estimating the corresponded CT-MRI image comprises using a structural coupling (SC) method, the SC method comprising:
    a) decomposing $u_{CT}$ into patches $p^j_{CT}=E_j u_{CT}$ where E is an operator to extract patches from an image;
    b) decomposing $u_{MRI}$ into patches $p^j_{MRI}=E_j u_{MRI}$;
    c) optimizing the following equation by finding K-best suitable patches {$p^j_{CT,i}$} and {$p^j_{MRI,i}$}, and their weights {$w_i$} in $T_{CT}$ and $T_{MRI}$ to represent $p^j_{CT}$ and $p^j_{MRI}$ $$\min_{\beta_i} \left\| p_{MRI} - \sum_i w_i T_{MRI} \beta_i \right\|_2^2 + \left\| p_{CT} - \sum_i w_i T_{CT} \beta_i \right\|_2^2,$$

where $w_i$ equals the average of CT and MRI weightings calculated according to the below equation, $w_i=(w_{CT,i}+w_{MRI,i})/2$, and $\beta_i$ identifies surrounding high-dimensional data points, $$w'_{*,i} = \exp(-\|p_* - p_{*,i}\|_2^2/h^2) \text{ and } w_{*,i} = w'_{*,i} \bigg/ \sum_i^K w'_{*,i},$$

where h is an empirical value that controls contributions of involved patches, and K is the number of surrounding data points;
    d) estimating CT and MRI image patches with the corresponded CT and MRI image pairs in $T_{CT-MRI}$ and new weights {$w_i$}, $$p^j_{new,CT} \approx \sum_i^K w_i p^j_{CT,i}, \quad p^j_{new,MRI} \approx \sum_i^K w_i p^j_{MRI,i};$$

e) estimating the corresponded CT image with $p^j_{new,CT}$, $$u^{est}_{CT} = \left(\sum_j E_j^T E_j\right)^{-1} \left(\sum_j E_j^T p^j_{new,CT}\right);$$

and
    f) estimating the corresponded MRI image with $p^j_{new,CT}$, $$u^{est}_{MRI} = \left(\sum_j E_j^T E_j\right)^{-1} \left(\sum_j E_j^T p^j_{new,MRI}\right).$$

38. The method according to claim 37, wherein reconstructing the CT image $u_{CT}$ from the CT data comprises using the following equation:

$$\min_{u_{CT}} \|u_{CT}\|_{TV} \text{ s.t. } Mu_{CT} = f,$$

where M is a system matrix, f is line integral data after preprocessing, and $\|\cdot\|_{TV}$ represents a total variation (TV) transformation.

39. The method according to claim 37, wherein reconstructing the MRI image $u_{MRI}$ from the MRI data comprises using the following equation:

$$\min_{u_{MRI}} \|u_{MRI}\|_{TV} \text{ s.t. } RFu_{MRI} = g,$$

where F denotes a Fourier transform, R is a sampling mask in the k-space, g is the MRI data, and $\|\cdot\|_{TV}$ represents a total variation (TV) transformation.

40. The method according to claim 37, wherein reconstructing the CT image $u_{CT}$ with $$u_{CT}^{est}$$

and the CT data comprises using the following equation, $$\min_{u_{CT}} (1-\alpha) \|u_{CT}\|_{TV} + \alpha \|u_{CT} - u_{CT}^{est}\|_{TV} \text{ s.t. } Mu_{CT} = f,$$

where M is a system matrix, f is line integral data after preprocessing, $\alpha$ is a relaxation parameter, and $\|\cdot\|_{TV}$ represents a total variation (TV) transformation.

41. The method according to claim 37, wherein reconstructing the MRI image $u_{MRI}$ with $$u_{MRI}^{est}$$

and the MRI data comprises using the following equation, $$\min_{u_{MRI}} (1-\alpha) \|u_{MRI}\|_{TV} + \alpha \|u_{MRI} - u_{MRI}^{est}\|_{TV}$$
$$\text{s.t. } Fu_{MRI} = g,$$

where F denotes a Fourier transform, R is a sampling mask in the k-space, g is the MRI data, $\alpha$ is a relaxation parameter, and $\|\cdot\|_{TV}$ represents a total variation (TV) transformation.

42. The method according to claim 37, wherein steps iv) through vii) can be formulated as follows, $$\min_{(u_{CT}, u_{MRI}, \beta)} \|u_{CT}\|_{TV} + \lambda \|u_{MRI}\|_{TV} + \quad (9)$$
$$\gamma \sum_j \left( \left\| E_j u_{MRI} - \sum_i w_i T_{MRI} \beta_{j,i} \right\|_2^2 + \left\| E_j u_{CT} - \sum_i w_i T_{CT} \beta_{j,i} \right\|_2^2 \right)$$
$$\text{s.t. } Mu_{CT} = f, RFu_{MRI} = g,$$

where E is an operator to extract patches from an image, $\beta$ determines which patch is selected for linear approximation by assigning appropriate weighting factors $\{w_i\}$, M is a system matrix, f is line integral data after preprocessing, F denotes a Fourier transform, R is a sampling mask in the k-space, g is the MRI data, and $\|\cdot\|_{TV}$ represents a total variation (TV) transformation.

43. The method according to claim 37, wherein the SC method is implemented using a hashing method to accelerate a patch searching process.

44. The method according to claim 37, wherein the method of reconstructing CT and MRI images further comprises utilizing prior knowledge of prior CT images.

45. The method according to claim 44, wherein the prior knowledge of CT images comprises information from a CT image atlas.

46. The method according to claim 45, wherein the prior knowledge of CT images is utilized in step i).

47. The method according to claim 37, wherein the method of reconstructing CT and MRI images further comprises utilizing prior knowledge of prior MRI images.

48. The method according to claim 47, wherein the prior knowledge of MRI images comprises information from an MRI image atlas.

49. The method according to claim 48, wherein the prior knowledge of MRI images is utilized in step i).

50. The method according to claim 37, wherein the CT data comprises only a few-view set of CT data.

51. The method according to claim 37, wherein the method of reconstructing CT and MRI images further comprises using a compressive sensing (CS) method.

\* \* \* \* \*